United States Patent
Shoshan-Barmatz et al.

(10) Patent No.: US 10,946,013 B2
(45) Date of Patent: *Mar. 16, 2021

(54) METHODS FOR TREATING CENTRAL NERVOUS SYSTEM DISORDERS USING VDAC INHIBITORS

(71) Applicant: The National Institute for Biotechnology in the Negev Ltd., Beer-Sheva (IL)

(72) Inventors: Varda Shoshan-Barmatz, Omer (IL); Arie Lev Gruzman, Jerusalem (IL)

(73) Assignee: The National Institute for Biotechnology in the Negev Ltd., Beer-Sheva (IL)

( * ) Notice: Subject to any disclaimer, the term of this patent is extended or adjusted under 35 U.S.C. 154(b) by 0 days.

This patent is subject to a terminal disclaimer.

(21) Appl. No.: 16/560,668

(22) Filed: Sep. 4, 2019

(65) Prior Publication Data
US 2020/0000801 A1    Jan. 2, 2020

Related U.S. Application Data

(63) Continuation of application No. 15/700,801, filed on Sep. 11, 2017, now Pat. No. 10,434,099, and a continuation-in-part of application No. 15/567,807, filed as application No. PCT/IL2016/051020 on Sep. 13, 2016, now Pat. No. 10,508,091.

(60) Provisional application No. 62/397,991, filed on Sep. 22, 2016, provisional application No. 62/217,986, filed on Sep. 14, 2015.

(51) Int. Cl.
*A61K 31/496* (2006.01)
*A61K 31/495* (2006.01)
*A61K 31/435* (2006.01)
*A61K 31/454* (2006.01)
*A61K 31/4468* (2006.01)

(52) U.S. Cl.
CPC .......... *A61K 31/496* (2013.01); *A61K 31/435* (2013.01); *A61K 31/4468* (2013.01); *A61K 31/454* (2013.01); *A61K 31/495* (2013.01)

(58) Field of Classification Search
CPC .. A61K 31/496; A61K 31/435; A61K 31/454; A61K 31/495; A61K 31/4468
USPC ........................................................ 514/254
See application file for complete search history.

(56) References Cited

U.S. PATENT DOCUMENTS 10,434,099 B2 * 10/2019 Shoshan-Barmatz ........................ A61K 31/4468
10,508,091 B2 * 12/2019 Shoshan-Barmatz ........................ A61K 31/454

2004/0029887 A1  2/2004  Bhatia
2018/0118700 A1  5/2018  Shoshan-Barmatz
2020/0115348 A1* 4/2020  Shoshan-Barmatz ................ C07D 403/04

FOREIGN PATENT DOCUMENTS

| CN | 1944424 A | 4/2007 |
| CN | 1948298 B | 9/2010 |
| JP | S50108264 A | 8/1975 |
| WO | 03028728 A1 | 4/2003 |
| WO | 2008063984 A2 | 5/2008 |
| WO | 2014192865 A1 | 12/2014 |
| WO | 2015099196 A1 | 7/2015 |
| WO | 2017046794 A1 | 3/2017 |

OTHER PUBLICATIONS

Park et al., (2007) Lead discovery and optimization of T-type calcium channel blockers. Bioorg Med Chem 15(3): 1409-1419.
Chemical Abstract Registry No. 1385531-42-9, indexed in the Registry File on STN CAS Online, Aug. 2, 2012; 1 page.
Alamed et al., (2006) Two-day radial-arm water maze learning and memory task; robust resolution of amyloid-related memory deficits in transgenic mice. Nat Protoc 1(4): 1671-1679.
Arrzoine et al., (2009) Voltage-dependent anion channel 1-based peptides interact with hexokinase to prevent its anti-apoptotic activity. J Biol Chem 284(6): 3946-3955.
Bauer et al., (2011) Functional model of metabolite gating by human voltage-dependent anion channel 2. Biochemistry 50(17): 3408-3410.
Baumgartner et al., (2009) Calcium elevation in mitochondria is the main Ca2+ requirement for mitochondrial permeability transition pore (mPTP) opening. J Biol Chem 284(31): 20796-20803.
Ben-Hail and Shoshan-Barmatz (2016) VDAC1-interacting anion transport inhibitors inhibit VDAC1 oligomerization and apoptosis. Biochim Biophys Acta 1863(7 Pt A): 1612-1623.
Ben-Hail et al., (2016) Novel Compounds Targeting the Mitochondrial Protein VDAC1 Inhibit Apoptosis and Protect against Mitochondrial Dysfunction. J Biol Chem 291(48): 24986-25003.
Betarbet et al., (2002) Animal models of Parkinson's disease. Bioessays 24(4): 308-318.
Enomoto and Floresco (2003) Disruptions in spatial working memory, but not short-term memory, induced by repeated ketamine exposure. Prog Neuropsychopharmacol Biol Psychiatry 33(4): 668-675.
Falk et al., (2016) Modeling psychiatric disorders: from genomic findings to cellular phenotypes. Mol Psychiatry 21(9): 1167-1179.
Fernandez-Echevarria et al., (2014) A13 promotes VDAC1 channel dephosphorylation in neuronal lipid rafts. Relevance to the mechanisms of neurotoxicity in Alzheimers disease. Neuroscience 278: 354-366.

(Continued)

*Primary Examiner* — Kristin A Vajda
(74) *Attorney, Agent, or Firm* — Leason Ellis LLP

(57) ABSTRACT

The present invention relates to use of small organic compounds interacting with the Voltage-Dependent Anion Channel (VDAC) for the treatment of diseases associated with central nervous system (CNS) disorders, including psychotic disorders, mood disorders, neurodegenerative diseases. In particular the present invention relates to the use of substituted piperazine- and piperidine-derivatives and pharmaceutical compositions comprising same for the treatment of psychotic disorders including schizophrenia, mood disorders, and neurodegenerative diseases.

20 Claims, 12 Drawing Sheets

(56) References Cited

OTHER PUBLICATIONS

Gonzalez-Gronow et al., (2010) Antibodies against the voltage-dependent anion channel (VDAC) and its protective ligand hexokinase-I in children with autism. Journal of Neuroimmunology 227: 153-161.
Grauer et al., (2009) WAY-163909, a 5-HT2C agonist, enhances the preclinical potency of current antipsychotics. Psychopharmacology (Berl) 204(1): 37-48.
Gu (2007) Synthesis of phenylpiperazino compuounds as dopamine D3 receptor ligands. Journal of Hainan Normal University (Natural Science) 20(4): 342-345 & 360 (w/ English abstract on p. 360).
Guo et al., (2014) Discovery of aroyl piperazine derivatives as IKr & IKs dual inhibitors for cardiac arrhythmia treatment. Med Chem (5): 497-505.
Hörig and Pullman (2004) From bench to clinic and back: Perspective on the 1st IQPC Translational Research conference. J Transl Med 2(1): 44; 8 pages.
Howland et al., (2002) Focal loss of the glutamate transporter EAAT2 in a transgenic rat model of SOD1 mutant-mediated amyotrophic lateral sclerosis (ALS). Proc Natl Acad Sci U S A 99(3): 1604-1609.
Journigan et al., (2014) Nonpeptide small molecule agonist and antagonist original leads for neuropeptide FF1 and FF2 receptors. J Med Chem 57(21): 8903-8927.
Keinan et al., (2010) Oligomerization of the mitochondrial protein voltage-dependent anion channel is coupled to the induction of apoptosis. Mol Cell Biol 30(24): 5698-5709.
Keinan et al., (2013) The role of calcium in VDAC1 oligomerization and mitochondria-mediated apoptosis. Biochim Biophys Acta 1833(7): 1745-1754.
Kempter et al., (1983) Synthese von heteroanalogen Piperidinoacetaniliden (English translation: "Syntehsis of heteroanalogs of piperidinoacetanilides") Wissenschaftliche Zeitschrift—Martin-LutherUniversität Halle Wittenberg-Mathematisch-Naturwissenschaftliche Reihe 32(5): 3-25 (w/ English summary on p. 23).
Lin et al., (2012) Differential long term effects of early diisopropylfluorophosphate exposure in Balb/C and C57Bl/J6 mice. Int J Dev Neurosci 30(2): 113-120.
Makadia and Siegel (2011) Poly Lactic-co-Glycolic Acid (PLGA) as Biodegradable Controlled Drug Delivery Carrier. Polymers (Basel) 3(3): 1377-1397.
Nabeshima et al., (2006) Animal model of schizophrenia: dysfunction of NMDA receptor-signaling in mice following withdrawal from repeated administration of phencyclidine. Ann N Y Acad Sci 1086: 160-168.
Obniska et al., (2006) Synthesis, anticonvulsant activity and 5-Ht1A, 5-HT2A receptor affinity of new N-[(4-arylpiperazin-1-yl)alkyl] derivatives of 2-azaspiro[4.4]nonane and [4.5]decane-1,3-dione. Eur J Med Chem 41(7): 874-881.
Okatsu et al., (2012) Mitochondrial hexokinase HKI is a novel substrate of the Parkin ubiquitin ligase. Biochem Biophys Res Commun 428(1): 197-202.
Petit-Demouliere et al., (2005) Forced swimming test in mice: a review of antidepressant activity. Psychopharmacology (Berl) 177(3): 245-255.
Regenold et al., (2012) Mitochondrial detachment of hexokinase 1 in mood and psychotic disorders: implications for brain energy metabolism and neurotrophic signaling. J Psychiatr Res 46(1): 95-104.
Rezin et al., (2009) Mitochondrial dysfunction and psychiatric disorders. Neurochem Res 34(6): 1021-1029.
Rosa and César (2016) Role of Hexokinase and VDAC in Neurological Disorders. Current Molecular Pharmacology 9 (4): 320-331.
Rosenmann et al., (2008) A novel transgenic mouse expressing double mutant tau driven by its natural promoter exhibits tauopathy characteristics. Exp Neurol 212(1): 71-84.
Saraiva et al., (2010) Amyloid-β triggers the release of neuronal hexokinase 1 from mitochondria. PLoS One 5(12): e15230; 8 pages.
Schäfer and Kolkhof (2008) Failure is an option: learning from unsuccessful proof-of-concept trials. Drug Discov Today 13(21-22): 913-916.
Shan et al., (2014) Abnormal partitioning of hexokinase 1 suggests disruption of a glutamate transport protein complex in schizophrenia. Schizophr Res 154(1-3): 1-13.
Shoshan-Barmatz and Ben-Hail (2012) VDAC, a multi-functional mitochondrial protein as a pharmacological target. Mitochondrion 12(1): 24-34.
Shoshan-Barmatz and Golan (2012) Mitochondrial VDAC1: function in cell life and death and a target for cancer therapy. Curr Med Chem 19(5): 714-735.
Shoshan-Barmatz et al., (2009) Key regions of VDAC1 functioning in apoptosis induction and regulation by hexokinase. Biochim Biophys Acta 1787(5): 421-430.
Shoshan-Barmatz et al., (2010) VDAC, a multi-functional mitochondrial protein regulating cell life and death. Mol Aspects Med 31(3): 227-285.
Shoshan-Barmatz et al., (2015) The mitochondrial voltage-dependent anion channel 1 in tumor cells. Biochim Biophys Acta 1848(10 Pt B): 2547-2575.
Shoshan-Barmatz et al., (2018) VDAC1, mitochondrial dysfunction, and Alzheimer's disease. Pharmacol Res 131: 87-101.
Tremolizzo et al., (2002) An epigenetic mouse model for molecular and behavioral neuropathologies related to schizophrenia vulnerability. Proc Natl Acad Sci U S A 99(26): 17095-17100.
Van Spronsen and Hoogenraad (2010) Synapse pathology in psychiatric and neurologic disease. Curr Neurol Neurosci Rep 10(3): 207-214.
Webster et al., (2014) Using mice to model Alzheimer's dementia: an overview of the clinical disease and the preclinical behavioral changes in 10 mouse models. Front Genet 5: 88; 23 pages.
Zhang et al., (2006) In silico design and synthesis of piperazine-1-pyrrolidine-2,5-dione scaffold-based novel malic enzyme inhibitors. Bioorg Med Chem Lett 16(3): 525-528.
Chemical Abstract Registry No. 792941-16-3, indexed in the Registry File on STN CAS Online, Dec. 6, 2004.
Chemical Abstract Registry No. 924861-14-3, indexed in the Registry File on STN CAS Online, Mar. 5, 2007.
Registry No. 89474-12-4, (STN search), dated Nov. 16, 1984 (Nov. 16, 1984); 1 page.
Registry No. 1385037-69-3, (STN search), dated Aug. 1, 2012 (Aug. 1, 2012); 1 page.
Supplementary European search report issued in EP Application No. 16845836.2 dated Feb. 12, 2019; 6 pages.

* cited by examiner

* p<0.05

METHODS FOR TREATING CENTRAL NERVOUS SYSTEM DISORDERS USING VDAC INHIBITORS

FIELD OF THE INVENTION

The present invention relates to use of small organic compounds interacting with the Voltage-Dependent Anion Channel (VDAC) for the treatment of central nervous system (CNS) disorders and diseases. In particular the present invention relates to the use of substituted piperazine- and piperidine-derivatives and pharmaceutical compositions comprising them for the treatment of psychotic disorders including schizophrenia, mood disorders including bipolar disorder, and neurodegenerative diseases including Alzheimer's disease, Parkinson's disease and Amyotrophic Lateral Sclerosis (ALS).

BACKGROUND OF THE INVENTION

VDAC forms the main interface between mitochondrial and cellular metabolisms by mediating the fluxes of ions, nucleotides and other metabolites across the outer mitochondrial membrane (OMM) (Shoshan-Barmatz, V et al. 2010. Molecular Aspects of Medicine 31(3), 227-286; Shoshan-Barmatz V and Ben-Hail D. 2012. Mitochondrion, 12(1): 24-34). VDAC has also been recognized as a key protein in mitochondria-mediated apoptosis. VDAC mediates the release of apoptosis-inducing proteins from mitochondria to the cytosol and regulates apoptosis via interaction with pro- and anti-apoptotic proteins (Shoshan-Barmatz V et al. 2010, ibid; Shoshan-Barmatz V and Golan M. 2012. Current Medicinal Chemistry 19(5), 714-735).

Mitochondrial-bound hexokinase (HK), subtypes I and II (HK-I and HK-II), functions in the coupling of cytosolic glycolysis to mitochondrial oxidative phosphorylation. This is mediated via HK interaction with VDAC1. VDAC1-bound HK also prevents the release of pro-apoptotic factors, and subsequent apoptosis accompanied with detachment of HK. HK detachment from mitochondria has been observed in several pathological conditions, such as Alzheimer's Disease (Saraiva, L M et al. 2010. PLoS ONE 5, e15230), Parkinson's disease (Okatsu, K et al. 2012. Biochem Biophys Res Commun 428, 197-202) and mood and psychotic disorders, including schizophrenia (Rezin G T et al., 2009. Neurochem Res 34, 1021-1029; Regenold, W T ET AL., 2012. J. Psychiatr Res. 46, 95-104; Shan, D et al. 2014. Schizophr Res 154, 1-13).

Piperazine and piperidine are used as essential sub-structure motifs in various drugs. Piperazine pyrrolidine-2,5-dione derivatives have also been demonstrated as malic enzyme inhibitors (Zhang Y J et al. 2006. Bioorganic & Medicinal Chemistry Letters 16, 525-528).

A publication of the inventors of the present invention and co-workers, published after the priority date of the present invention, describes compounds that directly interact with VDAC1 and prevent VDAC1 oligomerization, concomitant with an inhibition of apoptosis as induced by various means and in various cell lines. The compounds protected against apoptosis-associated mitochondrial dysfunction, restoring dissipated mitochondrial membrane potential, and thus cell energy and metabolism, decreasing reactive oxidative species production, and preventing detachment of hexokinase bound to mitochondria and disruption of intracellular $Ca^{2+}$ levels (Ben Hail D et al., 2016. J Biol Chem 291(48), 24986-25003).

Central nervous system (CNS) disorders are diseases that can affect the brain or spinal cord. The CNS disorders may be caused by trauma, infections, degeneration, structural defects, tumors, blood flow disruption, autoimmunity, or strokes. There exists a wide range of treatments for these disorders, such as surgery, rehabilitation, and medications. Examples of CNS medications include analgesics, anticonvulsants, antipsychotics, sedatives, and tranquilizers. Despite their beneficial effects, CNS medications have the potential for developing tolerance, dependence, or addiction. Psychiatric disorders, including mood disorders and schizophrenia, as well as neurodegenerative disease, are devastating CNS associated diseases with no effective, side-effect free treatment.

Thus, there remains a need for improved treatments of CNS disorders, particularly psychiatric disorders and neurodegenerative diseases that provide increased efficacy and reduces or eliminates any potential side effects.

SUMMARY OF THE INVENTION

The present invention provides methods for treating diseases associated with CNS disorders, employing small organic compounds interacting with and inhibiting VDAC activities associated with apoptosis and energy metabolism, particularly inhibiting VDAC oligomerization and the detachment of HK-I from mitochondria.

The present invention provides a method for treating CNS-associated disease selected from the group consisting of neurodegenerative disease, mood disorder and psychotic disorder, comprising administering to a subject in need thereof a therapeutically effective amount of at least one substituted piperazine and piperidine derivative of general formula (I) as defined hereinafter, including the stereoisomers, enantiomers, mixtures thereof and salts thereof.

The present invention is based in part on the unexpected discovery that compounds of general Formulae (I) inhibit the oligomerization of mitochondrial Voltage-Dependent Anion Channel (VDAC) protein, and, furthermore, inhibit the detachment of hexokinase from the mitochondrial VDAC1, affecting energy metabolism and inhibiting apoptosis. The compounds are therefore suitable for the treatment of CNS-associated disorders, particularly mood and psychotic disorders, including schizophrenia. In addition the compounds are effective for the treatment of neurodegenerative disease, particularly Alzheimer's disease, Parkinson disease and amyotrophic lateral sclerosis (ALS).

According to one aspect, the present invention provides a method for treating CNS-associated disorder, the method comprising administering to a subject in need thereof a pharmaceutical composition comprising a therapeutically effective amount of at least one compound of the general Formula (I):

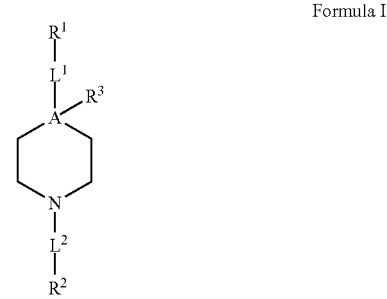

Formula I wherein:

A is carbon (C) or nitrogen (N);

$R^3$ is absent, or is selected from a hydrogen, an unsubstituted or substituted amide or a heteroalkyl group comprising 3-12 atoms apart from hydrogen atoms, wherein at least one of said 3-12 atoms is a heteroatom, selected from nitrogen, sulfur and oxygen; wherein when A is nitrogen (N), $R^3$ is absent;

$L^1$ is absent or is an amino linking group —$NR^4$—, wherein $R^4$ is hydrogen, a $C_{1-5}$ alkyl, a $C_1$-s-alkylene or a substituted alkyl —$CH_2R$, wherein R is a functional group selected from the group consisting of hydrogen, halo, haloalkyl, cyano, nitro, hydroxyl, alkyl, alkenyl, aryl, alkoxyl, aryloxyl, aralkoxyl, alkylcarbamido, arylcarbamido, amino, alkylamino, arylamino, dialkylamino, diarylamino, arylalkylamino, aminocarbonyl, alkylaminocarbonyl, arylaminocarbonyl, alkylcarbonyloxy, arylcarbonyloxy, carboxyl, alkoxycarbonyl, aryloxycarbonyl, sulfo, alkylsulfonylamido, alkylsulfonyl, arylsulfonyl, alkylsulfinyl, arylsulfinyl and heteroaryl;

$R^1$ is an aromatic moiety, which is optionally substituted with one or more of Z;

Z is independently at each occurrence a functional group selected from the group consisting of, hydrogen, halo, haloalkyl, haloalkoxy, perhaloalkoxy or $C_{1-2}$ perfluoroalkoxy, cyano, nitro, hydroxyl, alkyl, alkenyl, aryl, alkoxyl, aryloxyl, aralkoxyl, alkylcarbamido, arylcarbamido, amino, alkylamino, arylamino, dialkylamino, diarylamino, arylalkylamino, aminocarbonyl, alkylaminocarbonyl, arylaminocarbonyl, alkylcarbonyloxy, arylcarbonyloxy, carboxyl, alkoxycarbonyl, aryloxycarbonyl, sulfo, alkylsulfonylamido, alkylsulfonyl, arylsulfonyl, alkylsulfinyl, arylsulfinyl and heteroaryl;

$L^2$ is a linking group, such that when A is nitrogen (N), $L^2$ is a group consisting of 4-10 atoms, apart from hydrogen atoms, optionally forming a ring, whereof at least one of the atoms is nitrogen, said nitrogen forming part of an amide group; and when A is carbon (C), then $L^2$ is selected from $C_{1-4}$ alkylene or a group consisting of 4-10 atoms, apart from hydrogen atoms, optionally forming a ring, whereof at least one of the atoms is nitrogen, said nitrogen forming part of an amide group; and $R^2$ is a phenyl or a naphthyl, optionally substituted with halogen;

The invention also relates to the stereoisomers, enantiomers, mixtures thereof and salts thereof, of the compounds of general Formula I, and all their derivatives, according to the invention.

According to some embodiments, the psychotic disorder is selected from the group consisting of, but not limited to, schizophrenia, autism spectrum disorder and anorexia nervosa. Each possibility represents a separate embodiment of the present invention. According to certain exemplary embodiments, the psychotic disorder is schizophrenia.

According to certain embodiments, the mood disorder is selected from the group consisting of, but not limited to, bipolar disorder, major depressive disorder, persistent depressive disorder (also known as dysthymia) and anxiety disorder. Each possibility represents a separate embodiment of the present invention.

According to certain exemplary embodiments, the mood disorder is bipolar disorder.

According to certain embodiments, the neurodegenerative disease is selected from the group consisting of, but not limited to, Alzheimer's disease, Parkinson's disease and Amyotrophic Lateral Sclerosis (ALS). Each possibility represents a separate embodiment of the present invention.

According to certain exemplary embodiments, the neurodegenerative disease is Alzheimer's disease.

According to certain additional or alternative embodiments, the neurodegenerative disease is Parkinson's disease.

According to certain additional or alternative embodiments, the neurodegenerative disease is ALS.

According to certain exemplary embodiments, the compounds of the present invention are administered to the subject in need thereof within a pharmaceutical composition further comprising a pharmaceutically acceptable excipient, diluents or carriers.

According to some embodiments, the pharmaceutical composition further comprises at least one additional active agent.

Other aspects and embodiments of the present invention will become apparent to the skilled person from the following detailed description.

DETAILED DESCRIPTION

Figure 1:
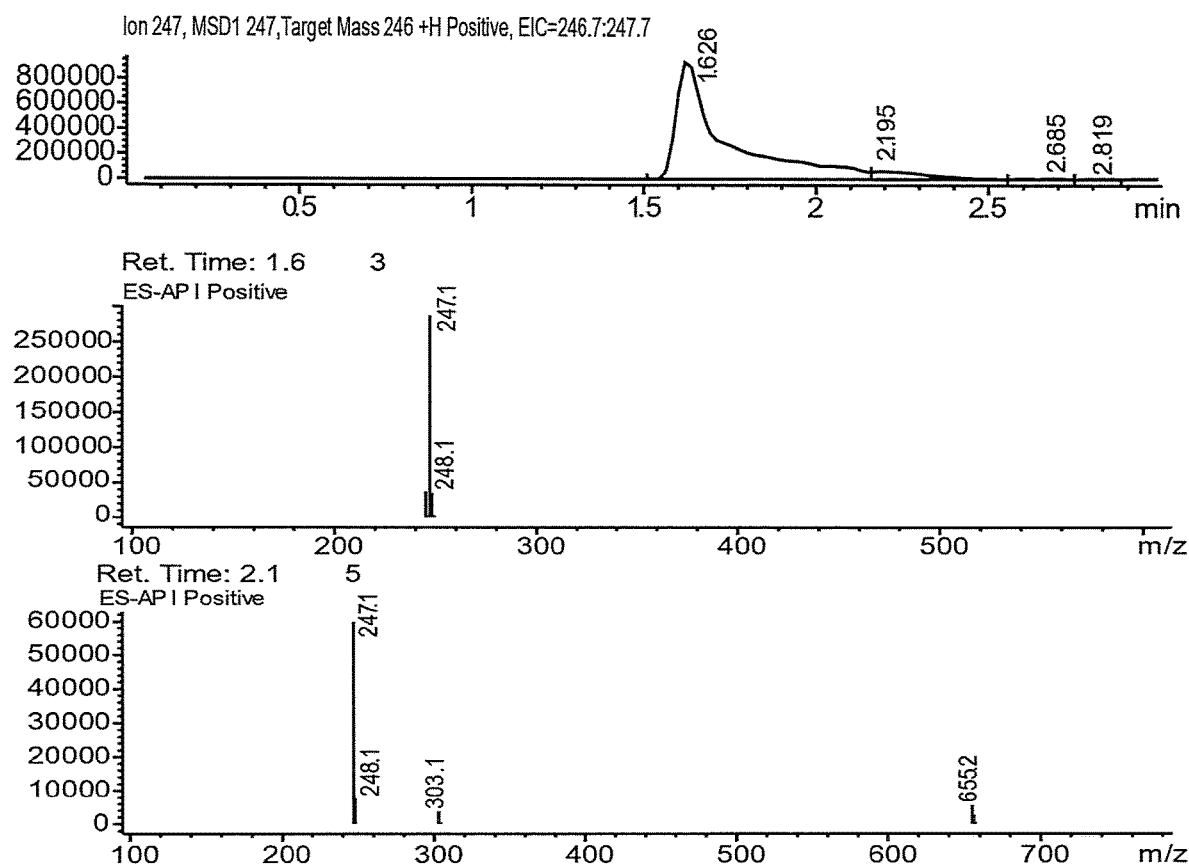
FIG. 1 demonstrates a representative chromatogram and respective mass spectra of two peaks of interest relating to Intermediate 1.

The present invention relates to the use of piperazine and/or piperidine derivatives interacting with VDAC, acting as inhibitors of, inter alia, VDAC oligomerization and the detachment of mitochondrial VDAC1-bound HK.

A critical feature of brain energy metabolism is attachment to the outer mitochondrial membrane (OMM), via binding to VDAC, of hexokinase-I and hexokinase (HK-I and HK-II, respectively), initial and rate-limiting enzymes of glycolysis. HK-I and HK-II attachment to the OMM greatly enhances their enzymatic activity and couples cytosolic glycolysis to mitochondrial oxidative phosphorylation, through which the cell produces most of its adenosine triphosphate (ATP). Mitochondrial attachment of HK-I or HK-II is also important to the survival of neurons and other cells through prevention of apoptosis and oxidative damage.

The present invention discloses for the first time the use of piperazine- and piperidine-derivatives of Formula (I) for treating central nervous system (CNS) disease, particularly psychotic disorders, mood disorders and neurodegenerative diseases. Without wishing to be bound by certain specific theory or mechanism of action, inhibition of mitochondrial HK-1 and/or HK-II by the compounds of the invention leads to normal energy metabolism within brain and neuronal cells, which contributes to prevention or reduction of symptoms of CNS-associated diseases.

Mitochondrial bound HK-I and HK-II also protects against apoptosis and release of reactive oxygen species (ROS) from the mitochondria to the cytosol.

HK-I and HK-II bound to the mitochondria are less sensitive to inhibition by their product glucose-6-phosphate.

Definitions

The term "VDAC" as used herein, unless the context explicitly dictates otherwise, refers to Voltage-Dependent Anion Channel proteins of a highly conserved family of mitochondrial porins. The term refers to all VDAC isoforms, e.g. to isoform VDAC1, to isoform VDAC2, or to isoform VDAC3.

The terms "hexokinase" or "HK", as used herein, unless the context explicitly dictates otherwise, refer to hexokinase enzyme, to all its isoforms, e.g. to isoform HK-I, and HK-II, HK-III and HK-IV. Hexokinase isoforms may also refer to herein as HK-1 HK-2, HK-3 and HK-4.

The terms "central nervous system (CNS) disease", "CNS disorder" "CNS-associated disease or "CNS associated disorder" are used herein interchangeably and refer to one of a group of neurological disorders that affect the structure or function of the brain or spinal cord, which collectively form the central nervous system. According to certain embodiments, the CNS disease is selected from the group consisting of psychotic disorders, mood disorder and neurodegenerative disease. According to some embodiments, the psychotic disorder is schizophrenia. According to some embodiments, the mood disorder is selected from the group consisting of bipolar disorder, depressive disorder and anxiety disorder. According to some embodiments, the neurodegenerative disease is selected from the group consisting of Alzheimer disease and Parkinson disease.

As used herein, the term "schizophrenia" refers to a chronic debilitating disorder, characterized by a spectrum of psychopathology, including positive symptoms such as aberrant or distorted mental representations (e.g., hallucinations, delusions), negative symptoms characterized by diminution of motivation and adaptive goal-directed action (e.g., anhedonia, affective flattening, avolition), and cognitive impairment.

"Mood disorder" as used herein refers to a group of diagnoses in the Diagnostic and Statistical Manual of Mental Disorders (DSM) classification system where a disturbance in the person's mood is hypothesized to be the main underlying feature. The classification is known as mood (affective) disorders in International Classification of Diseases (ICD). Mood disorders fall into the basic groups of elevated mood, such as mania or hypomania; depressed mood, of which the best-known and most researched is major depressive disorder (MDD) (commonly called clinical depression, unipolar depression, or major depression); and moods which cycle between mania and depression, known as bipolar disorder (BD). There are several sub-types of depressive disorders or psychiatric syndromes featuring less severe symptoms such as dysthymic disorder (similar to but milder than MDD) and cyclothymic disorder (similar to but milder than BD). Mood disorders may also be substance-induced or occur in response to a medical condition.

The terms "bipolar disorder", "manic-depressive disorder" "bipolarism" or "manic depression" refer to a psychiatric diagnosis that describes a category of mood disorders defined by the presence of one or more episodes of abnormally elevated mood clinically referred to as mania or, if milder, hypomania. Individuals who experience manic episodes also commonly experience depressive episodes or symptoms, or mixed episodes in which features of both mania and depression are present at the same time. These episodes are usually separated by periods of "normal" mood, but in some individuals, depression and mania may rapidly alternate, known as rapid cycling. Extreme manic episodes can sometimes lead to psychotic symptoms such as delusions and hallucinations. The disorder has been subdivided into bipolar I, bipolar II, cyclothymia, and other types, based on the nature and severity of mood episodes experienced; the range is often described as the bipolar spectrum. The term "mania" or "manic periods" or other variants refers to periods where an individual exhibits some or all of the following characteristics: racing thoughts, rapid speech, elevated levels of activity and agitation as well as an inflated sense of self-esteem, euphoria, poor judgment, insomnia, impaired concentration and aggression.

The term "depression" as used herein includes, but is not limited to, major depressive episodes in the context of major depressive disorder or bipolar disorder, schizoaffective disorder and other psychiatric states that are characterized by depressed mood and/or feelings of sadness, despair, discouragement, "blues", melancholy, feelings of low self-esteem, guilt and self-reproach, withdrawal from interpersonal contact, and somatic symptoms such as eating and sleep disturbances. Depression may be also associated with other psychiatric disorders, with general medical conditions or with alcohol or drug abuse. Examples of other conditions that may be associated with depression include, but are not limited to, dysthymia, posttraumatic stress disorder, schizophrenia, post-partum depression, eating disorders including anorexia nervosa and bulimia, anxiety disorders, Parkinson's disease, Alzheimer's disease, fibromyalgia and chronic fatigue syndrome.

Anxiety disorders include, but are not limited to, obsessive compulsive disorder, generalized anxiety disorder, panic disorder and social phobia.

As used herein, the terms "Alzheimer disease", "Alzheimer's disease" and "AD" are used herein interchangeably, and refer to all types and stages of the disease including pre-clinical and prodromal stages; also known as "dementia of the Alzheimer type. Alzheimer's disease is characterized by memory deficits in its early phase. Later symptoms include impaired judgment, disorientation, confusion, behavior changes, trouble speaking, and motor deficits. Histologically, AD is characterized by beta-amyloid plaques and tangles of protein tau.

The terms "Parkinson's disease" or PD refer to a disease that belongs to a group of chronic and progressive conditions called movement disorders. PD is characterized by muscle rigidity, tremor, a slowing of physical movement (bradykinesia) and, in extreme cases, a loss of physical movement (akinesia). The primary symptoms are the results of decreased stimulation of the motor cortex by the basal ganglia, normally caused by the insufficient formation and action of dopamine, which is produced in the dopaminergic neurons of the brain. Secondary symptoms may include high level cognitive dysfunction and subtle language problems.

The terms "Amyotrophic lateral sclerosis" and "ALS" refer to a progressive, fatal, neurodegenerative disease characterized by a degeneration of motor neurons, the nerve cells in the central nervous system that control voluntary muscle movement. ALS is also characterized by neuronal degeneration in the entorhinal cortex and hippocampus, memory deficits, and neuronal hyperexcitability in different brain areas such as the cortex.

As used herein, the terms "inhibition" or "inhibiting" with regard to inhibiting the detachments of mitochondrial VDAC-bound HK refer to inhibiting the detachment of HK from the mitochondrial VDAC such that HK amount in a cell cytosol is reduced upon administering of a compound of the invention compared to its amount in a corresponding cell without addition of the compound. According to certain embodiments, the cytosolic HK amount is reduced by at least 5%, 10%, 20%, 30%, 40%, 50%, 60%, 70%, 80%, 90%, 95%, 99% or 100% compared to its amount in a corresponding cell with the addition of an inhibitory compound. Each possibility represents a separate embodiment of the present invention.

The term "therapeutically effective amount" as used herein with regard to a compound of the invention is an amount of a compound that, when administered to a subject will have the intended therapeutic effect, e.g. improving symptom(s) associated with a CNS disorder. The full therapeutic effect does not necessarily occur by administering of one dose, and may occur only after administering of a series of doses. Thus, a therapeutically effective amount may be administered in one or more doses. The precise effective amount needed for a subject will depend upon, for example, the subject's weight, health and age, the nature of the CNS disorder and extent of the symptoms of the specific CNS disorder (such as schizophrenia and additional psychotic disorders, bipolar disorder and additional mood disorders, Alzheimer's Disease (AD) and Parkinson's), and optionally, the combination of the compounds of the invention with additional therapeutics, and the mode of administered.

The term "preventing" as used herein means causing the clinical symptoms of the disease state not to develop in a subject that may be exposed to or predisposed to the disease state, but does not yet experience or display symptoms of the disease state.

The term "treating: as used herein refers to inhibiting the disease state, i.e., arresting the development of the disease state or its clinical symptoms, or relieving the disease state, i.e., causing temporary or permanent regression of the disease state or its clinical symptoms. The term is interchangeable with any one or more of the following: abrogating, ameliorating, inhibiting, attenuating, blocking, suppressing, reducing, halting, alleviating or preventing symptoms associated with the disease.

According to one aspect, the present invention provides a method for treating CNS-associated disorder, the method comprising administering to a subject in need thereof at least one substituted piperazine- and piperidine-derivative of general Formula (I):

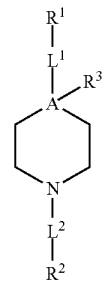

Formula (I)

wherein:

A is carbon (C) or nitrogen (N);

$R^3$ is absent, a hydrogen, an unsubstituted or substituted amide or a heteroalkyl group comprising 3-12 atoms apart from hydrogen atoms, wherein at least one of said 3-12 atoms is a heteroatom, selected from nitrogen, sulfur and oxygen; wherein when A is nitrogen (N), $R^3$ is absent;

$L^1$ is absent or is an amino linking group —$NR^4$—, wherein $R^4$ is hydrogen, a $C_{1-5}$-alkyl, a $C_1$-s-alkylene or a substituted alkyl —$CH_2R$, wherein R is a functional group selected from the group consisting of hydrogen, halo, haloalkyl, cyano, nitro, hydroxyl, alkyl, alkenyl, aryl, alkoxyl, aryloxyl, aralkoxyl, alkylcarbamido, arylcarbamido, amino, alkylamino, arylamino, dialkylamino, diarylamino, arylalkylamino, aminocarbonyl, alkylaminocarbonyl, arylaminocarbonyl, alkylcarbonyloxy, arylcarbonyloxy, carboxyl, alkoxycarbonyl, aryloxycarbonyl, sulfo, alkylsulfonylamido, alkylsulfonyl, arylsulfonyl, alkylsulfinyl, arylsulfinyl and heteroaryl; preferably $R^4$ is hydrogen;

$R^1$ is an aromatic moiety, preferably phenyl, which may be substituted with one or more of Z;

Z is independently at each occurrence a functional group selected from the group consisting of, hydrogen, halo, haloalkyl, haloalkoxy, perhaloalkoxy or $C_{1-2}$-perfluoroalkoxy, cyano, nitro, hydroxyl, alkyl, alkenyl, aryl, alkoxyl, aryloxyl, aralkoxyl, alkylcarbamido, arylcarbamido, amino, alkylamino, arylamino, dialkylamino, diarylamino, arylalkylamino, aminocarbonyl, alkylaminocarbonyl, arylaminocarbonyl, alkylcarbonyloxy, arylcarbonyloxy, carboxyl, alkoxycarbonyl, aryloxycarbonyl, sulfo, alkylsulfonylamido, alkylsulfonyl, arylsulfonyl, alkylsulfinyl, arylsulfinyl and heteroaryl; preferably Z is $C_{1-2}$-perfluoroalkoxy; preferably $R^1$ is a phenyl and Z is trifluoromethoxy; preferably $R^1$ is a phenyl substituted with one trifluoromethoxy, most preferably at the para position;

$L^2$ is a linking group, such that when A is nitrogen (N), $L^2$ is a group consisting of 4-10 atoms (apart from hydrogen atoms), optionally forming a ring, whereof at least one of the atoms is nitrogen, said nitrogen forming part of an amide group; preferably said linking group is selected from the group consisting of an $C_{4-6}$-alkylamidylene and a pyrrolidinylene, said linking group optionally substituted with one or two of alkyl, hydroxy, oxo or thioxo group; most preferably $L^2$ is selected from butanamidylene, N-methylbutanamidylene, N,N-dimethylbutanamidylene, 4-hydroxybutanamidylene (HO—CH$_2$—C*H—CH$_2$—C(O)NH—, wherein the asterisk denotes attachment point), 4-oxobutanamidylene, 4-hydroxy-N-methylbutanamidylene, 4-oxo-N-methylbutanamidylene, 2-pyrrolidonyl, pyrrolidine-2,5-dionylene, 5-thioxo-2-pyrrolidinonylene and 5-methoxy-2-pyrrolidinonylene;

and when A is carbon (C), then $L^2$ is either as defined for $L^2$ when A is nitrogen (N) or $C_{1-4}$ alkylene; $L^2$ is preferably methylene (—CH$_2$—);

$R^2$ is a phenyl or a naphthyl, optionally substituted with halogen, preferably when $R^2$ is a phenyl it is substituted with halogen, preferably chlorine, at the para position, preferably when $R^2$ is naphthyl, $L^2$ is an alkylene group, preferably —CH$_2$—;

with a proviso that when A is carbon (C), $L^1$ is —NR$^4$—, $R^4$ is hydrogen, and $R^2$ is phenyl substituted with chlorine, then $L^2$ is not pyrrolidine-2,5-dione.

In some embodiments, $R^3$ is hydrogen or heteroalkyl group comprising 3-12 atoms apart from hydrogen atoms, wherein at least one of said 3-12 atoms is a heteroatom, selected from nitrogen, sulfur and oxygen. In other embodiments (i.e., when A is nitrogen), $R^3$ is absent.

In some embodiments, $R^4$ is hydrogen.

In some embodiments, $R^1$ is a phenyl substituted trifluoromethoxy. In some embodiments, $R^1$ is a phenyl substituted with one trifluoromethoxy. In some embodiments, $R^1$ is a phenyl substituted with one trifluoromethoxy at the para position. In some embodiments, $R^1$ is phenyl In some embodiments, $L^2$ is a linking group, consisting of 4-10 atoms (apart from hydrogen atoms), optionally forming a ring, whereof at least one of the atoms is nitrogen, said nitrogen forming part of an amide group; preferably said linking group is selected from the group consisting of an $C_{4-6}$-alkylamidylene and a pyrrolidinylene, said linking group optionally substituted with one or two of alkyl, hydroxy, oxo or thioxo group; most preferably $L^2$ is selected from butanamidylene, N-methylbutanamidylene, N,N-dimethylbutanamidylene, 4-hydroxybutanamidylene (HO—CH$_2$—C*H—CH$_2$—C(O)NH— wherein the asterisk denotes attachment point), 4-oxobutanamidylene, 4-hydroxy-N-methylbutanamidylene, 4-oxo-N-methylbutanamidylene, 2-pyrrolidonyl, pyrrolidine-2,5-dionylene, 5-thioxo-2-pyrrolidinonylene and 5-methoxy-2-pyrrolidinonylene; or $L^2$ is $C_{1-4}$ alkylene, preferably methylene (—CH$_2$—);

The term "pyrrolidinylene" refers to a pyrrolidine ring as a bivalent substituent. Pyrrolidinylene include unsubstituted and substituted rings, such as, but not limited to, pyrrolidine-2-5-dione, 2-pyrrolidinone, 5-thioxo-2-pyrrolidinone, 5-methoxy-2-pyrrolidinone and the like.

In one embodiment, when A is nitrogen (N), the linking group $L^2$ is selected from the group consisting of an $C_{4-6}$-alkylamidylene and a pyrrolidinylene, said linking group optionally substituted with one or two of alkyl, hydroxy, oxo or thioxo group. For example, $L^2$ may be butanamidylene, N-methylbutanamidylene, N,N-dimethylbutanamidylene, 4-hydroxybutanamidylene, 4-oxobutanamidylene, 4-hydroxy-N-methylbutanamidylene, 4-oxo-N-methylbutanamidylene, 2-pyrrolidonyle, pyrrolidine-2,5-dionylene, 5-thioxo-2-pyrrolidinonylene or 5-methoxy-2-pyrrolidinonylene. Preferably, when $L^2$ is butanamidylene, N-methylbutanamidylene, N,N-dimethylbutanamidylene, 4-hydroxybutanamidylene, 4-oxobutanamidylene, 4-hydroxy-N-methylbutanamidylene or 4-oxo-N-methylbutanamidylene, then preferably the carbon in third position (C) of the butanamide moiety is bonded to the nitrogen (N) of the piperazine ring or the piperidine ring and the nitrogen (N) of the butanamide moiety is bonded to $R^2$. For example, when $L^2$ is 2-pyrrolidone, pyrrolidine-2,5-dione, 5-thioxo-2-pyrrolidone or 5-methoxy-2-pyrrolidone, then preferably a carbon (C) of the pyrrolidine moiety is bonded to the nitrogen (N) of the piperazine ring or the piperidine ring and the nitrogen (N) of the pyrrolidine moiety is bonded to $R^2$.

In another embodiment, A is carbon (C), $R^3$ is heteroalkyl and $L^2$ is methylene.

The invention also relates to the stereoisomers, enantiomers, mixtures thereof, and salts, particularly the physiologically acceptable salts, of the compounds of general Formula (I) according to the invention.

According to certain embodiments, the at least one substituted piperazine- and piperidine-derivative is of general Formula Ia:

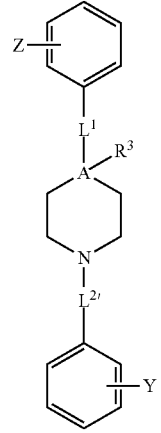

Formula (Ia)

wherein:
A, $R^3$, Z and $L^1$ are as previously defined in reference to compound of Formula (I); preferably A is nitrogen (N);

$L^{2'}$ is a linking group selected from the group consisting of an $C_4$-alkylamidylene, $C_5$-alkylamidylene and $C_6$-alkylamidylene, optionally substituted with one or two of alkyl, hydroxy, oxo or thioxo group; preferably $L^{2'}$ is selected from butanamidylene, N-methylbutanamidylene, N,N-dimethylbutanamidylene, 4-hydroxybutanamidylene, 4-oxobutanamidylene, 4-hydroxy-N-methylbutanamidylene or 4-oxo-N-methylbutanamidylene; most preferably $L^{2'}$ is 4-hydroxybutanamidylene; wherein preferably the carbon (C) at position 3 of the alkyl moiety of alkylamidylene $L^{2'}$ is bonded to the nitrogen (N) of the piperazine ring or of the piperidine ring, and the nitrogen (N) of the butanamide moiety is bonded to the phenyl group; preferably $L^{2'}$ is HO—$CH_2$—C*H—$CH_2$—C(O)NH—, wherein the asterisk denotes attachment point;

Y is halogen, preferably chlorine, e.g. at the para position; or an enantiomer, diastereomer, mixture or salt thereof.

According to certain embodiments, the substituted piperazine- and piperidine-derivative is of general Formula (Ib):

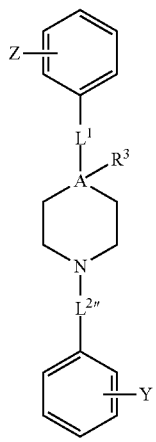

Formula (Ib)

wherein:

A, $R^3$, and Z are as previously defined in reference to the compound of Formula (I); preferably A is nitrogen (N);

$L^1$ is absent;

$L^{2''}$ is a pyrrolidinylene linking group, optionally substituted with one or two of alkyl, hydroxy, oxo or thioxo group, preferably $L^{2''}$ is selected from 2-pyrrolidonylene, pyrrolidine-2,5-dionylene, 5-thioxo-2-pyrrolidinonylene and 5-methoxy-2-pyrrolidinonylene; most preferably $L^{2''}$ is pyrrolidine-2,5-dionylene; wherein preferably a carbon (C) at position 4 or the carbon (C) at position 3 of the pyrrolidinyl moiety $L^{2''}$ is bonded to the nitrogen (N) of the piperazine ring or the piperidine ring and the nitrogen (N) of the pyrrolidinyl moiety is bonded to the phenyl group substituted with Y; and Y is halogen, preferably chlorine, e.g. at the para position.

According to certain embodiments, the substituted piperazine- and piperidine-derivative is of general Formula (Ic):

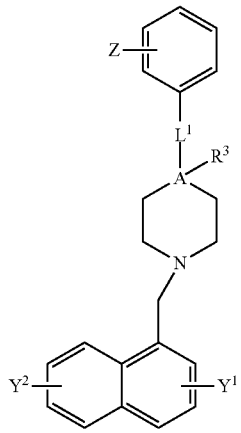

Formula (Ic)

wherein:

A, $R^3$, and Z are as previously defined in reference to the compounds of general Formula (I);

$L^1$ is —NH—; and $Y^1$ and $Y^2$ are each independently absent or a halogen;

or an enantiomer, diastereomer, mixture or salt thereof.

Preferred compounds of Formula (Ic) are those wherein $R^3$ is —C(O)NHCH$_2$C(O)OH group, and/or wherein Z is $C_{1-2}$-alkoxy or halogenated $C_{1-2}$-alkoxy, e.g. $C_{1-2}$-perfluoroalkoxy.

According to certain embodiments, the substituted piperazine- and piperidine-derivatives is of general Formula (Id):

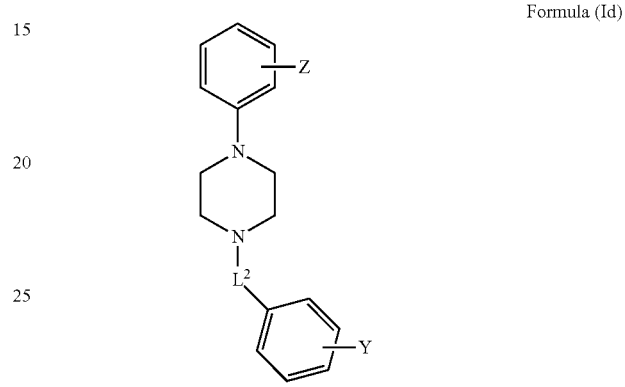

Formula (Id)

wherein $L^2$ is selected from the group consisting of an $C_{4-6}$-alkylamidylene (e.g. HO—$CH_2$—C*H—$CH_2$—C(O)NH—, wherein the asterisk denotes attachment point), and a pyrrolidinylene (e.g. pyrrolidin-2,5-dionylene), optionally substituted with one or two of alkyl, hydroxy, oxo or thioxo group; and Z is haloalkoxy, e.g. $C_{1-2}$-perfluoroalkoxy, and Y is halogen.

The invention also relates to the stereoisomers, enantiomers, mixtures thereof and salts thereof, of the compounds of general Formulae (Ia), (Ib), (Ic), and (Id), according to the invention.

Table 1 provides non-limiting examples of compound of general Formula (I). It includes compounds as follows:

N-(4-chlorophenyl)-4-hydroxy-3-(4-(4-(trifluoromethoxy)phenyl)-piperazin-1-yl)butanamide (Formula 1);

1-(4-chlorophenyl)-3-(4-(4-(trifluoromethoxy)phenyl)piperazin-1-yl)pyrrolidine-2,5-dione (Formula 2);

1-(naphthalen-1-yl)methyl)-4-(phenylamino)-piperidine-4-carbonyl)glycine (Formula 3);

1-(4-chlorophenyl)-3-(4-(4-(trifluoromethoxy)phenyl)piperazin-1-yl)pyrrolidin-2-one (Formula 4);

1-(4-chlorophenyl)-5-thioxo-3-(4-(4-(trifluoro-methoxy)phenyl)piperazin-1-yl)pyrrolidin-2-one (Formula 5);

1-(4-chlorophenyl)-5-methoxy-4-(4-(4-(trifluoromethoxy)phenyl)-piperazin-1-yl)pyrrolidin-2-one (Formula 6);

1-(4-chlorophenyl)-5-thioxo-4-(4-((4-(trifluoromethoxy)phenyl)amino)piperidin-1-yl)pyrrolidin-2-one (Formula 7);

4-(4-chlorophenyl)-4-oxo-3-(4-(4-(trifluoromethoxy)phenyl)piperazin-1-yl)butanamide (Formula 8); and N-(4-chlorophenyl)-4-hydroxy-N-methyl-3-(4-(4-(trifluoromethoxy)phenyl)piperazin-1-yl)butanamide (Formula 9).

TABLE 1 examples of compound of general Formula (I)

| Formula # | Structure | Description (according to general Formula (I)) |
|---|---|---|
| 1 | 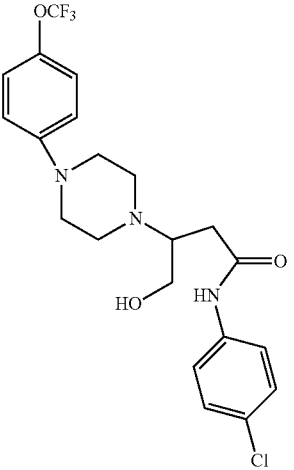 [SMILES: O=C(CC(CO)N1CCN(c2ccc(OC(F)(F)F)cc2)CC1)Nc1ccc(Cl)cc1] | A is nitrogen (N), $R^3$ is absent, $L^1$ is absent, $R^1$ is phenyl substituted with one trifluoromethoxy, $L^2$ is 4-hydroxybutanamidylene, the $3^{rd}$ carbon (C) of the butanamide moiety is bonded to the nitrogen (N) of the piperazine ring, the nitrogen (N) of the butanamide moiety is bonded to $R^2$ and $R^2$ is a phenyl substituted with chlorine at the para position [also identified herein as VBIT-4 or as BGD-4] |
| 2 | 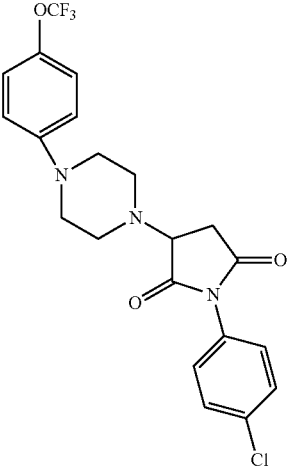 [SMILES: O=C1CC(N2CCN(c3ccc(OC(F)(F)F)cc3)CC2)C(=O)N1c1ccc(Cl)cc1] | A is nitrogen (N), $R^3$ is absent, $L^1$ is absent, $R^1$ is phenyl substituted with one trifluoromethoxy, $L^2$ is pyrrolidine-2,5-dione, the carbon (C) at position 3 of the pyrrolidine moiety is bonded to the nitrogen (N) of the piperazine ring, the nitrogen (N) of the pyrrolidine moiety is bonded to $R^2$ and $R^2$ is a phenyl substituted with chlorine at the para position [also identified herein as VBIT-3 or as BGD-3] |
| 3 | 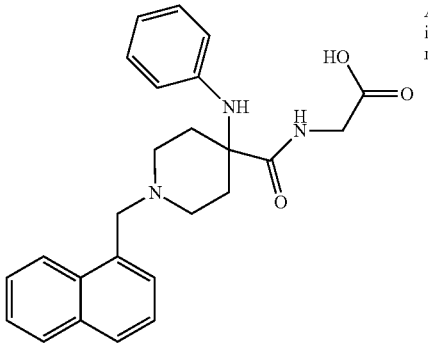 | A is carbon (C), $R^3$ is C(O)NHCH$_2$C(O)OH group; $L^1$ is —NH—, $R^1$ is a phenyl, $L^2$ is methylene and $R^2$ is a naphthyl [also identified herein as VBIT-12] |

TABLE 1-continued examples of compound of general Formula (I)

| Formula # | Structure | Description (according to general Formula (I)) |
|---|---|---|
| 4 | 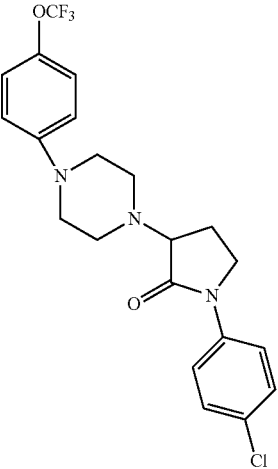 [SMILES: O=C1C(N2CCN(c3ccc(OC(F)(F)F)cc3)CC2)CCN1c1ccc(Cl)cc1] | A is nitrogen (N), $R^3$ is absent, $L^1$ is absent, $R^1$ is a phenyl substituted with one trifluoromethoxy; $L^2$ is 2-pyrrolidone, the carbon (C) at position 3 of the pyrrolidone moiety is bonded to the nitrogen (N) of the piperazine ring, the nitrogen (N) of the pyrrolidone moiety is bonded to $R^2$ and $R^2$ is a phenyl substituted with chlorine at the para position [also identified herein as VBIT-5] |
| 5 | 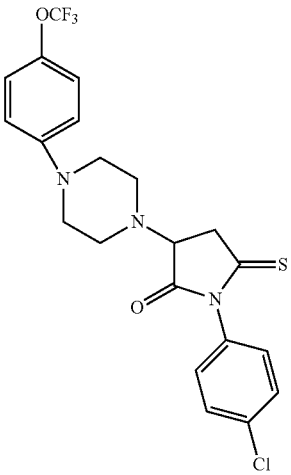 [SMILES: O=C1C(N2CCN(c3ccc(OC(F)(F)F)cc3)CC2)CC(=S)N1c1ccc(Cl)cc1] | A is nitrogen (N), $R^3$ is absent, $L^1$ is absent, $R^1$ is a phenyl substituted with one trifluoromethoxy, $L^2$ is 5-thioxo-2-pyrrolidone, the carbon (C) at position 3 of the pyrrolidine moiety is bonded to the nitrogen (N) of the piperazine ring, the nitrogen (N) of the pyrrolidine moiety is bonded to $R^2$ and $R^2$ is a phenyl substituted with chlorine at the para position [also identified herein as VBIT-6] |
| 6 | 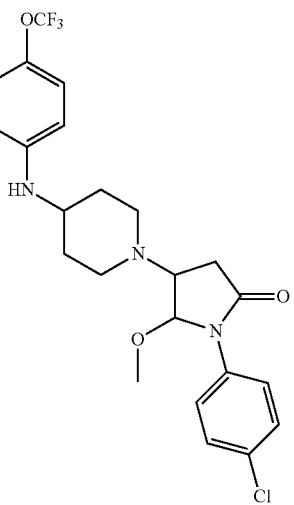 | A is carbon (C), $R^3$ is hydrogen, $L^1$ is —NH—, $R^1$ is a phenyl substituted with one trifluoromethoxy, $L^2$ is 5-methoxy-2-pyrrolidinone, the carbon (C) at position 4 of the pyrrolidine moiety is bonded to the nitrogen (N) of the piperidine ring, the nitrogen (N) of the pyrrolidine moiety is bonded to $R^2$ and $R^2$ is a phenyl substituted with chlorine at the para position [also identified herein as VBIT-9] |

TABLE 1-continued examples of compound of general Formula (I)

| Formula # | Structure | Description (according to general Formula (I)) |
|---|---|---|
| 7 | 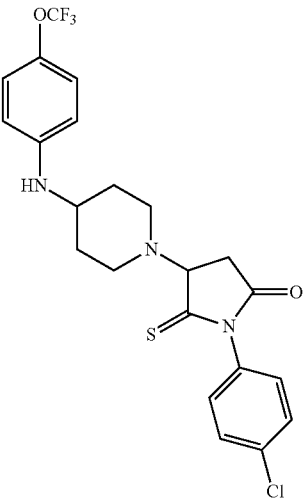 [SMILES: O=C1CC(N2CCC(Nc3ccc(OC(F)(F)F)cc3)CC2)C(=S)N1c1ccc(Cl)cc1] | A is carbon (C), $R^3$ is hydrogen, $L^1$ is —NH—, $R^1$ is a phenyl substituted with one trifluoromethoxy, $L^2$ is 5-thioxo-2-pyrrolidone, the carbon (C) at position 3 of the pyrrolidine moiety is bonded to the nitrogen (N) of the piperidine ring, the nitrogen (N) of the pyrrolidine moiety is bonded to $R^2$ and $R^2$ is a phenyl substituted with chlorine at the para position [also identified herein as VBIT-10] |
| 8 | 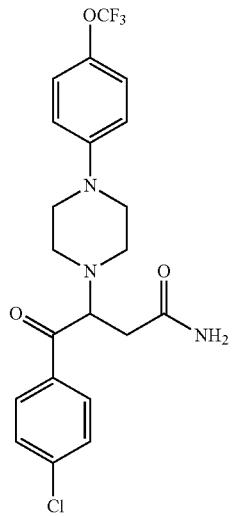 [SMILES: NC(=O)CC(C(=O)c1ccc(Cl)cc1)N1CCN(c2ccc(OC(F)(F)F)cc2)CC1] | A is nitrogen (N), $R^3$ is absent, $L^1$ is absent, $R^1$ is phenyl substituted with one trifluoromethoxy, $L^2$ is 4-oxobutanamide, the $3^{rd}$ carbon (C) of the butanamide moiety is bonded to the nitrogen (N) of the piperazine ring, the $4^{th}$ carbon (C) of the butanamide moiety is bonded to $R^2$ and $R^2$ is a phenyl substituted with chlorine at the para position [also identified herein as VBIT-7] |
| 9 | 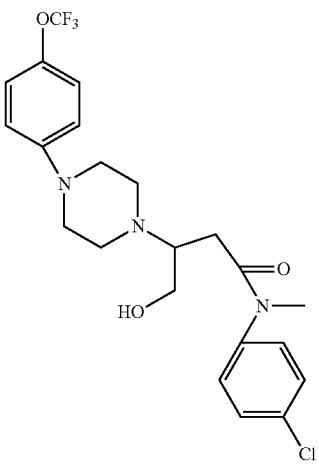 [SMILES: CN(C(=O)CC(CO)N1CCN(c2ccc(OC(F)(F)F)cc2)CC1)c1ccc(Cl)cc1] | A is nitrogen (N), $R^3$ is absent, $L^1$ is absent, $R^1$ is phenyl substituted with one trifluoromethoxy, $L^2$ is 4-hydroxy-N-methylbutanamide, the $3^{rd}$ carbon (C) of the butanamide moiety is bonded to the nitrogen (N) of the piperazine ring, the nitrogen (N) of the butanamide moiety is bonded to $R^2$ and $R^2$ is a phenyl substituted with chlorine at the para position [also identified herein as VBIT-8] |

Some terms used herein to describe the compounds according to the invention are defined more specifically below.

The term halogen denotes an atom selected from among F, Cl, Br and I, preferably Cl and Br.

The term heteroalkyl as used herein in reference to $R^3$ moiety of the general Formulae (I), (Ia), (Ib), (Ic), (Id), and (IIa), refers to a saturated or unsaturated group of 3-12 atoms (apart from hydrogen atoms), wherein one or more (preferably 1, 2 or 3) atoms are a nitrogen, oxygen, or sulfur atom, for example an alkyloxy group, as for example methoxy or ethoxy, or a methoxymethyl-, nitrile-, methylcarboxyalkylester- or 2,3-dioxyethyl-group; preferably heteroalkyl group is a chain comprising an alkylene, and at least one of a carboxylic acid moiety, a carbonyl moiety, an amine moiety, a hydroxyl moiety, an ester moiety, an amide moiety. The term heteroalkyl refers furthermore to a carboxylic acid or a group derived from a carboxylic acid as for example acyl, acyloxy, carboxyalkyl, carboxyalkylester, such as for example methylcarboxyalkylester, carboxyalkylamide, alkoxycarbonyl or alkoxycarbonyloxy; preferably the term refers to —C(O)NHCH$_2$C(O)OH group.

The term $C_{1-n}$-alkyl, wherein n may have a value as defined herein, denotes a saturated, branched or unbranched hydrocarbon group with 1 to n carbon (C) atoms. Examples of such groups include methyl, ethyl, n-propyl, iso-propyl, butyl, iso-butyl, sec-butyl, tert-butyl, n-pentyl, iso-pentyl, neo-pentyl, tert-pentyl, n-hexyl, iso-hexyl, etc.

The term $C_{1-4}$-alkyl denotes a saturated, branched or unbranched hydrocarbon group with 1 to 4 carbon (C) atoms.

The term $C_{1-n}$-alkoxy, wherein n may have a value as defined herein, denotes an alkyl group as defined herein, bonded via —O— (oxygen) linker.

The term "$C_{1-n}$ alkylene", wherein n may have a value as defined herein, denotes an alkylene group of saturated hydrocarbons substituents with the general formula $C_nH_{2n}$. Generally, n is a positive integer. For example, $C_1$ alkylene refers to methylene (—CH$_2$—), $C_3$ alkylene refers to $C_3H_6$, which may be n-propylene (—CH$_2$CH$_2$CH$_2$—) or isopropylene (—CH(CH$_3$)CH$_2$— or —CH$_2$CH(CH$_3$)—). Preferably the term refers to an unbranched n-alkylene.

The term $C_{1-n}$-perfluoroalkoxy, wherein n may have a value as defined herein, denotes an alkoxy group with hydrogen atoms substituted by fluorine atoms.

The term $C_{1-m}$-alkylamidyl, wherein m may have a value as defined herein, denotes a group comprising 1 to m carbon (C) atoms and an amide group formed by either $C_{m-a}$alkyl-COOH and H$_2$N-C$_a$alkyl, or $C_{m-a}$alkyl-NH$_2$ and HOOC—C$_a$alkyl, wherein a is smaller than or equal to m. Similarly, the terms $C_4$-alkylamidylene, $C_5$-alkylamidylene and $C_6$-alkylamidylene refer to divalent $C_m$-alkylamidyl groups, wherein m is either 4, 5, or 6, respectively.

Certain compounds of the general Formula (I), wherein $L^1$ is absent, and A is nitrogen, may be prepared by coupling an aryl halide of the formula $R^1$—X, wherein X is a halogen, preferably bromide, with a mono-protected piperazine, e.g. with BOC-protected piperazine, and upon deprotection, reacting with a $L^2$-linker precursor reactive with secondary amines, and subsequent amidation or transamidation of the $L^2$-linker precursor moiety with a suitable amine of the formula (Y)$R^2$—NH$_2$. The $L^2$-linker precursor may be an unsaturated $C_{4-6}$ carboxylic derivative compound, e.g. an unsaturated $C_{4-6}$ lactone, or a β-, γ-, δ- or ε-unsaturated linear ester of the $C_{4-6}$ carboxylic acid and a suitable alcohol, e.g. $C_{1-6}$ alcohol. Alternatively, the deprotected $R^1$-piperazine may be reacted with a suitable N—$R^2$-pyrrolidenone or N—$R^2$-pyrrolidinene-dione, prepared by generally known methodology (e.g. in Synthesis, anticonvulsant activity and 5-HT1A, 5-HT2A receptor affinity of new N-[(4-arylpiperazin-1-yl)-alkyl] derivatives of 2-azaspiro[4.4]nonane and [4.5]decane-1,3-dione, by Obniska, J et al. 2006. European Journal of Medicinal Chemistry 41(7), 874-881).

Compounds of general Formulae (Ia) and (Ib) may be prepared according to a Method (a) shown in Schemes 1 to 3, starting from a compound of general Formula A, wherein Z is as hereinbefore defined.

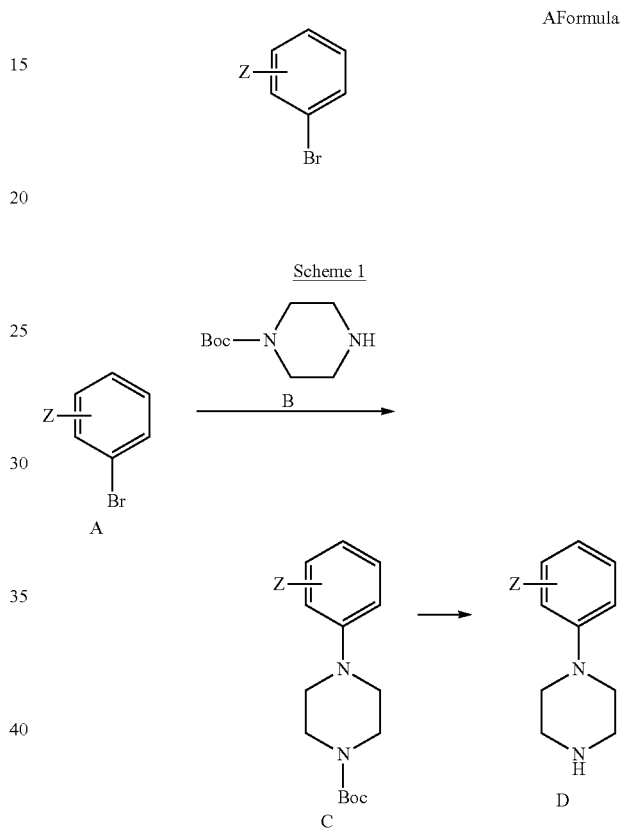

Compounds of general Formula C are obtained by reacting a compound of general Formula A with a piperazine in which one of the nitrogens is protected with a protecting group, e.g. tert-butyloxycarbonyl protecting group (BOC group). The starting compounds of general Formula A is either commercially obtainable or may be prepared by using known methods from commercially obtainable compounds. The carbon-nitrogen (C—N) coupling reaction is carried out in the presence of a palladium catalyst, such as tris(dibenzylideneacetone)dipalladium (Pd$_2$(dba)$_3$) that is particularly suitable. The reaction is carried out in a presence of a bidentate phosphine ligand and a base. Suitable bidentate phosphine ligands are diphenyl-phosphinobinapthyl (BINAP) and diphenylphosphinoferro-cene (DPPF), while BINAP is particularly preferred. Suitable bases include sodium tert-butoxide, potassium tert-butoxide, lithium bis(trimethylsilyl)-amide, while sodium tert-butoxide is particularly suitable. The reaction is carried out in a suitable aprotic solvent such as toluene, tetrahydrofuran (THF), dioxane, but preferably toluene, under nitrogen atmosphere, and at a temperature between 55° C. and 110° C., preferably at a temperature of 65° C. and 110° C., most preferably 80° C. and 110° C. Upon completion of the reaction the solvent is evaporated to provide crude compound of Formula C as a residue that may be used for the next step without further purification.

Compounds of general Formula D are obtained by removal of the protecting group, e.g. BOC, in the compound of general Formula C, which can be accomplished with strong acids such as trifluoroacetic acid, neat or in dichloromethane, or with concentrated HCl in methanol or in dichloromethane (DCM), while concentrated HCl in DCM is preferred. The reaction is preferably carried out at room temperature. Upon completion of the reaction the organic phase is discarded and the aqueous phase evaporated to dryness. The residue is dissolved in a base and a suitable solvent, such as DCM, dichloroethane or 2-methyltetrahydrofuran (MeTHF), NaOH (2.0 M) and DCM are preferred. Upon completion of the reaction, the organic solvent phase, e.g. DCM, is collected and concentrated to yield the crude product of general Formula D that may be used for the next step without further purification.

Compounds of general Formula (Ia) and (Ib) are obtained from compounds of general Formula D. For example, certain preferred compounds of general Formula (Ia) may be obtained according to Scheme 2, by reacting a compound of general Formula D with a suitable lactone, e.g. 2-furanone, to yield a compound of general Formula E, which is reacted with a suitable aminophenyl to yield a compound of general Formula (Ia).

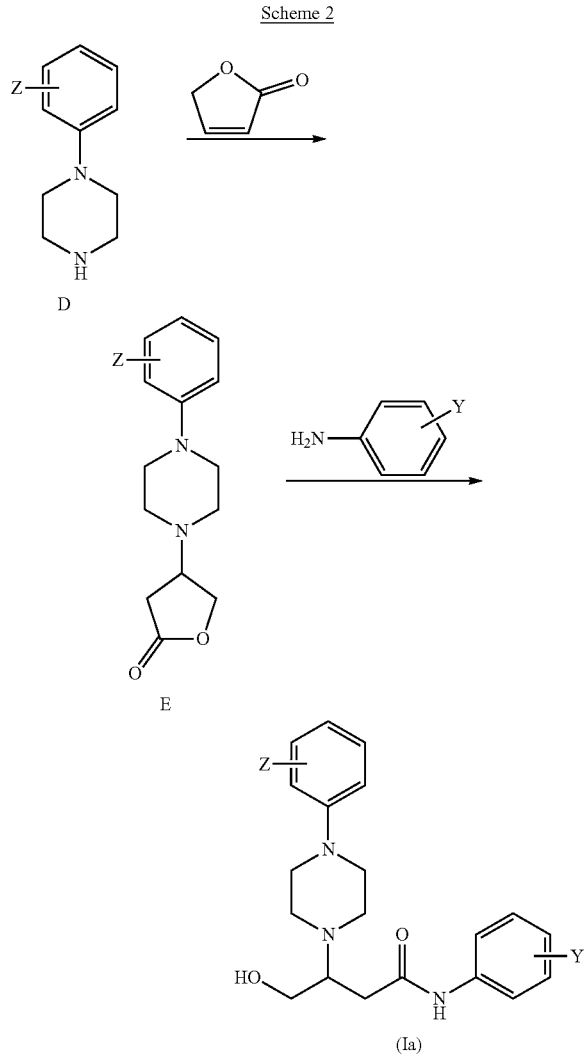

For example, certain preferred compounds of general Formula (Ib) may be obtained according to Scheme 3, by reacting a compound of general Formula D with a suitable pyrrole-dione, e.g 1-Phenyl-1H-pyrrole-2,5-dione, which is commercially available or may readily be prepared by methods familiar to those skilled in the art, to yield a compound of general Formula (Ib).

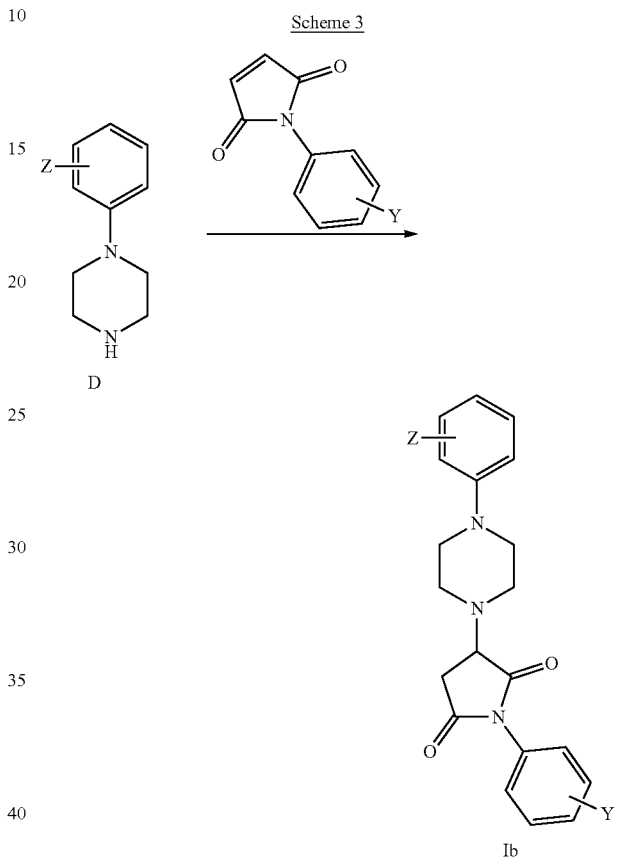

Certain compounds of the general Formula (I) wherein $R^3$ is present and is not hydrogen and wherein $L^1$ is present, can be prepared from halogenated compounds of the general formula $(Y^1)(Y^2)R^2$-$L^2$-X that are coupled with a protected piperidone in presence of a base, and the recovered ketone is $R^3$-sililated, e.g. nitrilosililated, in presence of an amine of the general formula $R^1$-$L^1$-H ($L^1$-H being the —$NR^4$— group, with $R^4$ as defined hereinabove) in acid environment to furnish the compound of general formula $(Y^1)(Y^2)R^2$-$L^2$-N[—$CH_2$—$CH_2$—]$_2$C($R^3$)$L^1$-$R^1$, wherein $R^3$ is the nitrile. Thereafter, the nitrile may be hydrolyzed in a strong acid to a respective amide and further in a strong base to a respective carboxylic acid, which is reacted by peptidic methodology to a protected glycinate ester, finally deprotected to furnish the compound of formula (I).

Certain preferred compounds of general Formula (Ic) may be prepared according to a Method (b) shown in Schemes 4 and 4a, starting from a naphthyl compound of general Formula F, wherein X is halogen, preferably chlorine, p is an integer having a value of 1, 2 or 3 and $Y^1$ and $Y^2$ are as hereinbefore defined.

Scheme 4

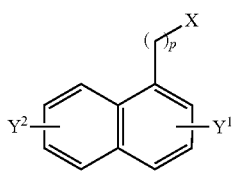

the ketone. The reaction is carried out in a polar solvent, such as dimethyl formamide (DMF) or tetrahydrofuran (THF), in presence of a base. Suitable base may be a carbonate, e.g. potassium carbonate, sodium carbonate. The reaction may be carried out at a temperature between 0° C. and 60° C., preferably between 15° C. and 40° C., most preferably at ambience, e.g. at room temperature. The reaction may be kept for about 6-18 hours, preferably for about 10-14 hours. The product may be purified, e.g. by chromatography, and deprotected by heating the product under acidic conditions. The deprotection may be carried out in a suitable solvent, e.g. an alcohol, such as ethanol, that dissolves the acid used, e.g. hydrochloric acid.

The obtained compound of Formula H may be further reacted with a suitable substituted silane, e.g. trimethyl sililonitrile (TMSCN), in a presence of a suitable primary or secondary amine, e.g. aniline, piperidine, ethylamine, propylamine, ethylpropylamine, dipropylamine, in a suitable solvent under acidic conditions, e.g. in acetic acid, trifluoroacetic acid, benzoic acid. The reagents may be combined at a temperature lower than 60° C., preferably lower than 40° C., further preferably between 0° C. and 40° C. and most preferably between 10° C. and 20° C. The reaction may be kept for about 6-18 hours, preferably for about 10-14 hours. After neutralizing the acid, the reaction mixture may be extracted into an apolar solvent, such as dichloromethane, to yield the nitrile compound of formula J, which may be used without further purification.

The nitrile compounds of formula J may be further converted into the compounds of general Formula (Ic) according to the Scheme 4a below:

Scheme 4a

Generally, compounds of general Formula H are obtained by reacting a compound of general Formula F with a piperidone, preferably 4-piperidone, protected with a suitable glycol, e.g. ethylene glycol, followed by deprotection of

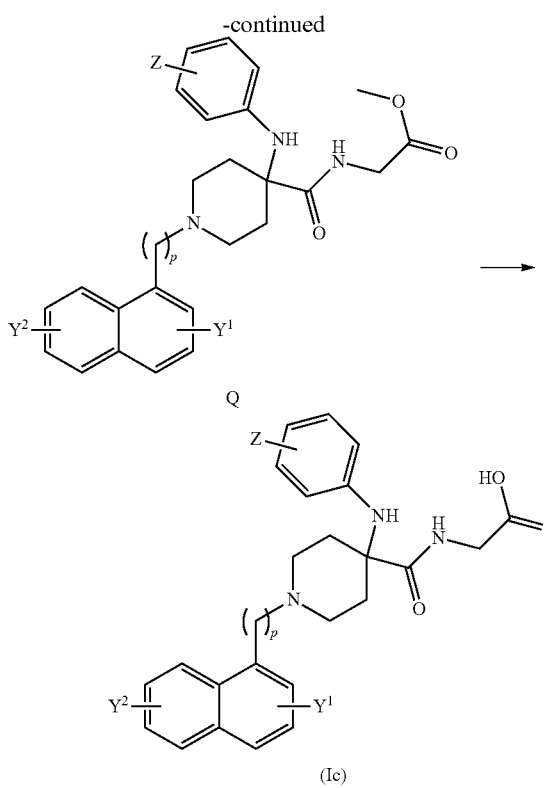

(Ic)

The compound of the formula K is prepared by hydrolyzing the nitrile compound of formula J in a strong acid, e.g. in concentrated sulfuric acid, nitric acid, hydrobromic acid (HBr) and hydrochloric acid (HCl). The reaction may be kept for about 6-18 hours, preferably for about 10-14 hours. After neutralization of the reaction mixture, the compound of the formula K can be purified, e.g. by reverse-phase preparative HPLC.

The compound of the formula K may be further hydrolyzed into the compound of formula N, e.g. with potassium hydroxide in a polar solvent, e.g. in ethylene glycol. The reagents may be combined at a temperature between 110° C. and 170° C. and most preferably between 140° C. and 160° C. The reaction may be kept for about 6-18 hours, preferably for about 10-14 hours. After cooling of the reaction mixture, the compound of the formula N can be purified, e.g. by reverse-phase preparative HPLC. The compound of formula N may then be reacted with methyl glycinate in DMF in presence of a coupling agent, e.g. 1-[Bis(dimethylamino)methylene]-1H-1,2,3-triazolo [4,5-b]-pyridinium-3-oxid hexafluorophosphate (known as HATU) and diisopropyl ethylamine, for about 6-18 hours, preferably for about 10-14 hours, and purified, e.g. by reverse-phase preparative HPLC, to furnish the compound of formula Q. Additional coupling agents that may be used are N,N'-dicyclohexylcarbodiimide (DCC), 3-(ethyliminomethyleneamino)-N,N-dimethylpropan-1-amine (EDC), 3-[bis(dimethylamino)-methyliumyl]-3H-benzotriazol-1-oxide hexafluorophosphate (HBTU), 1-[bis(dimethylamino)methylene]-1H-1,2,3-triazolo[4,5-b] pyridinium 3-oxid hexafluorophosphate (HATU), 1-[(1-(cyano-2-ethoxy-2-oxoethyl-ideneaminooxy)-dimethyl-amino-morpholinomethylene)]-methanaminium hexafluorophosphate (COMU).

Finally, the compound of formula Q may be hydrolyzed with a base, e.g. lithium hydroxide, to release the methyl ester and furnish the crude compound of the general Formula (Ic), e.g. in an aprotic solvent, such as tetrahydrofuran, for about 6-18 hours, preferably for about 10-14 hours. The reaction mixture may then be neutralized to pH about 7, and then purified, e.g. by a preparative HPLC, to furnish the compound of the general Formula (Ic).

Compounds of general formula (Id) are prepared according to the method described for the compounds of general formulae (Ia) and (Ib).

In the reactions described hereinabove, any reactive group such as for example an amino, alkylamino, hydroxy or carboxy group, may be protected during the reaction by conventional protecting groups which are cleaved after the reaction, by methods known in the art.

The invention also relates to the stereoisomers, such as diastereomers and enantiomers, mixtures and salts, particularly the physiologically acceptable salts, of the compounds of general Formulae (I), (Ia), (Ib), (Ic), and (Id), and of the compounds of structural formulae 1, 2, 3, 4, 5, 6, 7, 8 and 9.

The compounds of general Formulae (I), (Ia), (Ib), (Ic), and (Id), or intermediate products in the synthesis of compounds of general Formulae (I), (Ia), (Ib), (Ic), and (Id), may be resolved into their enantiomers and/or diastereomers on the basis of their physical-chemical differences using methods known in the art. For example, cis/trans mixtures may be resolved into their cis and trans isomers by chromatography. For example, enantiomers may be separated by chromatography on chiral phases or by recrystallisation from an optically active solvent or by enantiomer-enriched seeding.

The compounds of general Formulae (I), (Ia), (Ib), (Ic), and (Id), and the compounds of structural formulae 1, 2, 3, 4, 5, 6, 7, 8 and 9, may be converted into the salts thereof, particularly physiologically acceptable salts for pharmaceutical use. Suitable salts of the compounds of general Formulae (I), (Ia), (Ib), (Ic), and (Id), and of the compounds of structural formulae 1, 2, 3, 4, 5, 6, 7, 8 and 9, may be formed with organic or inorganic acids, such as, without being limited to hydrochloric acid, hydrobromic acid, sulphuric acid, phosphoric acid, lactic acid, acetic acid, succinic acid, citric acid, palmitic acid or maleic acid. Compounds of general Formulae (I), (Ia), (Ib), (Ic) and (Id), containing a carboxy group, may be converted into the salts thereof, particularly into physiologically acceptable salts for pharmaceutical use, with organic or inorganic bases. Suitable bases for this purpose include, for example, sodium hydroxide, potassium hydroxide, ammonium hydroxide, arginine or ethanolamine.

According to another aspect provided herein are uses of the compounds of general Formulae (I), (Ia), (Ib), (Ic), (Id), and (IIa), such as, without being limited to, the compounds of structural formulae 1, 2, 3, 4, 5, 6, 7, 8, 9, 10 and 11, for example as oligomerization inhibitors of Voltage-Dependent Anion Channel (VDAC), or as inhibitors of hexokinase detachment from VDAC.

According to certain embodiments, the at least one compound is of Formula (IIa):

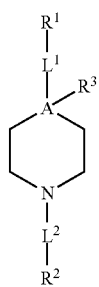

Formula (IIa)

wherein:

A is carbon (C);

R³ is a hydrogen, an unsubstituted or substituted amide or a heteroalkyl group comprising 3-12 atoms apart from hydrogen atoms, wherein at least one of said 3-12 atoms is a heteroatom, selected from nitrogen, sulfur and oxygen;

$L^1$ is an amino linking group —NR⁴—, wherein R⁴ is hydrogen, a $C_{1-5}$-alkyl, a $C_{1-5}$-alkylene or a substituted alkyl —CH₂R, wherein R is a functional group selected from hydrogen, halo, haloalkyl, cyano, nitro, hydroxyl, alkyl, alkenyl, aryl, alkoxyl, aryloxyl, aralkoxyl, alkylcarbamido, arylcarbamido, amino, alkylamino, arylamino, dialkylamino, diarylamino, arylalkylamino, aminocarbonyl, alkylaminocarbonyl, arylaminocarbonyl, alkylcarbonyloxy, arylcarbonyloxy, carboxyl, alkoxycarbonyl, aryloxycarbonyl, sulfo, alkylsulfonylamido, alkylsulfonyl, arylsulfonyl, alkylsulfinyl, arylsulfinyl or heteroaryl;

when R³ is hydrogen, then $L^1$ is preferably —NH—; when R³ is heteroalkyl group comprising 3-12 atoms, then $L^1$ is preferably —NC$_n$H$_{2n}$—, such that it forms a ring with R³;

R¹ is an aromatic moiety, which is optionally substituted with one or more of $C_{1-2}$-alkoxy, e.g. haloalkoxy, such as $C_{1-2}$-perfluoroalkoxy;

$L^2$ is a linking group consisting of 4-10 atoms (apart from hydrogen atoms), optionally forming a ring, whereof at least one of the atoms is nitrogen, said nitrogen forming part of an amide group or $L^2$ is $C_{1-5}$ alkyl or $C_{1-5}$ alkylene; said linking group $L^2$ bonds piperidine or piperazine moiety at nitrogen (N) atom; preferably, $L^2$ is selected from butanamidylene, N-methylbutanamidylene, N,N-dimethylbutanamidylene, 4-hydroxybutanamidylene, 4-oxobutanamidylene, 4-hydroxy-N-methylbutanamidylene, 4-oxo-N-methylbutanamidylene, 2-pyrrolidonylene, pyrrolidine-2,5-dionylene, 5-thioxo-2-pyrrolidinonylene and 5-methoxy-2-pyrrolidinonylene; and R² is an aryl, optionally substituted with halogen, optionally when R² is a phenyl it is substituted with halogen, further optionally when R² is naphthyl, $L^2$ is an alkylenyl group. In a specific embodiment, R³ is hydrogen, $L^1$ is —NH—, and R¹ is a phenyl substituted with trifluoromethoxy.

The invention also relates to use of the stereoisomers, enantiomers, mixtures thereof, and salts, particularly the physiologically acceptable salts, of the compounds of general Formula (I) and (IIa).

In some embodiments, A is carbon (C), R³ is hydrogen (H), $L^1$ is a NH group, R¹ is a phenyl substituted with one trifluoromethoxy, $L^2$ is pyrrolidine-2,5-dione, and R² is a phenyl substituted with a chlorine at the para position.

In some embodiments, A is carbon (C), R³ is a C(O)NCH₂C(O)OH group and is connected to both A and $L^1$, $L^1$ is a NCH₂ group and is connected to both R¹ and R³, R¹ is a phenyl, $L^2$ is methylene $C^1$ alkylene and R² is a naphthyl.

According to certain exemplary embodiments, methods of the present invention comprise administering to the subject compounds according to the general Formula (IIa), having the structural Formulae 10 and 11:

Formula 10

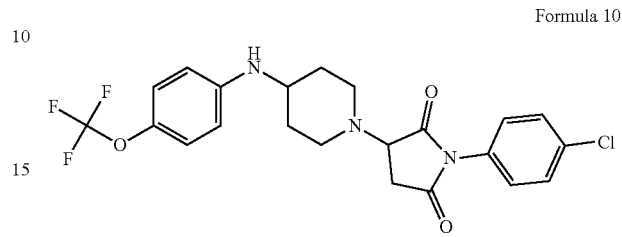

The compound of Formula 10 is also identified herein as AKOS022 or AKOS022075291.

Formula 11

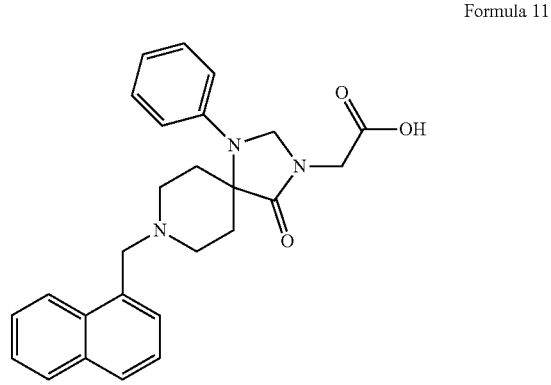 [SMILES: O=C(O)CN1CN(c2ccccc2)C2(CCN(Cc3cccc4ccccc34)CC2)C1=O]

The compound of Formula 11 is also identified herein as DIV 00781.

The compounds of general Formula (IIa) such as, without being limited to, the compounds of structural formulae 10 and 11, may be converted into the salts thereof, particularly physiologically acceptable salts for pharmaceutical use. Suitable salts of the compounds of general Formulae (IIa), such as, without being limited to, the compounds of structural formulae 10 and 11, may be formed with organic or inorganic acids, such as, without being limited to hydrochloric acid, hydrobromic acid, sulphuric acid, phosphoric acid, lactic acid, acetic acid, succinic acid, citric acid, palmitic acid or maleic acid. Compounds of general Formula (IIa) containing a carboxy group, may be converted into the salts thereof, particularly into physiologically acceptable salts for pharmaceutical use, with organic or inorganic bases. Suitable bases for this purpose include, for example, sodium salts, potassium salts, arginine salts, ammonium salts, or ethanolamine salts.

The compounds of general Formulae (I), (Ia), (Ib), (Ic), (Id), and (IIa), particularly the specific compounds of Formulae 1, 2, 3, 10 and 11, are inhibitors of Voltage-Dependent Anion Channel (VDAC) oligomerization and apoptosis. The effect of the compounds of the invention and of the specific compounds of formulae 1, 2, 3, 10 and 11 on VDAC oligomerization, i.e. their ability to inhibit VDAC oligomerization, may be determined, e.g. by Bioluminescence Resonance Energy Transfer (BRET2) technology that allows to directly monitor the oligomeric state of VDAC molecules in the native membrane in cells in live. BRET2 screening may be carried out as described in the art (e.g. Keinan et al., 2010. Mol Cell Biol 30, 5698-5709).

The compounds of general Formulae (I), (Ia), (Ib), (Ic), (Id), and (IIa), particularly the compound having Formula 1 (VBIT-4), inhibit the detachment of hexokinase (HK), particularly HK-I, from the mitochondrial VDAC. Without wishing to be bound by any theory or mechanism of action, the ability of the compounds of the invention, particularly VIBIT-4, to inhibit detachment of HK from VDAC contributes to their therapeutic effect on CNS-associated diseases, including mood disorders, psychotic disorders (particularly schizophrenia), Alzheimer disease, Parkinson disease, known to be associated with impaired brain energy metabolism due to HK detachment. Impaired mitochondrial energy metabolism was also shown to be involved in amyotrophic lateral sclerosis (ALS).

According to certain embodiments, the CNS-associated disease that can be treated with the compound of the present invention is selected from the group consisting of psychotic disorders, mood disorders and neurodegenerative disease. Each possibility represents a separate embodiment of the present invention.

According to some embodiments, the psychotic disorder is selected from the group consisting of, but not limited to, schizophrenia, autism spectrum disorder and anorexia nervosa. Each possibility represents a separate embodiment of the present invention.

According to certain exemplary embodiments, the psychotic disorder is schizophrenia.

According to certain embodiments, the mood disorder is selected from the group consisting of, but not limited to, bipolar disorder, major depressive disorder, persistent depressive disorder (also known as dythemia) and anxiety disorder. Each possibility represents a separate embodiment of the present invention.

According to certain exemplary embodiments, the mood disorder is bipolar disorder.

According to certain embodiments, the neurodegenerative disease is selected from the group consisting of, but not limited to, Alzheimer's disease, Parkinson disease and Amyotrophic Lateral Sclerosis (ALS). Each possibility represents a separate embodiment of the present invention.

According to certain exemplary embodiments, the neurodegenerative disease is Alzheimer's disease.

According to certain additional or alternative embodiments, the neurodegenerative disease is Parkinson disease.

According to certain additional or alternative embodiments, the neurodegenerative disease is ALS.

Figure 13:
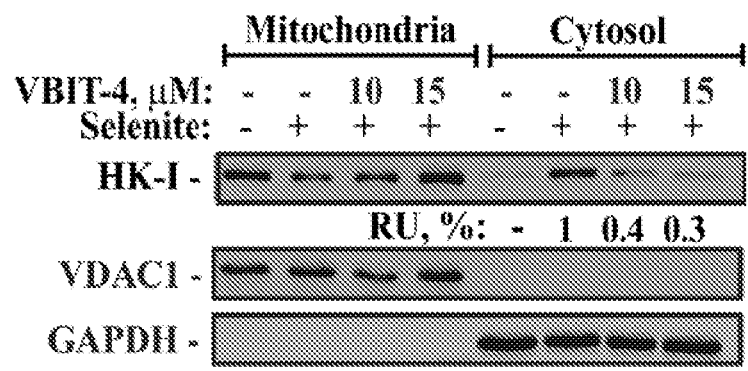
FIG. 13 shows immunoblots and quantitative data of selenite-induced HK-I release to the cytosol and inhibition by VBIT-4, presented in relative units (RU).

As exemplified herein, an exemplary compound of the invention, VBIT-4 (having formula 1) inhibits mitochondrion-bound HK detachment (FIG. 13). In addition to the metabolic function assigned to mitochondrion-bound HK (HK-I and HK-II), namely the coupling of cytosolic glycolysis to mitochondrial oxidative phosphorylation, it was shown that VDAC1-bound HK also prevents the release of pro-apoptotic factors and subsequent apoptosis accompanied with detachment of HK (see e.g. Shoshan-Barmatz V et al. 2009. Biophys Acta 1787, 421-430; Arzoine, L et al. 2009. J. Biol. Chem. 284, 3946-3955). Several pro-apoptotic agents have been shown to induce VDAC1-HK complex dissociation (see, e.g. Shoshan-Barmatz V et al. 2015. Biochim. Biophys. Acta 1848, 2547-2575). The present invention now shows that VBIT-4 inhibited HK detachment, as induced by apoptosis induction. This finding supports the concept of HK detachment being a pre-requisite for apoptosis induction. VBIT-4 inhibition of HK detachment suggests that such detachment is associated with VDAC1 oligomerization, with VBIT-4 inhibiting oligomerization and preventing HK detachment. In addition, attachment of HK-I and/or HK-II to mitochondrial VDAC has been was shown play a significant role in proper energy metabolism of mammalian cell, particularly of neuronal cells. Without wishing to be bound by certain specific mechanism or mode of action, the inhibiting activity of the compounds of the present invention on HK detachment contribute to its therapeutic effect on CNS disorders, particularly psychotic disorders, mood disorders and the neurodegenerative disease Alzheimer's disease, Parkinson disease and ALS.

The compounds of the invention exemplified by the compound of Formula 1 (VBIT-4) were found not toxic and well tolerated by rats. No mortality and no treatment-related clinical signs were observed during a study with 40 mg/kg administered via oral gavage (data not shown). Both food intake and body weight were normal in all animals. In addition, no significant changes in hematology and serum chemistry were observed. Post mortem examination showed no significant changes in organ weight, or macroscopic examination of liver, lung, testis, tongue, marrow bone and pathological tissues and no abnormal clinical symptoms were observed.

VBIT-4 showed an elimination half-life (PK) of 7.6 h, a stable metabolic profile and moderate intestinal permeability. VBIT-4 showed high plasma protein binding, with the bound compound fraction possibly serving as a reservoir from which slow release occurs (data not shown).

Animal models may serve as a resource for developing and evaluating treatments for disease associated with CNS disorders.

Features that characterize schizophrenia in animal models typically extend to schizophrenia in humans. Thus, efficacy in such animal models is expected to be predictive of efficacy in humans. Other psychiatric diseases including schizotypical and schizoaffective disorder, other acute- and chronic psychoses, and bipolar disorder (in particular, mania), have an overlapping symptomatology with schizophrenia. Various animal models of schizophrenia are known in the art.

One animal model of schizophrenia is protracted treatment with methionine. Methionine-treated mice exhibit deficient expression of GAD67 in frontal cortex and hippocampus, similar to those reported in the brain of postmortem schizophrenia patients. They also exhibit prepulse inhibition of startle and social interaction deficits (Tremonlizzo et al., 2002. PNAS, 99, 17095-17100). Another animal model of schizophrenia is methylaoxymethanol acetate (MAM)-treatment in rats. Pregnant female rats are administered MAM (20 mg/kg, intraperitoneal) on gestational day 17. MAM-treatment recapitulates a pathodevelopmental process to schizophrenia-like phenotypes in the offspring, including anatomical changes, behavioral deficits and altered neuronal information processing. More specifically, MAM-treated rats display a decreased density of parvalbumin-positive GABAergic interneurons in portions of the prefrontal cortex and hippocampus. In behavioral tests, MAM-treated rats display reduced latent inhibition. Latent inhibition is a behavioral phenomenon where there is reduced learning about a stimulus to which there has been prior exposure with any consequence. This tendency to disregard previously benign stimuli, and reduce the formation of association with such stimuli is believed to prevent sensory overload. Low latent inhibition is indicative of psychosis. Latent inhibition may be tested in rats in the following manner. Rats are divided into two groups. One group is pre-exposed to a tone over multiple trials. The other group has no tone presentation. Both groups are then exposed to an auditory fear conditioning procedure, in which the same tone is presented concurrently with a noxious stimulus, e.g. an electric shock to the foot. Subsequently, both groups are presented with the tone, and the rats' change in locomotor activity during tone presentation is monitored. After the fear conditioning the rats respond to the tone presentation by strongly reducing locomotor activity. However, the group that has been exposed to the tone before the conditioning period displays robust latent inhibition: the suppression of locomotor activity in response to tone presentation is reduced. MAM-treated rats, by contrast show impaired latent inhibition. That is, exposure to the tone previous to the fear conditioning procedure has no significant effect in suppressing the fear conditioning. Amphetamines, while known to be used for treating psychiatric disorders, may induce symptoms of psychosis very similar to those of acute schizophrenia spectrum psychosis. Amphetamine is known to disrupt latent inhibition, and is thus used as a model for primary psychotic disorders including schizophrenia.

Apomorphine-induced climbing (AIC) and Apomorphine-induced stereotype (AIS) in mice is another animal model that may be useful in this invention. The compounds of the invention are administered to mice at a desired dose level (e.g., via intraperitoneal administering). Subsequently, e.g., thirty minutes later, experimental mice are challenges with apomorphine (e.g., with 1 mg/kg sc). Five minutes after the apomorphine injection, the sniffing-licking-gnawing syndrome (stereotyped behavior) and climbing behavior induced by apomorphine are scored and recorded for each animal. Readings can be repeated every 5 min during a 30-min test session. Scores for each animal are totaled over the 30-min test session for each syndrome (stereotyped behavior and climbing). If an effect reach at least of 50% inhibition, an $ID_{50}$ value (95% confidence interval) is calculated using a nonlinear least squares calculation with inverse prediction. Mean climbing and stereotype scores can be expressed as a percent of control values observed in vehicle treated mice that receive apomorphine only (see Grauer S M et al. 2009. Psychopharmacology 204, 37-48).

In another well-established preclinical model of schizophrenia, rats exposed chronically to ketamine, an uncompetitive N-methyl-D-aspartate (NMDA) receptor antagonist, produces positive and negative psychotic symptoms and cognitive impairment. Long-Evans male rats are injected intraperitoneally with ketamine (30 mg/kg, twice a day) for two weeks during adolescence (2 month-old). Rats are behaviorally tested when they reach adulthood (approximately 4-5 month-old) for the behavioral symptoms to ketamine exposure and for the efficacy of treatment with the compounds of the invention to alleviate those symptoms (see, e.g., Enomoto et al. 2003. Progress in Neuro-Psychopharmacology & Biological Psychiatry 33, 668-675).

Such animal models of schizophrenia may be used to assay the effectiveness of the methods and compositions of the invention in treating schizophrenia or bipolar disorder (in particular, mania).

Depression is a mood disorder that can be classified per se or can be associated with other psychiatric states or with general medical conditions, typically chronic and/or life threatening diseases, including, for example, cancer, HIV/AIDS, ALS and multiple sclerosis. The efficacy of the methods and compositions of the present invention in treating depression may be assessed in animal models of depression. An exemplary animal model of depression is described in Example 8 hereinbelow.

Alzheimer disease (AD), which is the most common form of dementia, is characterized by gradual cognitive decline, eventually leading to death. Worldwide, 36 million people older than 65 years live with dementia, and this number is anticipated to double by 2030 and reach 115 million by 2050. The disease is characterized by the occurrence of brain senile plaques and neurofibrillary tangles, and is associated with the loss of brain synapses and synaptic dysfunction, inflammatory responses, and mitochondrial structural and functional abnormalities. The senile plaques associated with the disease contain a 39-43 amino acid-long amyloid-β peptide (Aβ), a fragment of the amyloid protein precursor, APP. Over-production of Aβ represents one of the pathological hallmarks of AD; it was shown that different aggregated forms of the Aβ stimulate reactive oxygen species (ROS) production in neurons. It has been recently shown that Aβ triggers neuronal oxidative stress by interfering with mitochondrial HKI activity and subcellular localization.

Dementia and cognitive impairments are hallmarks of Alzheimer's disease, and various animal models of these features are known in the art. The effect of exemplary product of the invention (VBIT-4, having formula 1) on AD on 5×FAD transgenic mice with AD-like disease is described in Example 6 hereinbelow.

Parkinson's disease (PD) is a neurological disorder characterized by a decrease of voluntary movements. The afflicted patient has reduction of motor activity and slower voluntary movements compared to the normal individual. The patient has characteristic "mask" face, a tendency to hurry while walking, bent over posture and generalized weakness of the muscles. There is a typical "lead-pipe" rigidity of passive movements. Another important feature of the disease is the tremor of the extremities occurring at rest and decreasing during movements. The etiology of PD is unknown. It belongs to a group of the most common movement disorders named parkinsonism, which affects approximately one person per one thousand. These other disorders grouped under the name of parkinsonism may result from viral infection, syphilis, arteriosclerosis and trauma and exposure to toxic chemicals and narcotics. Nonetheless, it is believed that the inappropriate loss of synaptic stability may lead to the disruption of neuronal circuits and to brain diseases. Whether as the result of genetics, drug use, the aging process, viral infections, or other various causes, dysfunction in neuronal communication is considered the underlying cause for many neurologic diseases, such as PD (Myrrhe van Spronsen and Casper C. 2010. Hoogenraad, Curr. Neurol. Neurosci. Rep., 10, 207-214).

Regardless of the cause of the disease, the main pathologic feature is degeneration of dopaminergic cells in basal ganglia, especially in substantia nigra. Due to premature death of the dopamine containing neurons in substantia nigra, the largest structure of the basal ganglia, the striatum, will have reduced input from substantia nigra resulting in decreased dopamine release. The understanding of the underlying pathology led to the introduction of the first successful treatment which can alleviate Parkinson's disease. Virtually all approaches to the therapy of the disease are based on dopamine replacement. Drugs currently used in the treatment can be converted into dopamine after crossing the blood brain barrier, or they can boost the synthesis of dopamine and reduce its breakdown. Unfortunately, the main pathologic event, degeneration of the cells in substantia nigra, is not helped. The disease continues to progress and frequently after a certain length of time, dopamine replacement treatment will lose its effectiveness.

There are a number of animal models for PD. Exemplary animal models for PD include the reserpine model, the methamphetamine model, the 6-hydroxydopamine (6-OHDA) model, the 1-methyl-4-phenyl-1,2,3,6-tetrahydropyridine (MPTP) model, the paraquat (PQ)-Maneb model, the rotenone model, the 3-nitrotyrosine model and genetic models using transgenic mice. Transgenic models include mice that over express α-synuclein, express human mutant forms of α-synuclein, or mice that express LRKK2 mutations (see, e. g. Ranjita B et al. 2002. BioEssays 24, 308-318, a review).

Amyotrophic Lateral Sclerosis (ALS) is characterized by degeneration of motor neurons and also by neuronal degeneration in the entorhinal cortex and hippocampus, memory deficits, and neuronal hyperexcitability in different brain areas such as the cortex. Animal models for ALS are known in the art. For example, rats expressing human Cu—Zn superoxide dismutase (SOD1) mutations are used as model animals for assessing the effect of various drugs on ALS. These rats develop a motor syndrome with symptoms and pathological features of the human disease (Howland D S et al. 2002. Proc Natl Acid Sci USA 99, 1604-1609).

The VDAC inhibitory piperazine and/or piperidine derivatives of the present invention can be administered alone, or within a pharmaceutical composition containing the VDAC inhibitory compounds of the invention together with a pharmaceutically acceptable carrier or excipient.

The compounds of general Formulae (I), (Ia), (Ib), (Ic), (Id), and (IIa), such as, without being limited to, the compounds of structural formulae 1, 2, 3, 4, 5, 6, 7, 8, 9, 10 and 11, particularly the specific compounds of Formulae 1, 2, 3, 10 and 11, and the pharmaceutically acceptable salts thereof, may be formulated in a pharmaceutical composition, optionally comprising other active substances, and one or more of inert conventional excipients, as known to the skilled artisans. The pharmaceutical compositions may be prepared according to the general guidance provided in the art, e.g. by Remington, The Science and Practice of Pharmacy (formerly known as Remington's Pharmaceutical Sciences), ISBN 978-0-85711-062-6. The pharmaceutical compositions, e.g. in the form of solid dosage forms, topical dosage form, and/or parenteral dosage forms, e.g. tablets, capsules, creams, ointments, patches, injections, and others as known in the art constitute another aspect of the invention.

Particularly, the compounds of general Formulae (I), (Ia), (Ib), (Ic), (Id), and (IIa), particularly of structural formulae 1, 2, 3, 4, 5, 6, 7, 8, 9, 10 and 11, more particularly the specific compounds of Formulae 1, 2, 3, 10 and 11, and the pharmaceutically acceptable salts thereof, may be formulated as nanoparticles. The nanoparticles may be prepared in well-known polymers, e.g. polylactic-co-glycolic acid, e.g., as described in H. K. Makadia, S. J. Siegel, Poly Lactic-co-Glycolic Acid (PLGA) as Biodegradable Controlled Drug Delivery Carrier, Polymers (Basel), 3 (2011) 1377-1397; and others. Generally, the compounds may be co-dissolved with the polymer in a suitable organic solvent, and the organic phase may be then dispersed in an aqueous phase comprising stabilizers and/or surface active agents. The stabilizers may be, e.g. polyvinyl alcohol, with molecular weights from about 89000 to 98000, and hydrolysis degree from about 99%. Upon evaporation of organic solvent from the aqueous phase, the nanoparticles may be purified, e.g. by centrifugation and washing.

The encapsulated compounds, e.g. in form of nanoparticles, of general Formulae (I), (Ia), (Ib), (Ic), (Id), and (IIa), such as, without being limited to, the compounds of structural formulae 1, 2, 3, 4, 5, 6, 7, 8, 9, 10 and 11, particularly the specific compounds of Formulae 1, 2, 3, 10 and 11, and the pharmaceutically acceptable salts thereof, may be advantageously used in various routes of administering. Intranasal route may be suitable mode of administering in this regard. Alternatively, the nanoparticles may be administered systemically to accumulate in cancerous tissues.

The dose of compounds of general Formulae (I), (Ia), (Ib), (Ic), (Id), and (IIa), such as, without being limited to, the compounds of structural formulae 1, 2, 3, 4, 5, 6, 7, 8, 9, 10 and 11, particularly the specific compounds of Formulae 1, 2, 3, 10 and 11, and the pharmaceutically acceptable salts thereof, required to achieve treatment or prevention of a disease or a disorder or a condition usually depends on the pharmacokinetic and pharmacodynamic properties of the compound which is to be administered, the patient, the nature of the disease, disorder or condition and the method and frequency of administering. Suitable dosage ranges for compounds of general Formulae (I), (Ia), (Ib), (Ic), (Id), and (IIa), such as, without being limited to, the compounds of structural formulae 1, 2, 3, 4, 5, 6, 7, 8, 9, 10 and 11, particularly the specific compounds of Formulae 1, 2, 3, 10 and 11, and the pharmaceutically acceptable salts thereof, may be from 1.0 to 100 mg/kg body weight.

EXAMPLES

Materials

Carbonyl cyanide m-chlorophenyl hydrazone (CCCP), cytochalasin B, dimethyl sulfoxide (DMSO), DL-dithiothreitol (DTT), EDTA, HEPES, leupeptine, phenylmethylsulfonyl fluoride (PMSF), and Tris were purchased from Sigma (St. Louis, Mo.). Coelenterazine (Deep Blue C [DBC]) was obtained from Bioline (Taunton, Mass.). Digitonin came from Calbiochem-Novobiochem (Nottingham, UK). Rabbit monoclonal antibodies against VDAC1 (ab154856) and mouse monoclonal antibodies against GAPDH (ab9484) came from Abcam (Cambridge, UK). Monoclonal antibodies against actin were obtained from Millipore (Billerica, Mass.) Horseradish peroxidase (HRP)-conjugated anti-mouse and anti-rabbit antibodies were obtained from Promega (Madison, Wis.). Dulbecco's modified Eagle's medium (DMEM) and the supplements fetal bovine serum (FBS), L-glutamine and penicillin-streptomycin were purchased from Biological Industries (Beit-Haemek, Israel). The compound of Formula 10 (AKOS022) was obtained from AKosConsulting & Solutions GmbH (Germany), under catalogue number AKOS022075291.

Methods

LC-MS Analysis

The chromatography was performed using a regular Bridge C18 column 4.6×50 mm, 3.5 μm, kept at 40° C. The materials were eluted at 2 mL/min, with mixture of 0.01M aqueous solution of ammonium carbonate and acetonitrile, with acetonitrile ramping from 5% to 100% for periods as described below and eluting with 100% acetonitrile, with detection at the target mass.

Tissue Culture

HEK-293, HeLa, SH-SY5Y and K-Ras-transformed $Bax^{-/-}/Bak^{-/-}$ mouse embryonic fibroblast (MEF) cell lines were grown at 37° C. under an atmosphere of 95% air and 5% $CO_2$ in DMEM supplemented with 10% FBS, 2 mM L-glutamine, 1000 U/ml penicillin and 1 mg/ml streptomycin. T-REx-293 cells (HEK cells stably containing the pcDNA6/TR regulatory vector and thus expressing the tetracycline repressor; Invitrogen) stably expressing hVDAC1-shRNA and showing low (10-20%) endogenous VDAC1 expression (referred to herein as T-REx-pS10) were grown under the same conditions as HEK-293 cells, with an addition of 5 μg/ml blasticidin.

Hexokinase Detachment from Mitochondria

Cells treated with apoptosis inducers in the absence or presence of the tested compounds were harvested, washed twice with PBS, pH 7.4 and gently resuspended at 6 mg/ml in ice-cold buffer (100 mM KCl, 2.5 mM $MgCl_2$, 250 mM sucrose, 20 mM HEPES/KOH pH 7.5, 0.2 mM EDTA, 1 mM dithiothreitol, 1 μg/ml leupeptin, 5 mg/ml cytochalasin B and 0.1 mM PMSF) containing 0.025% digitonin and incubated for 10 min on ice. Samples were centrifuged at 10,000×g (relative centrifugal force—RCF) at 4° C. for 5 min to obtain supernatants (cytosolic extracts free of mitochondria) and pellet (fraction that contains mitochondria). Hexokinase I released to the cytosol was analyzed by immunoblotting using anti-hexokinase-I-specific antibodies. Anti-VDAC1 and anti-GAPDH antibodies were used to verify that the cytosolic extracts are mitochondria-free.

Preparation of Intermediate 1

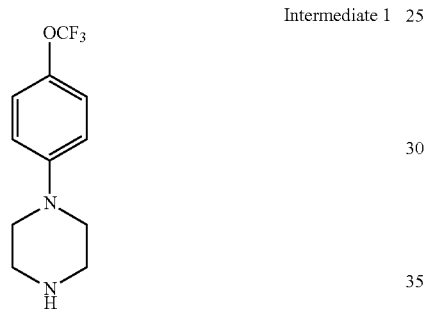

Intermediate 1

Step A

Intermediate 1 was synthesized according to the scheme below.

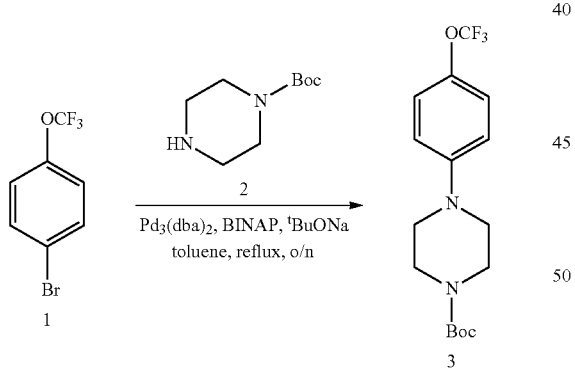

The starting material reagent 1 (p-trifluoromethoxy-bromobenzene; 1-Bromo-4-(trifluoromethoxy)benzene) was used. To a solution of reagent 1 (2.41 g, 10 mmol) in toluene (50 mL) were consecutively added the following compounds: reagent 2 (1-Boc-piperazine; tert-butyl piperazine-1-carboxylate) (1.68 g, 9 mmol), $Pd_2(dba)_3$ (tris-(dibenzylidenacetone)dipalladium) (290 mg, 0.5 mmol), 2,2'-bis(diphenylphosphino)-1,1'-binaphthyl (BINAP) (311 mg, 0.5 mmol) and sodium t-butoxide (1.92 g, 20 mmol). The mixture was refluxed under $N_2$ atmosphere overnight. The solvent was evaporated to provide crude reagent 3 (tert-butyl 4-(4-(trifluoromethyl)-phenyl)-piperazine-1-carboxylate) as a residue.

Step B

Reagent 3 was directly used for next step without further purification.

Boc group was removed by acid hydrolysis according to the scheme below

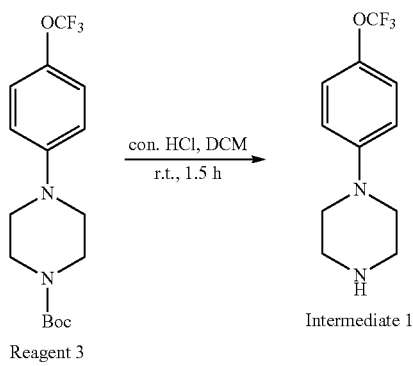 [SMILES: CC(C)(C)OC(=O)N1CCN(c2ccc(OC(F)(F)F)cc2)CC1 ; FC(F)(F)Oc1ccc(N2CCNCC2)cc1]

The mixture comprising crude reagent 3 in 50 mL of concentrated hydrochloric acid and 50 mL of dichloromethane was stirred for 1.5 hours at room temperature. After phase separation, the dichloromethane phase was discarded, and the aqueous phase was evaporated in vacuo to dryness. The residue was dissolved in 50 mL of aqueous sodium hydroxide solution, 2.0 M, and 50 mL dichloromethane were added and stirred for additional 1.5 hours. The organic phase was collected and concentrated in vacuo to provide Intermediate 1 as brown oil (2.0 g, 80% yield for steps A and B).

The Intermediate 1 was analyzed using LC-MS method as described above with ramping over 1.6 minutes and elution for 1.4 minutes, with detection at +246. A representative chromatogram and respective mass spectra of two peaks of interest relating to Intermediate 1 are represented in FIG. 1.

Example 1: Preparation of Compound of Formula 2 (VBIT-3)

The compound of Formula 2 (1-(4-chlorophenyl)-3-(4-(4-(trifluoromethoxy)phenyl)piperazin-1-yl)pyrrolidine-2,5-dione; VBIT-3) was synthesized according to the reaction scheme below:

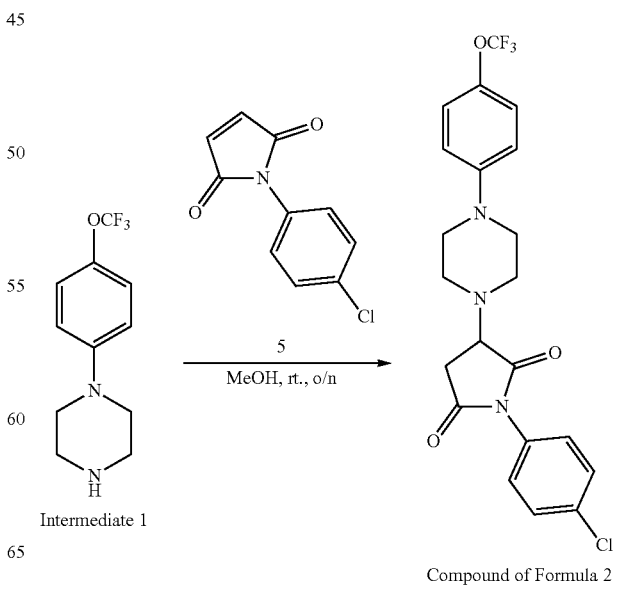

To a solution of Intermediate 1 (207 mg, 1 mmol) in methanol (2 mL) was added reagent 5 (1-(4-Chlorophenyl)-1H-pyrrole-2,5-dione) (246 mg, 1 mmol). The reaction was stirred at room temperature overnight. The final mixture was concentrated and purified by preparative reverse-phase HPLC to provide compound of Formula 2 (VBIT-3) as white solid (100 mg, 22% yield).

Figure 2A:
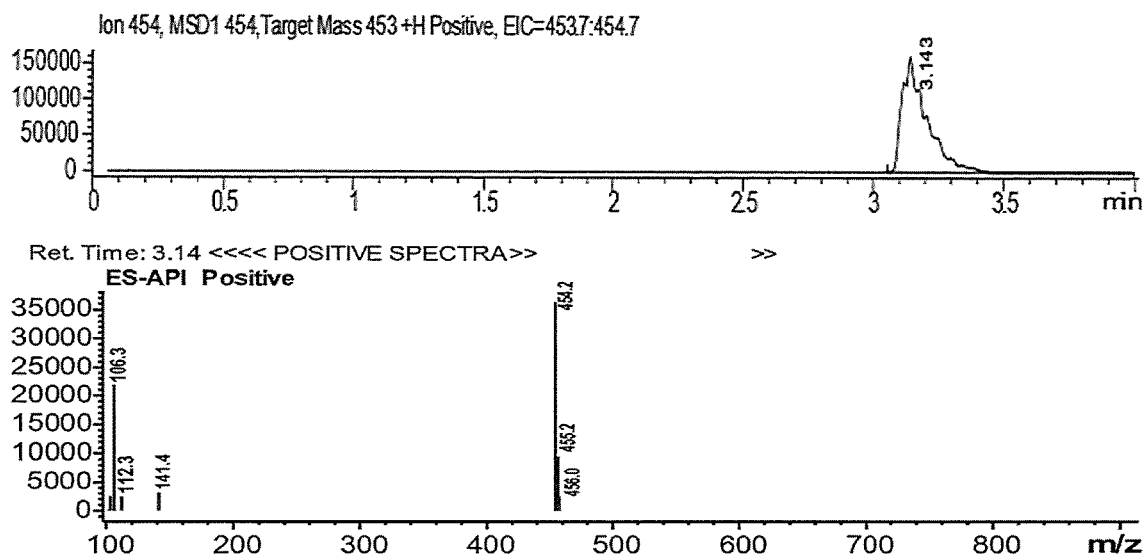
FIG. 2a demonstrates a representative chromatogram and respective mass spectrum of the peak of interest relating to the compound of Formula 2.

The product (compound of Formula 2 (VBIT-3)) was analyzed using LC-MS method as described above with ramping over 3 minutes and elution for 1 minute, with detection at +453. The chromatogram is represented in FIG. 2a.

The NMR spectra were obtained on 400 MHz apparatus (by Varian).

Figure 2B:
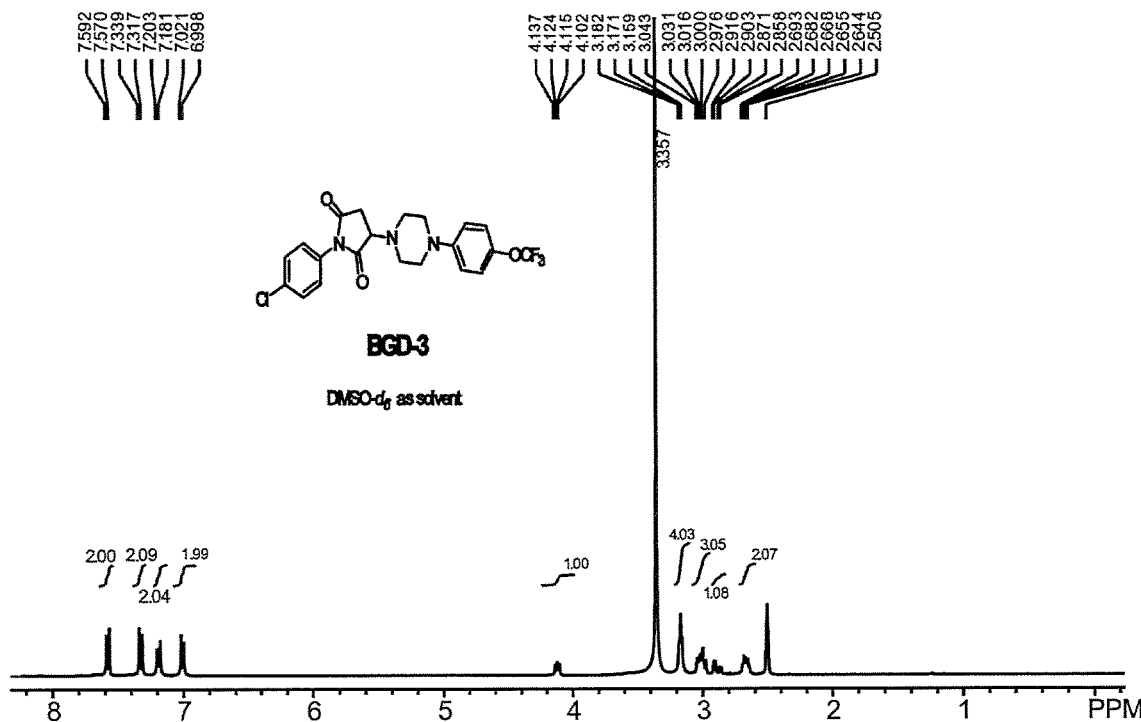
FIG. 2b demonstrates a representative NMR spectrum relating to the compound of Formula 2.

$^{1}$H NMR (400 MHz, DMSO-d$_{6}$): δ7.592 (d, J=2.2 Hz, 2H), 7.339 (d, J=2.2 Hz, 2H), 7.201 (d, J=2.2 Hz, 2H), 7.021 (d, J=2.1 Hz, 2H), 4.137 (dd, J=1.3 Hz, 1H), 3.159 (m, J=1.1 Hz, 4H), 3.00 (m, J=2.4 Hz, 3H), 2.871 (m, J=1.3 Hz, H), 2.680 (m, J=2.0 Hz, 2H). The spectrum is shown in the FIG. 2b.

Example 2 Preparation of Compound of Formula 1 (VBIT-4

The compound of Formula 1 (N-(4-chlorophenyl)-4-hydroxy-3-(4-(4-(trifluoromethoxy)phenyl) piperazin-1-yl)butanamide; VBIT-4) was synthesized according to the reaction scheme below:

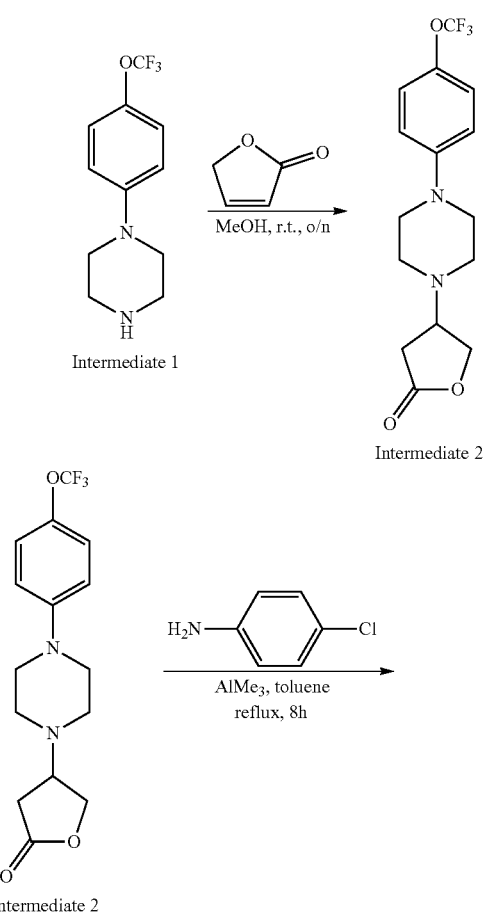

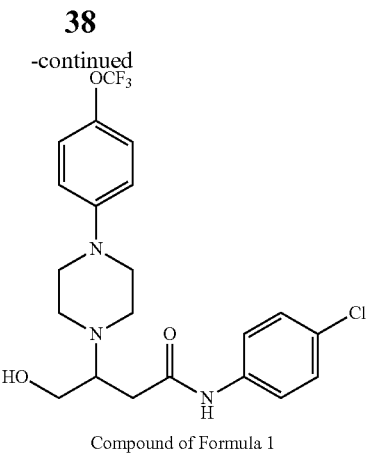

Compound of Formula 1

Step A

A mixture of Intermediate 1 (2.0 g, 8 mmol) and furan-2(5H)-one (2(5H)-Furanone) (1.3 g, 16 mmol) in methanol (MeOH) (5 mL) was stirred at room temperature overnight. The mixture was evaporated in vacuo and the residue was purified by reverse phase preparative HPLC to provide Intermediate 2 [3-(4-(4-(trifluoromethoxy)phenyl)piperazin-1-yl)-dihydrofuran-2(3H)-one) as white solid (1.3 g, 0.4 mmol, 50% yield).

Figure 3:
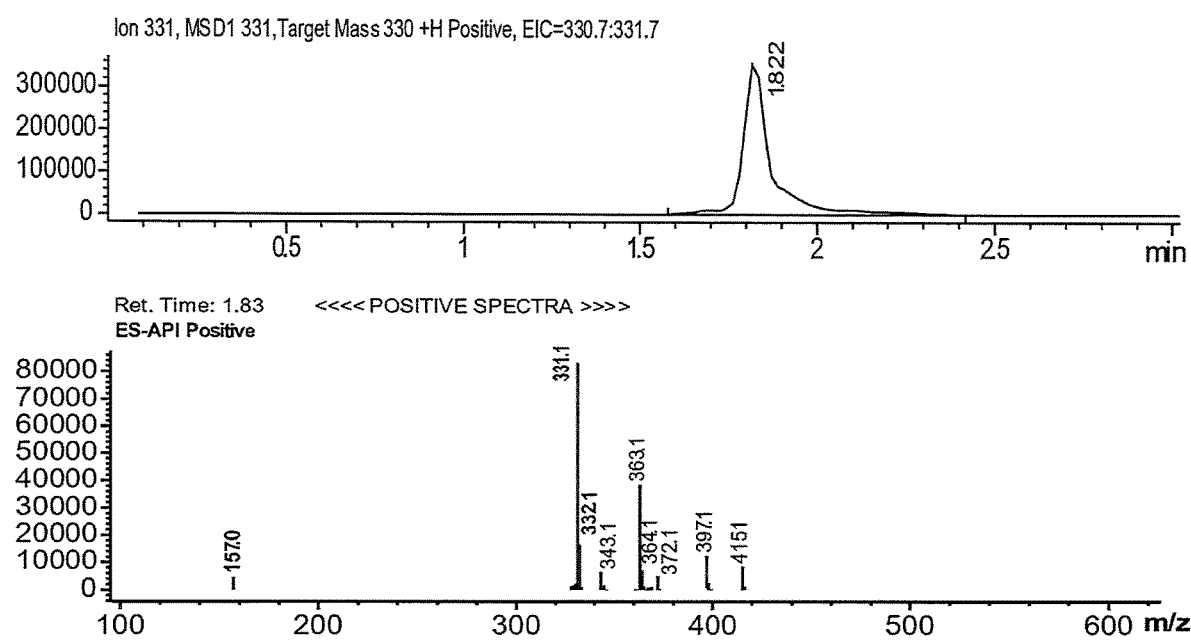
FIG. 3 demonstrates a representative chromatogram and respective mass spectrum of the peak of interest relating to Intermediate 2.

The product (Intermediate 2) was analyzed using LC-MS method as described above with ramping over 1.6 minutes and elution for 1.4 minutes, with detection at +330. The chromatogram is represented in FIG. 3.

Step B

To a solution of 4-chloroaniline (254 mg, 2 mmol) in toluene (5 mL) trimethyl aluminum (AlMe$_{3}$) was added (2.0 M in toluene, 2 mL). After stirring for 10 minutes, Intermediate 2 (330 mg, 1.0 mmol) was added to the solution and the resulting mixture was heated to 80° C. for 8 hours. After cooling to room temperature, the solvent was evaporated in vacuo and the residue was purified by reverse preparative HPLC to afford the compound of Formula 1 (VBIT-4) as white solid (200 mg, 44% yield).

Figure 4A:
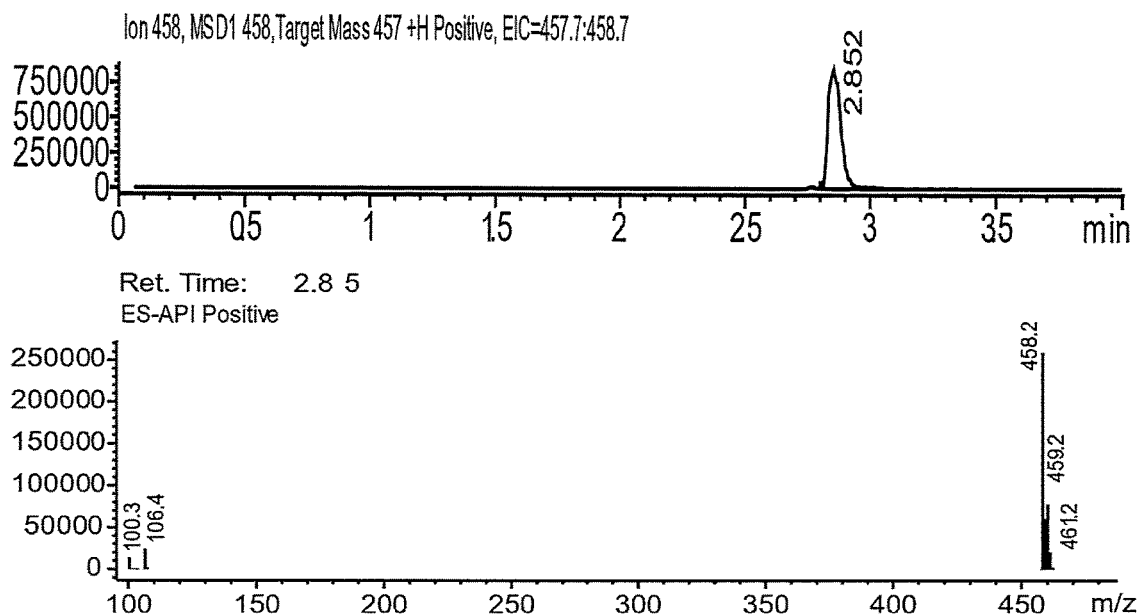
FIG. 4a demonstrates a representative chromatogram and respective mass spectrum of the peak of interest relating to the compound of Formula 1.

The product (Compound of Formula 1) was analyzed using LC-MS method as described above with ramping over 3 minutes and elution for 1 minute, with detection at +457. The chromatogram is represented in FIG. 4a.

The NMR spectra were obtained on 400 MHz apparatus (by Varian).

Figure 4B:
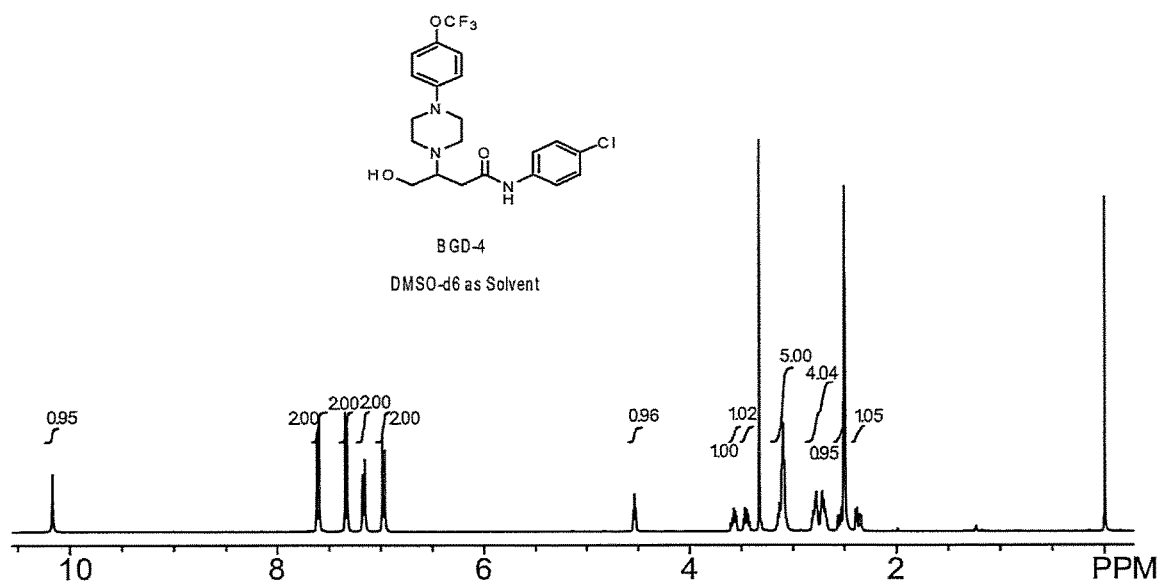
FIG. 4b demonstrates a representative NMR spectrum relating to the compound of Formula 1.

$^{1}$H NMR (400 MHz, DMSO-d$_{6}$): δ10.081 (s, H), 7.601 (d, J=0.5 Hz, 2H), 7.341 (d, J=1.2 Hz, 2H), 7.177 (d, J=2.2 Hz, 2H), 6.980 (d, J=2.3 Hz, 2H), 4.538 (dd, J=1.2 Hz, 1H), 3.561 (m, J=1.3 Hz, H), 3.440 (m, J=1.4 Hz, H), 3.112 (m, J=1.2 Hz, 5H), 2.807 (m, J=1.6 Hz, 2H), 2.709 (m, J=1.5, Hz, 2H), 2.400 (m, J=1.4, Hz, H), 2.150 (m, J=1.4, Hz, H). The spectrum is shown in the FIG. 4b.

Example 3: Preparation of Compound of Formula 3 (VBIT-12)

Preparation of compound of Formula 3 (2-(1-(naphthalen-1-ylmethyl)-4-(phenylamino)piperidine-4-carboxamido)acetic Acid; VBIT-12)

Step 1

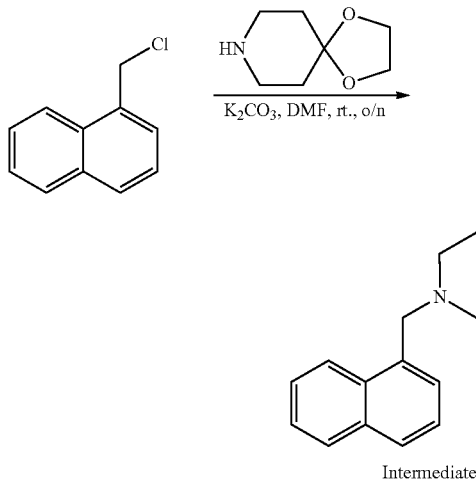

Intermediate 3

1-(Chloromethyl)naphthalene (8.8 g, 50 mmol) was dissolved in dimethylformamide (DMF) (100 mL), and potassium carbonate (13.8 g, 100 mmol) was added, followed by 4-piperidone ethylene ketal (1,4-dioxa-8-azaspiro[4.5]decane) (7.2 g, 50 mmol). The mixture was stirred at room temperature overnight. The solvent was evaporated in vacuo and the residue was purified by chromatography in silica gel (eluting with dichloromethane) to provide pure naphthylated ketal (Intermediate 3) as white solid (8.5 g, 60% yield).

Figure 5:
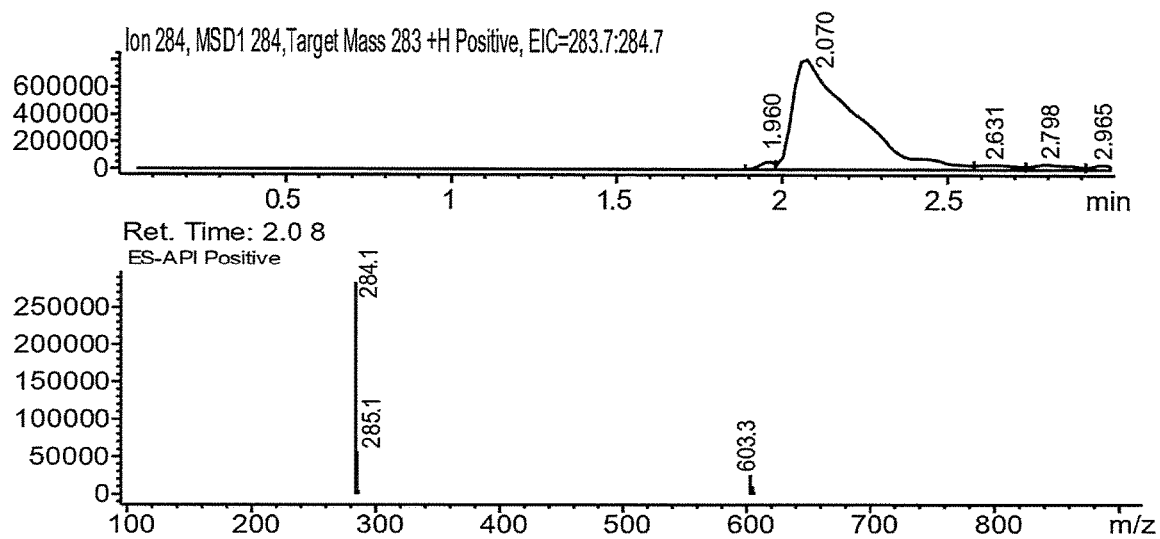
FIG. 5 demonstrates a representative chromatogram and respective mass spectrum of the peak of interest relating to Intermediate 3.

Intermediate 3 was analyzed using LC-MS method as described above with ramping over 1.6 minutes and elution for 1.4 minute, with detection at +283. The chromatogram is represented in FIG. 5.

Step 2

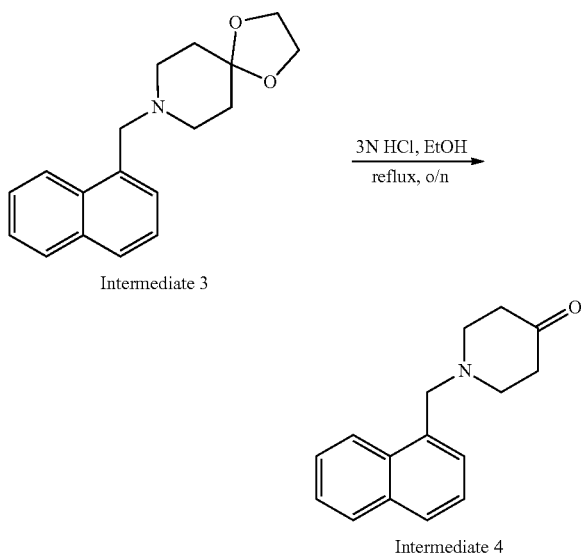

Intermediate 4

A solution of Intermediate 3 (product of Step 1) (1.42 g, 5 mmol) in 20 ml of 3N hydrochloric acid (HCl) in ethanol (EtOH) was refluxed overnight. The resulting mixture was concentrated in vacuo to provide Intermediate 4 (1-(naphthalen-1-ylmethyl)piperidin-4-one), which was used with no further purification.

Figure 6:
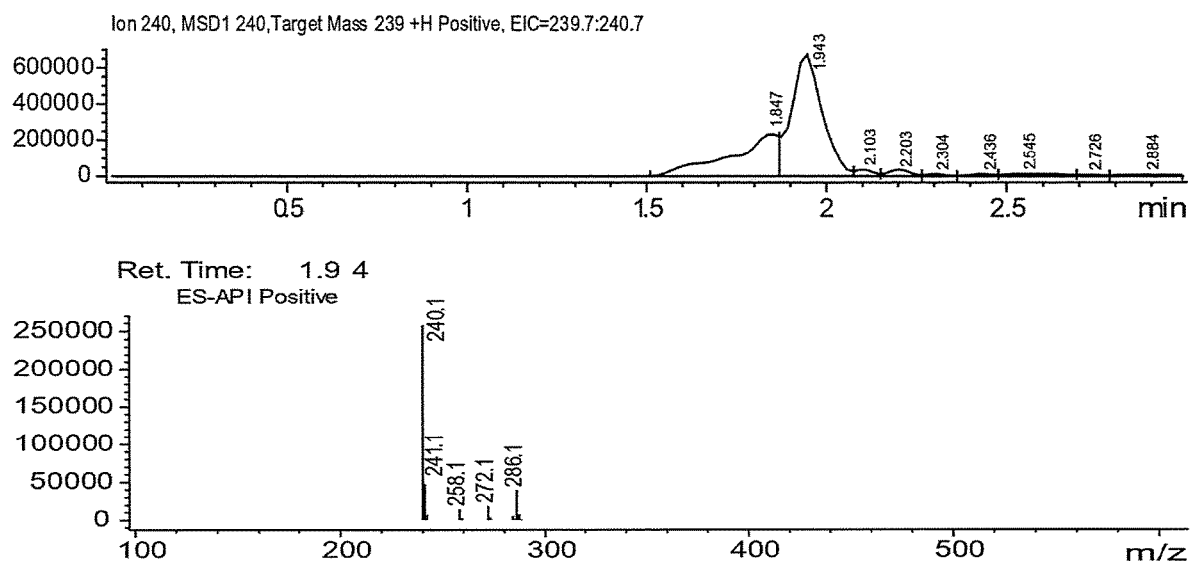
FIG. 6 demonstrates a representative chromatogram and respective mass spectrum of the peak of interest relating to Intermediate 4.

The product (Intermediate 4) was analyzed using LC-MS method as described above with ramping over 1.6 minutes and elution for 1.4 minute, with detection at +239. The chromatogram is represented in FIG. 6.

Step 3

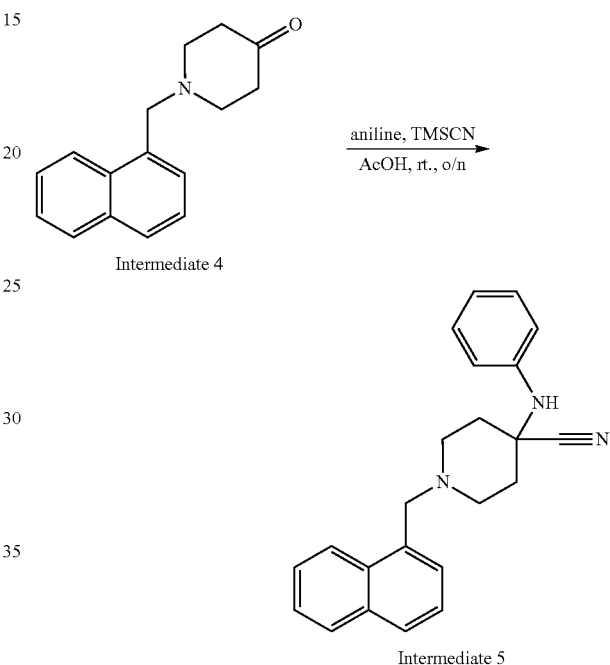

Intermediate 5

Intermediate 4 (N-methylnaphtyl-4-piperidinone) (2.4 g, 10 mmol) and aniline (930 mg, 10 mmol) were dissolved in glacial acetic acid (AcOH) (25 mL). Thereafter, trimethylsilyl cyanide (TMSCN) was added dropwise (1.3 mL, 10 mmol) over a 10-min period, maintaining the temperature below 40° C. using a cold water bath. The solution was stirred overnight and then poured into ammonium hydroxide ice mixture, formed by 50 mL of concentrated ammonium hydroxide solution and 100 g of crushed ice. Additional concentrated ammonium hydroxide was slowly added until pH rose to 10. The resultant mixture was extracted three times with 100 mL of chloroform, and the combined organic layers were dried over sodium sulfate, filtered and concentrated to a yellow nitrile residue (Intermediate 5,1-(naphthalen-1-ylmethyl)-4-(phenylamino)piperidine-4-carbonitrile) which was used in the next step directly without further purification.

Figure 7:
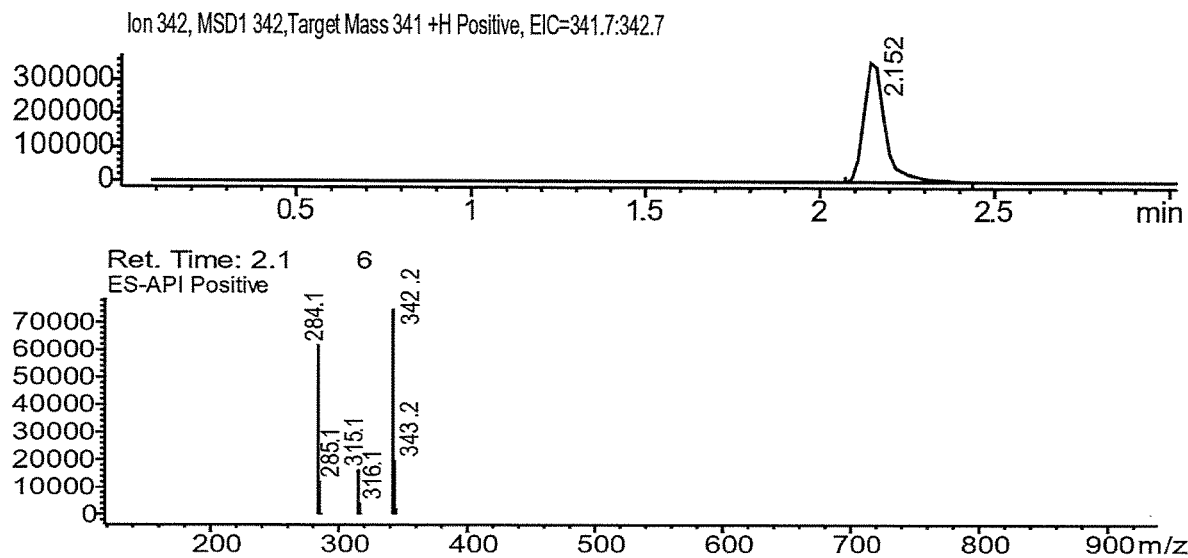
FIG. 7 demonstrates a representative chromatogram and respective mass spectrum of the peak of interest relating to Intermediate 5.

The product (Intermediate 5) was analyzed using LC-MS method as described above with ramping over 1.6 minutes and elution for 1.4 minute, with detection at +341. The chromatogram is represented in FIG. 7.

Step 4

The nitrile (Intermediate 5) was hydrolyzed according to the scheme below:

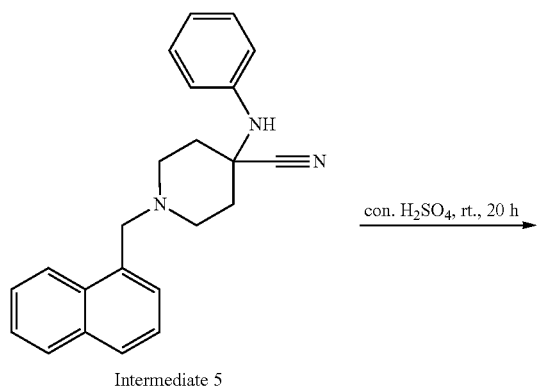

Intermediate 5

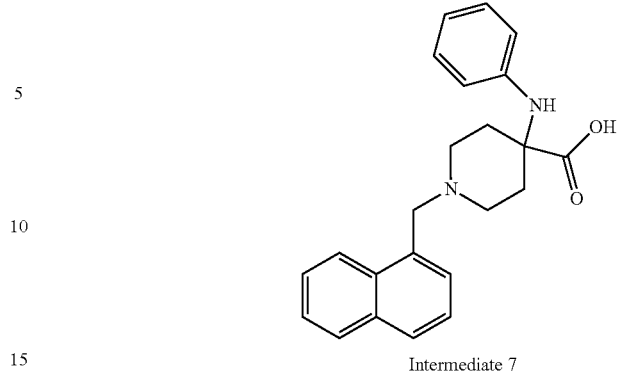

Intermediate 7

Intermediate 6 (360 mg, 1.0 mmol) was dissolved in ethylene glycol (10 mL), and potassium hydroxide (KOH) (280 mg, 5 mmol) was added. The resulting mixture was heated to 150° C. and stirred overnight. After cooling to room temperature, the final mixture was concentrated in vacuo and purified by reverse phase preparative HPLC to provide the free carboxylic acid (Intermediate 7,1-(naphthalen-1-ylmethyl)-4-(phenylamino)-piperidine-4-carboxylic acid) as white solid (200 mg, 50% yield).

Figure 9:
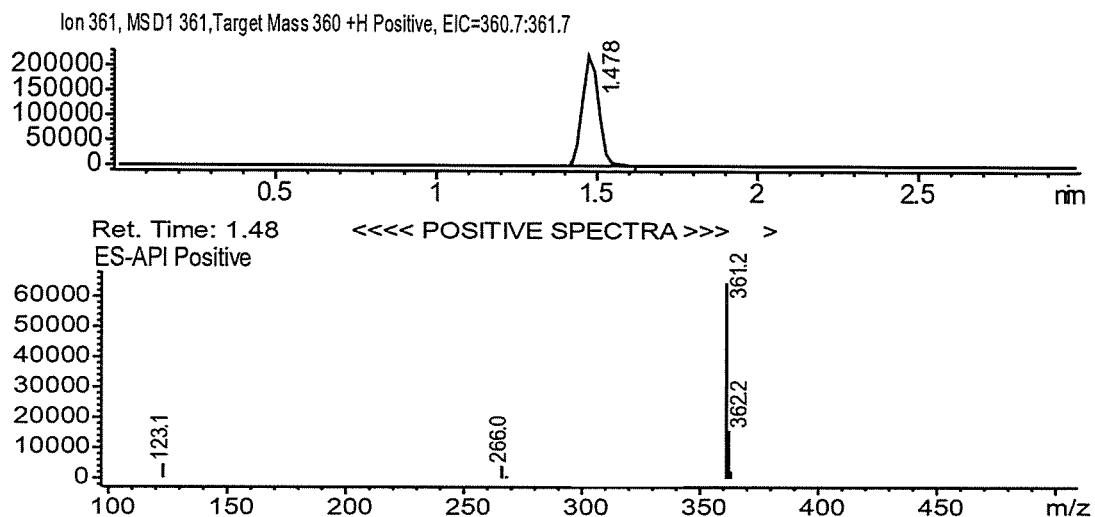
FIG. 9 demonstrates a representative chromatogram and respective mass spectrum of the peak of interest relating to Intermediate 7.

The product (Intermediate 7) was analyzed using LC-MS method as described above with ramping over 1.6 minutes and elution for 1.4 minute, with detection at +360. The chromatogram is represented in FIG. 9.

Step 6

Intermediate 7 was glycinated with methyl 2-aminoacetate (methyl glycinate) according to the scheme below:

Intermediate 6

Intermediate 5 (the product of step 3) was mixed with 10 mL of concentrated sulfuric acid ($H_2SO_4$). The mixture was stirred at room temperature overnight. A concentrated ammonium hydroxide solution was slowly added until pH rose to 10. The final mixture was concentrated and purified by reverse phase preparative HPLC to provide the amide (Intermediate 6,1-(naphthalen-1-ylmethyl)-4-(phenylamino) piperidine-4-carboxamide) as white solid (400 mg, 11% yield for the steps 2-4).

Figure 8:
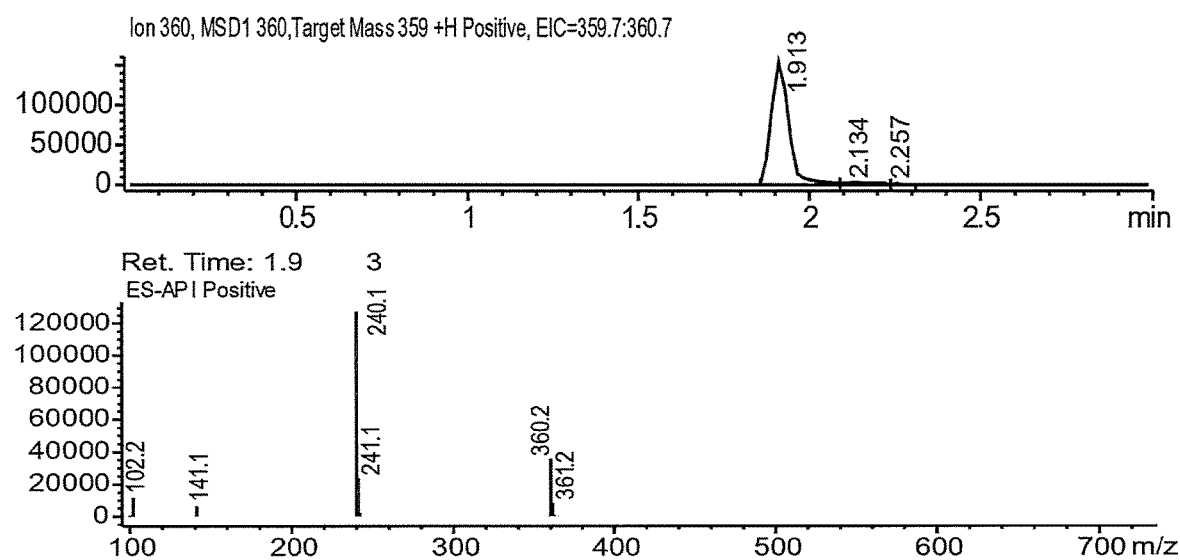
FIG. 8 demonstrates a representative chromatogram and respective mass spectrum of the peak of interest relating to Intermediate 6.

The product (Intermediate 6) was analyzed using LC-MS method as described above with ramping over 1.6 minutes and elution for 1.4 minute, with detection at +359. The chromatogram is represented in FIG. 8.

Step 5

Intermediate 6 was further hydrolyzed to carboxylic acid according to the scheme below:

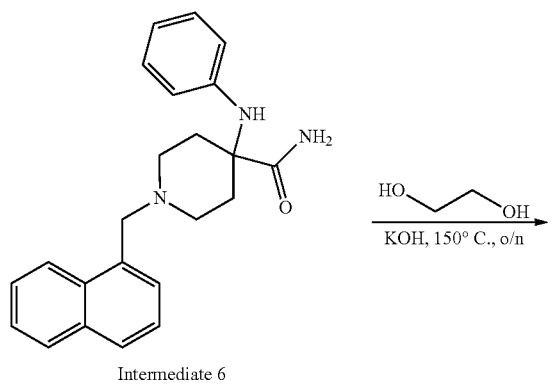

Intermediate 6

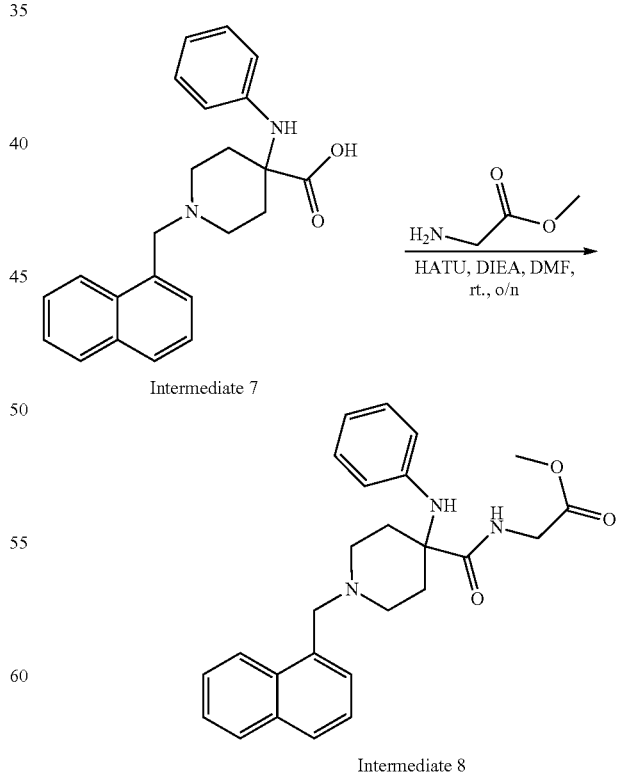

Intermediate 7

Intermediate 8

Intermediate 7 (180 mg, 0.5 mmol), HATU (1-[Bis(dimethylamino)methylene]-1H-1,2,3-triazolo-[4,5-b]-pyridinium 3-oxid hexafluorophosphate) (380 mg, 1.0 mmol), N,N-diisopropylethylamine (DIEA) (260 mg, 2.0 mmol), and methyl glycinate (90 mg, 1.0 mmol) were dissolved in dimethyl formamide (DMF) (10 mL), and the solution was stirred at room temperature overnight. The resulting mixture was concentrated in vacuo and purified by reverse phase preparative HPLC to provide the glycinate methyl ester (Intermediate 8, methyl (1-(naphthalen-1-ylmethyl)-4-(phenylamino)piperidine-4-carbonyl)glycinate) as white solid (100 mg, 46% yield).

Figure 10:
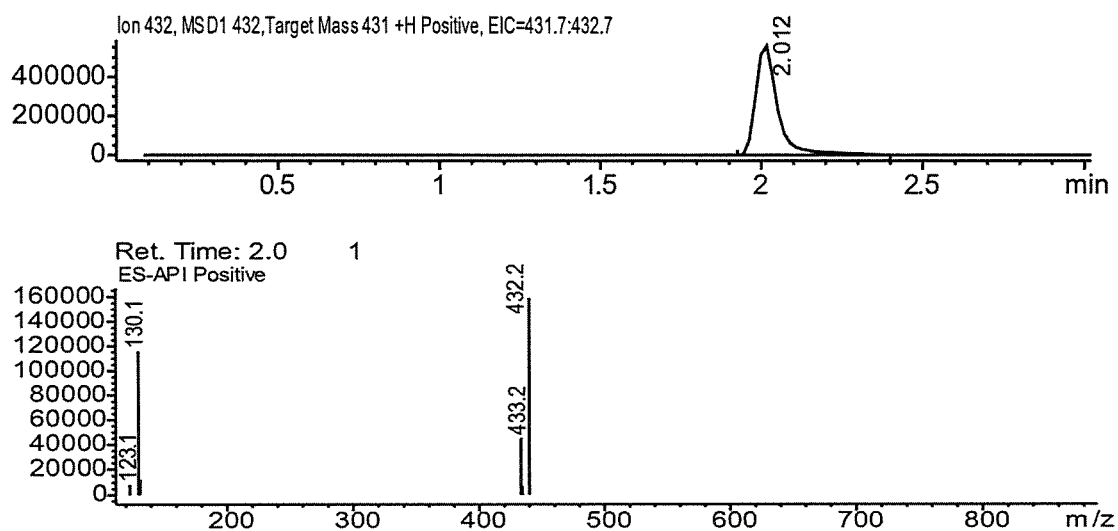
FIG. 10 demonstrates a representative chromatogram and respective mass spectrum of the peak of interest relating to Intermediate 8.

The product (Intermediate 8) was analyzed using LC-MS method as described above with ramping over 1.6 minutes and elution for 1.4 minute, with detection at +431. The chromatogram is represented in FIG. 10.

Step 7

Intermediate 8 (the glycinate methyl ester product of Step 6) was hydrolyzed with lithium hydroxide in tetrahydrofuran, according to the scheme below:

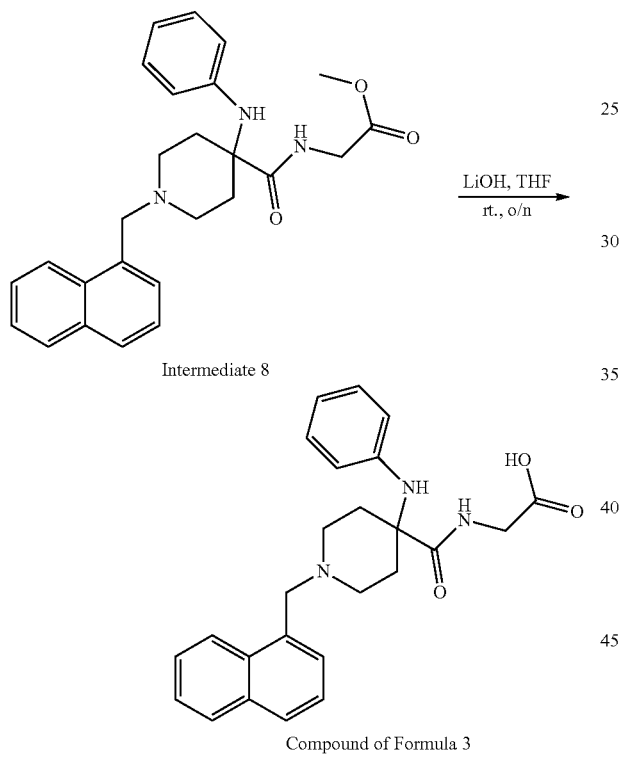

Intermediate 8

Compound of Formula 3

To a solution of Intermediate 8 (100 mg, 0.23 mmol) in 5 mL of THF, a solution of lithium hydroxide (LiOH) (40 mg, 1.0 mmol) in 5 mL of water was added, the resulting mixture was stirred at room temperature overnight. Thereafter, the pH was adjusted to about 7 with 1.0 N HCl. The mixture was concentrated in vacuo and purified by preparative HPLC to provide the compound of Formula 3 (VBIT-12) (20 mg, 20% yield) as white solid.

Figure 11A:
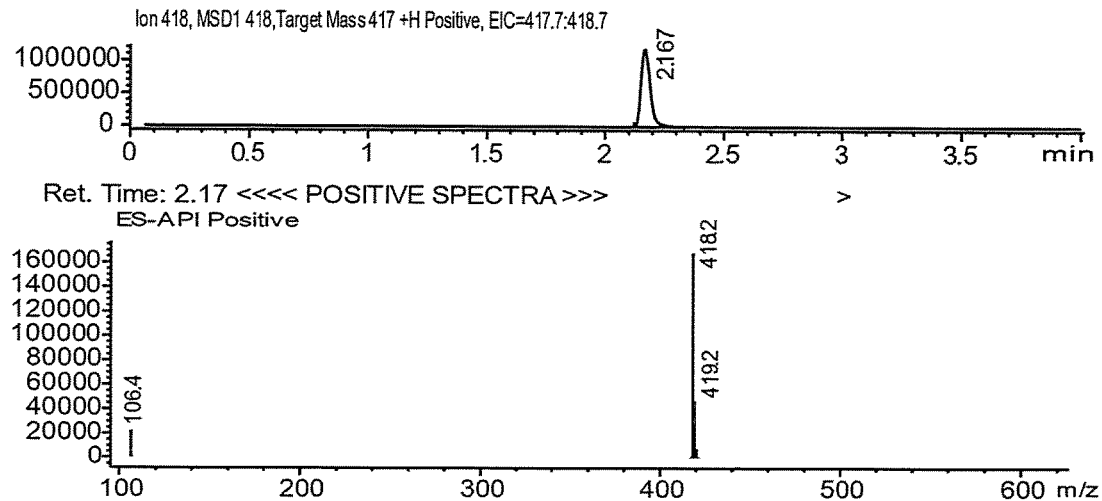
FIG. 11a demonstrates a representative chromatogram and respective mass spectrum of the peak of interest relating to the compound of Formula 3.

The product (compound of Formula 3; IUPAC name: 2-(1-(naphthalen-1-ylmethyl)-4-(phenylamino)piperidine-4-carboxamido)acetic acid) was analyzed using LC-MS method as described above with ramping over 3 minutes and elution for 1 minute, with detection at +417. The chromatogram is represented in FIG. 11a.

The NMR spectra were obtained on 400 MHz apparatus (by Varian).

$^1$H NMR (400 MHz, DMSO/D2O-d6): δ8.63 (d, H), 8.1 (s, H), 7.9 (d, J=1.2 Hz, 2H), 7.89 (d, J=2.2 Hz, 2H), 7.87 (d, J=2.3 Hz, 2H), 7.71 (dd, J=1.2 Hz, 2H), 7.67 (d, J=1.3 Hz, 2H), 7.16 (2, J=1.4 Hz, 2H), 6.78 (m, 4H), 3.80 (s, 2H), 3.71 (s, 2H), 2.31 (d, J=2.4, Hz, 2H), 2.25 (s, 2H), 2.17 (t, J=2.4, 2H), 1.98 (t, J=1.9, 2H), 1.88 (t, J=1.8, 2H)

Figure 11B:
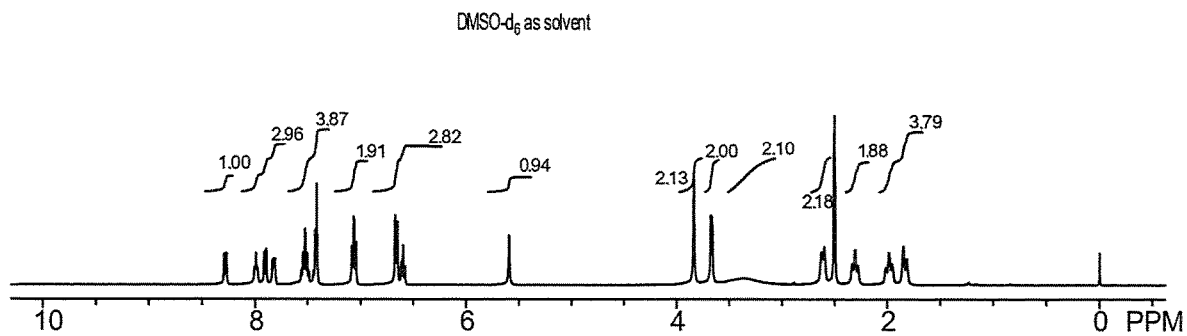
FIG. 11b demonstrates a representative NMR spectrum in deuterated DMSO relating to the compound of Formula 3.
Figure 11C:
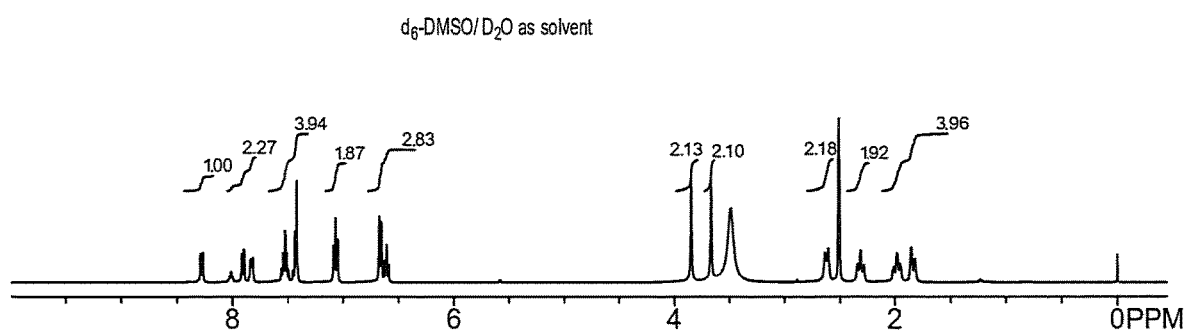
FIG. 11c demonstrates a representative NMR spectrum in deuterated DMSO and deuterated water ($D_2O$) relating to the compound of Formula 3.

The spectra in d6-DMSO and in d6-DMSO with D$_2$O are shown in the FIGS. 11b and 11c respectively.

Example 4: Chiral Separation of Compound of Formula 1 (VBIT-4) Enantiomers

Racemic compound of Formula 1 (VBIT-4) was analyzed by analytical chiral HPLC. Briefly, the material was eluted on Chiralpak-IC3 column (4.6×100 mm, 3 m), kept at 35° C., at 2 mL/min, with acetonitrile and 20% of 0.1% solution of DEA in methanol. Two peaks, with 0.38 min difference in retention time (2.32 and 2.7 min), were obtained in expected ratio as about 50.0%. Preparative chiral HPLC was then conducted. Each peak was collected separately. The enantiomers were analyzed by 400 MHz NMR but were not discernable in deuterated DMSO.

$^1$H NMR (400 MHz, DMSO-d$_6$): δ10.081 (s, H), 7.601 (d, J=0.5 Hz, 2H), 7.341 (d, J=1.2 Hz, 2H), 7.177 (d, J=2.2 Hz, 2H), 6.980 (d, J=2.3 Hz, 2H), 4.538 (dd, J=1.2 Hz, 1H), 3.561 (m, J=1.3 Hz, H), 3.440 (m, J=1.4 Hz, H), 3.112 (m, J=1.2 Hz, 5H), 2.807 (m, J=1.6 Hz, 2H), 2.709 (m, J=1.5, Hz, 2H), 2.400 (m, J=1.4, Hz, H), 2.150 (m, J=1.4, Hz, H).

Figure 12A:
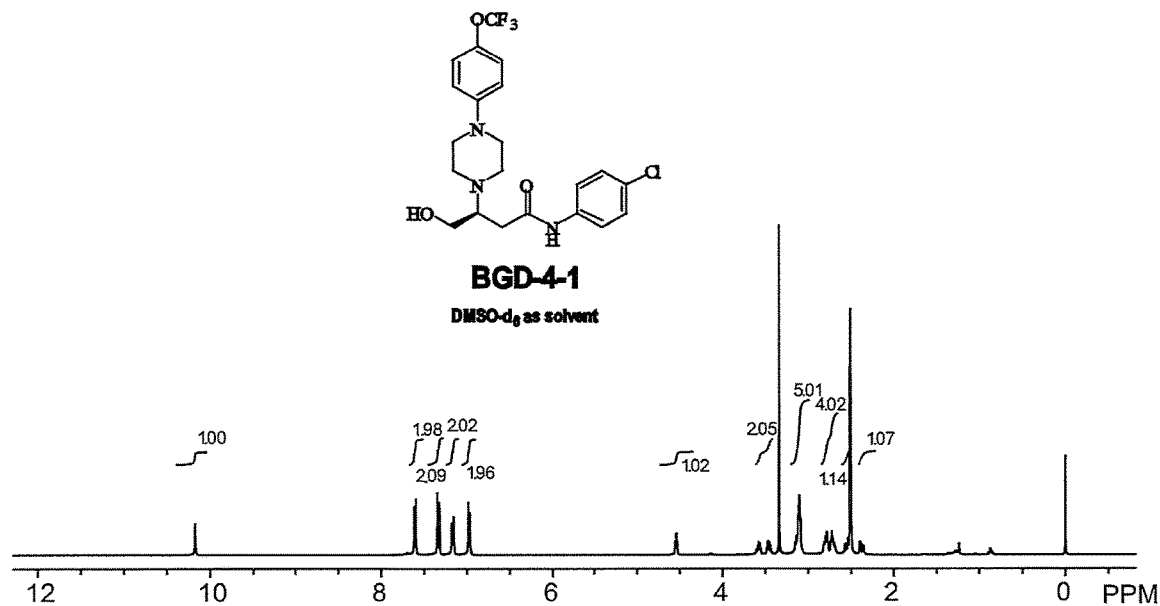
FIGS. 12a and 12b demonstrate representative NMR spectra in deuterated DMSO relating to separated single enantiomers of the compound of Formula 1 (identified as BGD-4-1 and VBIT-4-2, respectively).
Figure 12B:
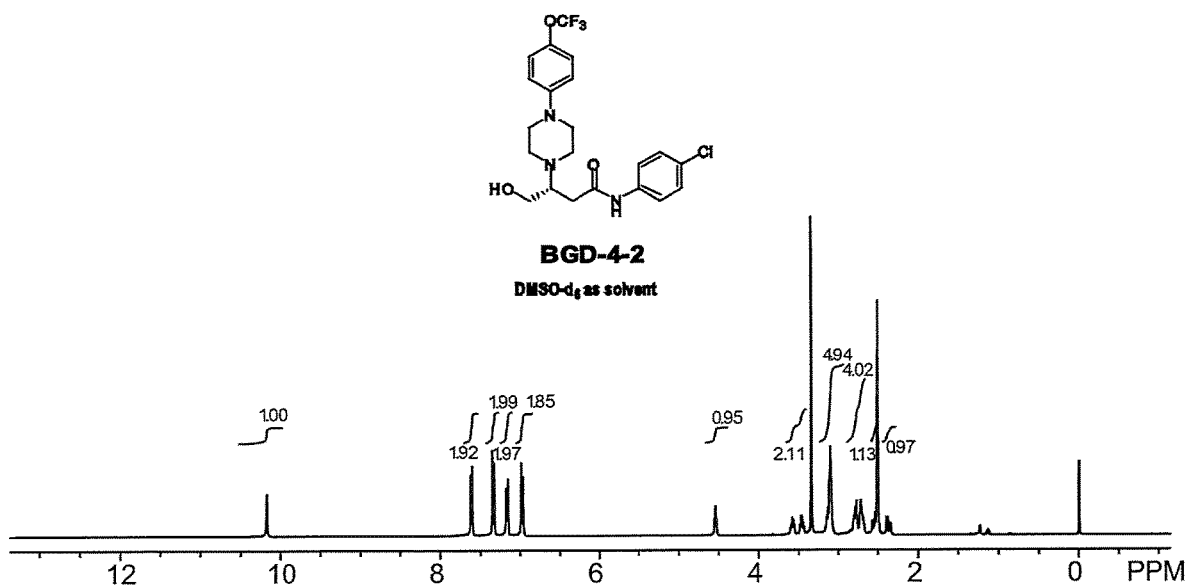

FIG. 12a demonstrates a representative NMR spectrum in deuterated DMSO relating to the separated single enantiomer of the compound of Formula 1, VBIT-4-1 (also referred to as BGD-4-1). FIG. 12b demonstrates a representative NMR spectrum in deuterated DMSO relating to the separated single enantiomer of the compound of Formula 1, VBIT-4-2 (also referred to as BGD-4-2).

Example 5: Effect of Compound of Formula 1 on HK-I Release from Mitochondria

HEK-293 cells were incubated without and with the racemic compound of Formula 1 (VBIT-4) (10 or 15 μM) for 2 hours and then with or without selenite (15 μM, 4 h), trypsinized, washed with PBS, protein concentration was determined and harvested.

Hexokinase-I (HK-I) release from the mitochondria was determined as described above in the Methods section (hexokinase detachment from mitochondria). Briefly, to assess HK-I release, cells were incubated on ice for 10 min with 0.025% digitonin, centrifuged, and the pellet (mitochondria—Mito) and supernatants (cytosol—Cytos) were subjected to SDS-PAGE and immunoblotting, using anti-HK-I, antibodies. Anti-VDAC1 and anti-GAPDH antibodies were used to verify that the cytosolic extracts are mitochondria-free. The results of HK release from the mitochondria as induced by selenite are presented as immunoblots, with the cytosolic and mitochondrial fractions confirmed by immunoblotting of GAPDH (glyceraldehyde-3-phosphate dehydrogenase) and VDAC1, respectively, in FIG. 13. The quantitative data of selenite-induced HK-I release to the cytosol by VBIT-4 is presented as relative units (RU).

The results show that apoptosis induction by selenite resulted in the detachment of mitochondria-bound HK that was subsequently detected in the supernatant of digitonin-treated cells. This selenite-induced HK detachment was inhibited in the presence of VBIT-4. The results show that in the absence of apoptosis induction, most of the HK is bound to the mitochondria, indicating that VBIT-4 inhibited HK detachment, as induced by apoptosis induction.

Example 6: Effect of Compound of Formula 1 on Learning and Memory Task of 5×FAD Transgenic Mice with AD-Like Disease The effect of the compound of Formula 1 (VBIT-4) on learning and memory task of 5×FAD transgenic mice with AD-like disease (Webster, S. J., et al, 2014. Frontiers in genetics 5,88, ([5×FAD B6.Cg-Tg APPSwFILon, PSEN1*M146Ln*L286V6799Vas/J]) was tested using the radial-arm water maze for testing learning and memory task. These mice present detectable phenotypes of intracellular and extracellular amyloid plaques at 2 months of age; develop cognitive impairments at 4-5 months and exhibits neuronal death at 9 months.

Figure 15A:
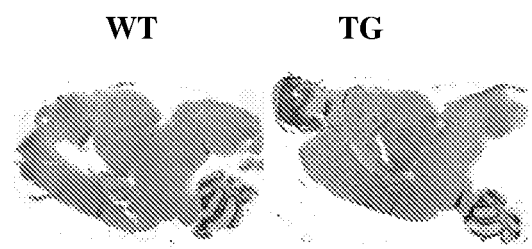
FIG. 15a shows cross section of wild type (WT) and transgenic mice with AD-like disease (TG).
Figure 15B:
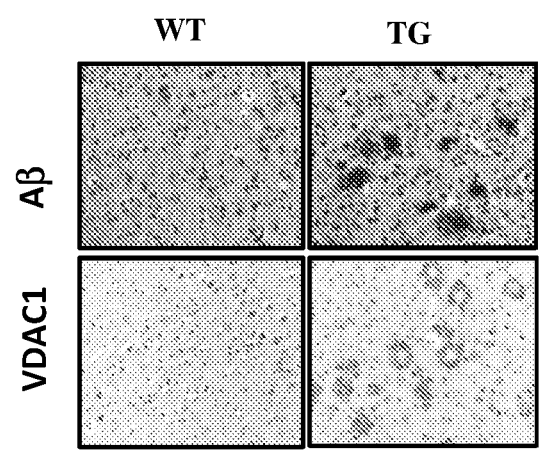
FIG. 15b shows immuno-staining of brain sections from the WT and TG mice presented in FIG. 15A with anti-Aβ or anti-VDAC1 antibodies.

VDAC is highly expressed in the brain of the transgenic mice with AD-like disease. FIG. 15 shows cross-sections of brain from wild type (WT) and 5×FAD transgenic (TG) mice (FIG. 15A) and immuno-staining of brain sections from WT and TG mice with anti-Aβ or anti-VDAC1 antibodies (FIG. 15B).

The compound of Formula 1 (VBIT-4) was dissolved in drinking water as follows: about 24 mg of VBIT-4 were transferred to Eppendorf tube and dissolved in 120 μl of 100% DMSO by Vortex mixer. Clear solution was obtained. About 10 mL solution of 1 M of HCl was prepared from 6 M HCl solution, provided by Pierce, Rockford, Ill., USA. About 370 μL of the 1M HCl solution was used to acidify 120 mL of drinking water. The VBIT-4 DMSO solution (120 μL) was slowly added (by dropping) into the acidic water and mixed by magnetic stirring. The final pH was between 4.8 and 5.0. If the solution became milky, further 10 to 30 μL of HCl solution were added to obtain clear solution. The amount was sufficient for 24 mice at dose of 20 mg/kg and drinking volume of 5 mL per mouse per day.

Animals at age of two months were assigned to three groups: transgenic treated (TG-T, 8 males and 3 females), transgenic vehicle (TG-V, 8 males and 3 females), and wild type (WT, 10 males and 8 females). Of these, 2 males in TG-T group died during the study.

Two-month old 5×FAD mice were provided with 0.9% of DMSO solution or VBIT-4 solution (20 mg/kg in 0.9% DMSO) in drinking water, replaced with fresh solution three times a week in the first month and thereafter twice a week for additional 3 months.

When the mice reached the age of six months, a two-day radial-arm water maze (RAWM) trial was performed as described previously (Jennifer Alamed, et al, Nature Protocols 1. 2006. 1671-1679) to test the effect of VBIT-4 on learning and memory task. An RAWM containing six swim paths (arms) was used. The arms were extending out from an open central area with an escape platform located at the end of one arm (the goal arm). The goal arm location remained constant for a given mouse. On day 1, mice were trained for 15 trials (spaced over 3 h), with trials alternating between visible and hidden platforms. On day 2, mice were trained for 15 trials with the hidden platform.

Entry into an incorrect arm was scored as an error, and the times spent by the animal to find the platform were recorded. The results are demonstrated in FIGS. 14A and 14B.

Figure 14A:
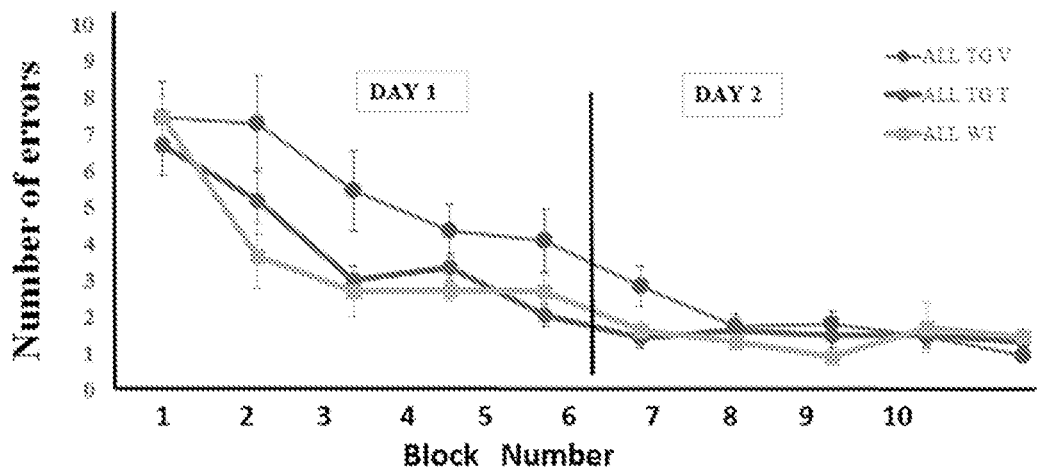
FIG. 14a demonstrates the effect of compound of Formula 1 on learning and memory of transgenic mice with Alzheimer's disease like symptoms using Radial Arm Water Maze test; number of errors is demonstrated as function of learning blocks.
Figure 14B:
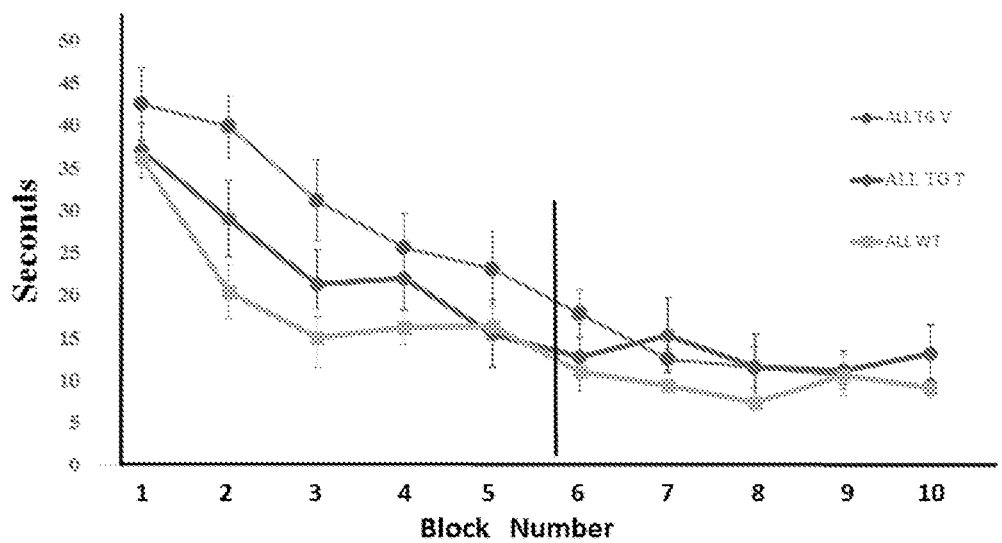
FIG. 14b demonstrates the effect of compound of Formula 1 on learning and memory of transgenic mice with Alzheimer's disease like symptoms using Radial Arm Water Maze test; total time per test is demonstrated as function of learning blocks.

FIG. 14A shows the number of errors, while FIG. 14B shows the total time spend in the water maze, as function of number of learning blocks. The number of errors data (FIG. 14A, data presented as mean±standard error of the mean) from RAWM was assessed using ANOVA test; a significant difference in animal's memory training between the three groups: WT-mice (n=18), 5×FAD/APOE (n=13) and 5×FAD/APOE treated with VBIT-4 (n=9) in different measurement times (trials) was obtained with F (9,159)=2.03 (p=0.03). To examine the source of differences the post-hoc test of Bonferroni-type was used. The non-transgenic mice trained better in comparison to non-treated TG mice (p=0.007). The TG mice treated with VBIT-4 performance was better than untreated TG and there was no difference between TG VBIT-4 treated group and the WT group. A trend for the improved performance (training) of the VBIT-4-TG treated group compared to non-treated TG group was seen (p=0.06).

The data of total time spent (FIG. 14B, data presented as mean±standard error of the mean) from RAWM was analyzed using repeated measures ANOVA test; a significant difference was obtained in animal's memory training between the three mouse groups: WT (n=18), 5×FAD/APOE (n=13) and 5×FAD/APOE treated with VBIT-4 (n=9) in different measurement times (trials), with F (2,35)=6.91, p=0.003. To examine the source of differences the post-hoc test of Bonferroni-type was used. The non-transgenic mice trained learned better in comparison to non-treated TG mice (p=0.003). The performance of TG mice treated with VBIT-4 was better than untreated TG and there was no difference between TG VBIT-4 treated group and the WT group.

Figure 16A:
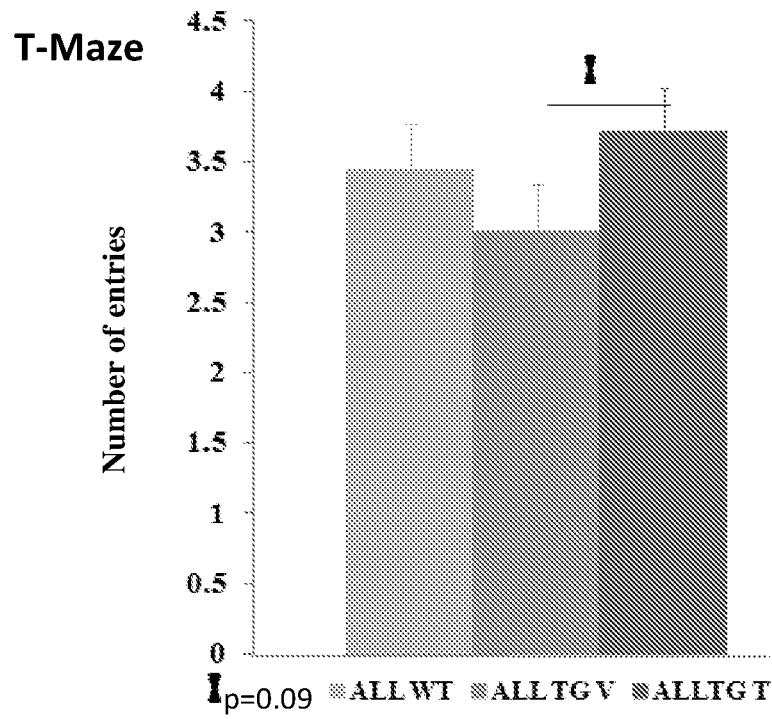
FIGS. 16a and 16b shows memory function of wild type mice (WT) and transgenic mice with AD-like disease (TG) untreated (TG V) or treated with VBIT-4 (TG T).
Figure 16B:
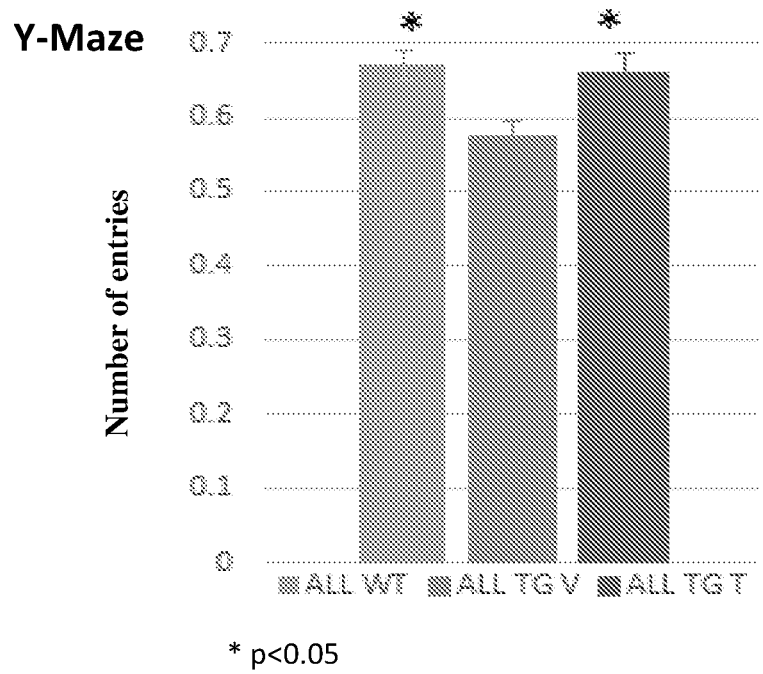

To assess memory function, VBIT-4 was given to 5×FAD transgenic (TG) mice with AD-like disease (in drinking water) and the mice were subjected to T-maze (FIG. 16a) and Y-maze (FIG. 16b) tests, after 6 months of treatment. Wild type (WT) mice and TG mice treated with a vehicle (0.9% DMSO solution) served as control.

T-Maze assay is based on the willingness of rodents to explore a new environment and allows for evaluating cognition, especially spatial and working memory (Rosenmann, H., et al., 2008. Exp Neurol 212(1), p. 71-84). Y-maze assay evaluates the willingness of the mice to explore new environments and to assess memory function and is useful in evaluating the effects of drugs on cognition.

The TG mice treated with VBIT-4 showed improved learning and memory tasks, reaching levels of wild type mice, in several tests. The performance of the transgenic mice with AD-like disease treated with VBIT-4 was equivalent to the performance of wild type mice (FIG. 16). This suggests that VBIT-4 reaches its target at sufficient concentrations to mediate its effects.

Example 7: Effect of Compound of Formula 1 on Schizophrenia

Startle response is comprised of a constellation of reflexes elicited by sudden relatively intense stimuli. It offers many advantages as a behavioral measure of central nervous system activity when elicited by acoustic (noise burst), electrical (cutaneous), tactile (air puff), or visual (light flash) stimuli. The startle reflex has served as a tool for studying fundamental properties of nervous function of complex behavioral states and cognitive processes. The forebrain modulates several forms of startle plasticity including the habituation and prepulse inhibition (PPI). Changes in startle magnitude through repeated stimulus presentations-habituation and sensitization represent the simple forms of learning. Quantification of startle habituation and sensitization in rodent has direct physiological relevance to human CNS function. In fact, the most well accepted animal physiology models for schizophrenia are startle habituation and PPI.

Startle magnitude is reduced when the pulse stimulus is preceded 30 to 500 msec by a weak prepulse. This inhibition ("gating") of a motor response elicited by a weak sensory event, termed PPI, provides an operational measure of sensorimotor gating. Prepulse stimuli of 3, 6, or 12 dB above the 70 dB background noise inhibit the startle response elicited by 120-dB pulse stimuli. Prestimuli used in intramodal studies of sensorimotor gating of acoustic startle are by the delivery of a discrete acoustic prepulse several msec before the startle pulse, with intensity below startle threshold. Holding the interval between the prepulse and pulse stimuli constant at 100 msec, typically yields suitable levels of PPI, ranging from 20% to 80% inhibition.

The effect of the compound of Formula 1 (VBIT-4) and/or Formula 10 (AKOS-022) and/or Formula 3 (VBIT-12) on induction of startle habituation and PPI in animals is examined.

For habituation, six trials of a single acoustic stimulus are presented to each mouse. To provide a consistent acoustic environment and to mask external noises, a continuous background noise level of 70 dB within each startle chamber is maintained. The peak or average response from each mouse on each of six trials is collected, and then the six responses are averaged for each mouse. Five more trials at the end of PPI are performed. The results are averaged and compared to the original six trials. The difference of startle responses between the initial six and the last five trials are considered the amount of habituation. Analyses can include the independent variable (e.g., vehicle or drug treatment) as a factor in analyses of variance (ANOVA) on the dependent measures (difference of the average of the first and last six trials).

The assay includes total of 36 trials. The three prepulse stimuli are of duration of 20 msec. For each mouse the following metrics are determined: 1) Average response magnitude on pulse-only, trials 1 to 6 and 32 to 36; 2) Average response magnitude in each of the four trial types between trials 7 and 31 inclusively (i.e., ten pulse-only trials and five each of the three prepulse variations). The first block of pulse-only trials are analyzed as measures of startle reactivity. The first and last blocks of pulse-only trials are analyzed together in a repeated measure ANOVA to assess habituation of acoustic startle across the test session. The four values (3, 6, or 12 dB above background) derived from trials 7 to 31 are used to assess PPI which is calculated for each mouse as: Percentage score: PPI=100%×{[pulse-only units-(prepulse+pulse units)]/(pulse-only units)}.

Male 129 SVE adult mice are first tested at baseline. Four groups of mice (typically 10 mice in each group) are treated with the compounds of Formulae 1 (VBIT-4), Formula 10 (AKOS-022), Formula 3 (VBIT-12) or with vehicle (0.9% DMSO). The mice receive the compounds in drinking water as described in Example 6 above at 20 mg/kg throughout the experiment.

Amphetamine is a drug that may induce psychosis, and amphetamine-induced psychosis is used as a model for primary psychotic disorders. Specifically, amphetamine induces disruption of habituation. Amphetamine (10 mg/kg) is administered 30 minutes before the experiments. The effect of VBIT-4 and/or AKOS-022 and/or VBIT-12 on habituation disruption by amphetamine is measured.

Example 8: Effects of the Compounds of Formula 1 (VBIT-4) or Formula 10 (AKOS-022) on Depression Male BALB/c mice aged 8 weeks are divided to two groups: a control group receiving vehicle solution (0.9% DMSO) and a treatment group receiving a solution of the compound of Formula 1 (VBIT-4) and/or the compound of Formula 10 (AKOSS-022) and/or the compound of Formula 3 (VBIT-12) in the drinking water as described in Example 6 hereinabove. The compound is provided at 20 mg/kg dissolved in 0.9% DMSO.

Novelty Suppressed Feeding Test

After the last treatment is administered, the mice do not receive any food for 24 hours (water was available ad libitum). At the end of this period, each animal is introduced into a 50×50×30 (height) cm plastic arena located in a specialized behavioral room in which all behavioral tests were tracked by cameras. The cameras may be linked to a computer installed with behavioral tracking software, for example EthoVision (XT 10). A pellet of food is placed on an elevated surface in the center of the arena. Time elapsing from the introduction of the animal into the arena until it commences eating (latency to feed), total distance move, velocity and time spent in the arena periphery (lateral 10 cm on each side) and center are recorded. The animal is then removed from the arena immediately after it begins to eat or after not doing so for 5 min. After the test, the animal is immediately transferred to its home cage and left to consume a previously weighed amount of food for 10 minutes. On completion of this period the food is weighed again to calculate the home cage food consumption. The rating of the animals' behavior is conducted by two experimenters who are blind to the treatment received by each mouse. The mean of the two ratings is calculated and used for the statistical analysis.

Sweet Preference Model of Anhedonia and Forced Swim Test Model for Despair

Sweet Preference

Mice are housed individually in cages having two 200 ml bottles containing tap water for 5 days. For the next 6 days, one of the bottles is replaced with a bottle containing a 5% sucrose solution and the other is left to contain tap water. The two bottles are presented for 12 h in the dark phase, following 12 h deprivation in the light phase, switching the sides on day 3.

Body weight is monitored weekly and fluid intake monitored daily.

Sucrose preference is calculated as the percent of the total fluid intake.

Forced Swim Test (FST)

Forced Swim Test (FST) is an animal model used to assess antidepressant compounds in preclinical studies. In this paradigm, mice are forced to swim in an inescapable cylinder filled with water. Under these conditions, mice will initially try to escape and eventually develop immobility behavior; this behavior is interpreted as a passive stress-coping strategy or depression-like behavior.

The assay is performed in swim tanks (for example, glass cylinders (46 cm height×20 cm diameter) containing water (20-cm deep, maintained at 24-25° C.).

One week after the sweet preference test, the mice are tested in the FST. The test compound is administered to each mice 15-30 min before swim session, e.g. by i.v. route. Each mouse is filmed and scored blindly after first establishing reliability between two blind observers (r=0.94) in the last 4 min as described in Lin et al. (Lin T, et al., 2012. Int J Dev Neurosci. 30(2). 113-20). The dependent measures were: (1) Immobility: No movement except for minimal paw and tail movements necessary to keep afloat, (2) Climbing: rhythmic bilateral movements of forelimbs and hindlimbs with body stretched vertically along the periphery of the container, and (3) Swimming which was calculated as the difference between 4 min and the time spent in immobility plus climbing.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

The invention claimed is:

1. A method for treating a CNS-associated disorder selected from the group consisting of psychotic disorder, mood disorder and neurodegenerative disease, the method comprising the step of administering to a subject in need thereof at least one compound of the general formula (I):

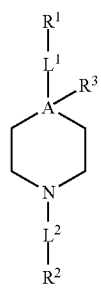

Formula (I)

wherein:

A is carbon (C) or nitrogen (N);

$R^3$ is absent, a hydrogen, an unsubstituted or substituted amide, or a heteroalkyl comprising 3-12 atoms (apart from hydrogen atoms), wherein at least one atom is a nitrogen, sulfur or oxygen atom, wherein when A is nitrogen (N), $R^3$ is absent;

$L^1$ is absent or is an amino linking group —$NR^4$—, wherein $R^4$ is hydrogen, a $C_{1-5}$-alkyl, a $C_{1-5}$-alkylene or a substituted alkyl —$CH_2R$, wherein R is a functional group selected from the group consisting of hydrogen, halo, haloalkyl, cyano, nitro, hydroxyl, alkyl, alkenyl, aryl, alkoxyl, aryloxyl, aralkoxyl, alkylcarbamido, arylcarbamido, amino, alkylamino, arylamino, dialkylamino, diarylamino, arylalkylamino, aminocarbonyl, alkylaminocarbonyl, arylaminocarbonyl, alkylcarbonyloxy, arylcarbonyloxy, carboxyl, alkoxycarbonyl, aryloxycarbonyl, sulfo, alkylsulfonylamido, alkylsulfonyl, arylsulfonyl, alkylsulfinyl, arylsulfinyl and heteroaryl;

$R^1$ is a phenyl, which is optionally substituted with one or more of Z;

Z is independently at each occurrence a functional group selected from the group consisting of, hydrogen, halo, haloalkyl, haloalkoxy, perhaloalkoxy or $C_{1-2}$-perfluoroalkoxy, cyano, nitro, hydroxyl, alkyl, alkenyl, aryl, alkoxyl, aryloxyl, aralkoxyl, alkylcarbamido, arylcarbamido, amino, alkylamino, arylamino, dialkylamino, diarylamino, arylalkylamino, aminocarbonyl, alkylaminocarbonyl, arylaminocarbonyl, alkylcarbonyloxy, arylcarbonyloxy, carboxyl, alkoxycarbonyl, aryloxycarbonyl, sulfo, alkylsulfonylamido, alkylsulfonyl, arylsulfonyl, alkylsulfinyl, arylsulfinyl and heteroaryl;

$L^2$ is a linking group such that:

when A is nitrogen (N), $L^2$ is selected from the group consisting of butanamidylene, N-methylbutanamidylene, N,N-dimethylbutanamidylene, 4-hydroxybutanamidylene, 4-oxobutanamidylene, 4-hydroxy-N-methylbutanamidylene and 4-oxo-N-methylbutanamidylene, wherein the carbon (C) in third position of the butanamide moiety is bonded to the nitrogen (N) of the piperazine ring and the nitrogen (N) of the butanamide moiety is bonded to $R^2$; or $L^2$ is selected from the group consisting of 2-pyrrolidone, pyrrolidine-2,5-dione, 5-thioxo-2-pyrrolidone or 5-methoxy-2-pyrrolidone, wherein a carbon (C) of the pyrrolidine moiety is bonded to the nitrogen (N) of the piperazine ring and the nitrogen (N) of the pyrrolidine moiety is bonded to $R^2$; and when A is carbon (C), $L^2$ is selected from the group consisting of $C_{1-4}$alkylene or a group consisting of 4-10 atoms, apart from hydrogen atoms, optionally forming a ring, wherein at least one of the atoms is nitrogen, said nitrogen forming part of an amide group;

$R^2$ is a phenyl or a naphthyl, optionally substituted with halogen;

or an enantiomer, diastereomer, mixture or salt thereof.

2. The method of claim 1, wherein $L^2$ is a linking group selected from the group consisting of 4-hydroxybutanamidylene having the formula HO—$CH_2$—$C^*H$—$CH_2$—C(O)NH— wherein the asterisk denotes an attachment point, and pyrrolidine-2,5-dionylene.

3. The method of claim 1, wherein A is carbon (C), $R^3$ is an unsubstituted or substituted amide or a heteroalkyl group, and $L^2$ is methylene.

4. The method of claim 1, wherein the compound is of general Formula (Ia):

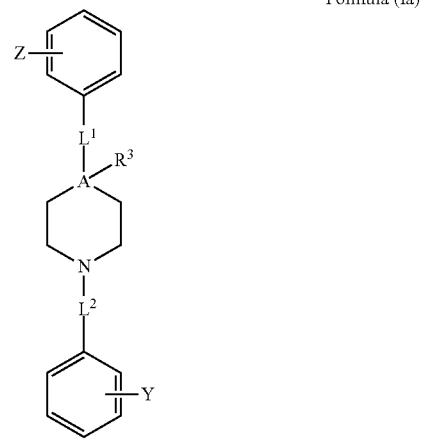

Formula (Ia)

wherein:

$L^{2'}$ is $L^2$; and

Y is halogen;

or an enantiomer, diastereomer, mixture or salt thereof.

5. The method of claim 4, wherein carbon (C) at position 3 of $L^{2'}$ is bonded to the nitrogen (N) of the piperazine ring or of the piperidine ring, and the nitrogen (N) of said $L^{2'}$ is bonded to the phenyl group.

6. The method of claim 1, wherein the compound is of the general formula (Ib):

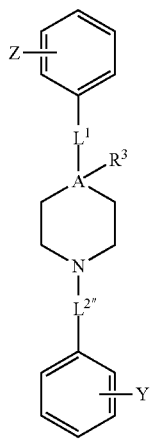

Formula (Ib)

wherein:
L¹ is absent;
L²'' is a pyrrolidinylene linking group, optionally substituted with one or two of alkyl, hydroxy, oxo or thioxo group;
Y is halogen;
or an enantiomer, diastereomer, mixture or salt thereof.

7. The method of claim 6, wherein L²'' is selected from the group consisting of 2-pyrrolidonylene, pyrrolidine-2,5-dionylene, 5-thioxo-2-pyrrolidinonylene and 5-methoxy-2-pyrrolidinonylene.

8. The method of claim 6, wherein a carbon (C) atom of the pyrrolidinyl moiety L²'' is bonded to the nitrogen (N) of the piperazine ring or the piperidine ring and the nitrogen (N) of the pyrrolidinyl moiety is bonded to the phenyl group.

9. The method of claim 1, wherein the compound is of the general formula (Ic):

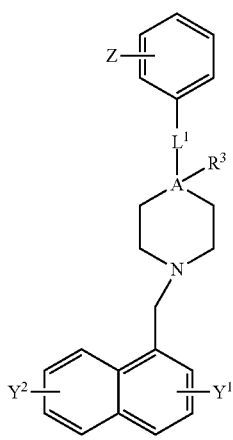

Formula (Ic)

wherein:
L¹ is —NH—;
Y¹ and Y² are each independently absent or a halogen;
or an enantiomer, diastereomer, mixture or salt thereof.

10. The method of claim 9, wherein R³ is —C(O)NHCH₂C(O)OH group.

11. The method of claim 1, wherein Z is $C_{1-2}$-alkoxy or $C_{1-2}$-perfluoroalkoxy.

12. The method of claim 1, wherein the compound is of the general formula (Id):

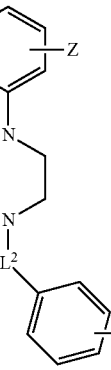

Formula (Id)

wherein
Z is $C_{1-2}$-perfluoroalkoxy, and Y is halogen.

13. The method of claim 12, wherein the compound is selected from the group consisting of a compound represented by the structure of Formula 1:

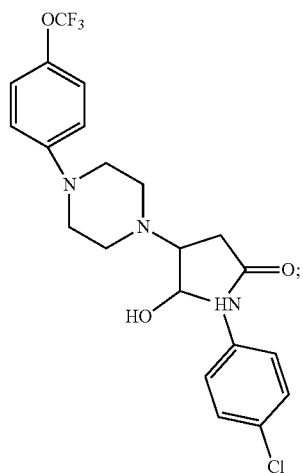

(Formula 1)

and a compound represented by the structure of Formula 2:

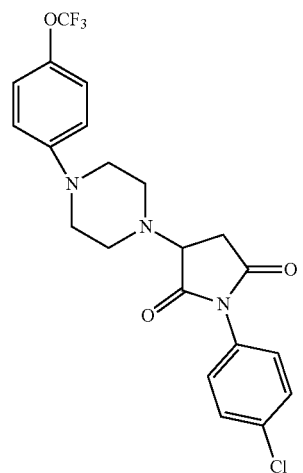

(Formula 2)

or an enantiomer, diastereomer, mixture or salt thereof.

14. The method of claim 10, wherein the compound is represented by the structure of Formula 3:

(Formula 3)

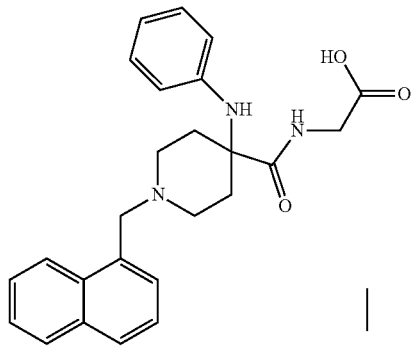

or an enantiomer, diastereomer, mixture or salt thereof.

15. A method for treating a CNS-associated disorder selected from the group consisting of psychotic disorder, mood disorder and neurodegenerative disease, the method comprising administering to a subject in need thereof at least one compound of Formula (IIa):

Formula (IIa)

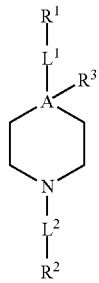

wherein:

A is carbon (C);

$R^3$ is hydrogen, an unsubstituted or substituted amide, or heteroalkyl chain comprising 3-12 atoms, apart from hydrogen atoms, wherein at least one is a heteroatom, selected from the group consisting of nitrogen, sulfur and oxygen;

$L^1$ is an amino linking group —$NR^4$—, wherein $R^4$ is hydrogen, a $C_{1-5}$-alkyl, a $C_{1-5}$-alkylene or a substituted alkyl —$CH_2R$, wherein R is a functional group selected from the group consisting of hydrogen, halo, haloalkyl, cyano, nitro, hydroxyl, alkyl, alkenyl, aryl, alkoxyl, aryloxyl, aralkoxyl, alkylcarbamido, arylcarbamido, amino, alkylamino, arylamino, dialkylamino, diarylamino, arylalkylamino, aminocarbonyl, alkylaminocarbonyl, arylaminocarbonyl, alkylcarbonyloxy, arylcarbonyloxy, carboxyl, alkoxycarbonyl, aryloxycarbonyl, sulfo, alkylsulfonylamido, alkylsulfonyl, arylsulfonyl, alkylsulfinyl, arylsulfinyl or heteroaryl;

when $R^3$ is heteroalkyl group comprising 3-12 atoms, apart from hydrogen atoms, then $L^1$ forms a ring with $R^3$;

$R^1$ is an aromatic moiety, which is optionally substituted with one or more of $C_{1-2}$-alkoxy, and/or $C_{1-2}$-perfluoroalkoxy;

$L^2$ is a linking group consisting of 4-10 atoms, apart from hydrogen atoms, optionally forming a ring, whereof at least one of the atoms is nitrogen, said nitrogen forming part of an amide group or $L^2$ is $C_{1-5}$alkyl or $C_{1-5}$alkylene; said linking group $L^2$ bonds piperidine or piperazine moiety at nitrogen (N) atom; and $R^2$ is an aryl, optionally substituted with halogen, optionally when $R^2$ is a phenyl it is substituted with halogen, further optionally when $R^2$ is naphthyl, $L^2$ is an alkylenyl group;

or an enantiomer, diastereomer, mixture or salt thereof.

16. The method according to claim 15, wherein the compound of Formula (IIa) has the Formula 10:

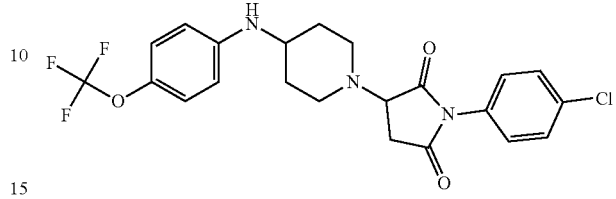

17. The method according to claim 15, wherein the compound of Formula (IIa) has the Formula 11:

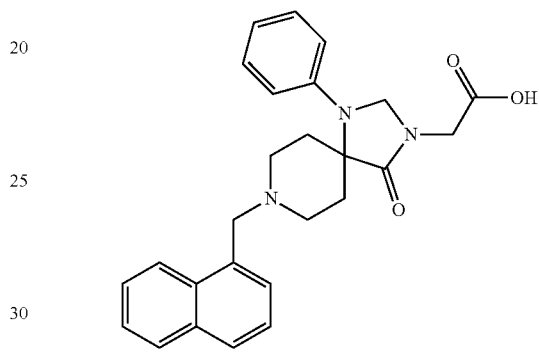

18. The method of claim 1, wherein the compound is administered within a pharmaceutical composition further comprising pharmaceutically acceptable excipients, diluents or carriers.

19. The method of claim 1, wherein:
the psychotic disorder is schizophrenia;
the mood disorder is selected from the group consisting of bipolar disorder, major depressive disorder, persistent depressive disorder and anxiety disorder; or
the neurodegenerative disease is selected from the group consisting of Alzheimer's disease, Parkinson disease and Amyotrophic Lateral Sclerosis (ALS).

20. The method of claim 1, wherein the compound is selected from the group consisting of:

(1)

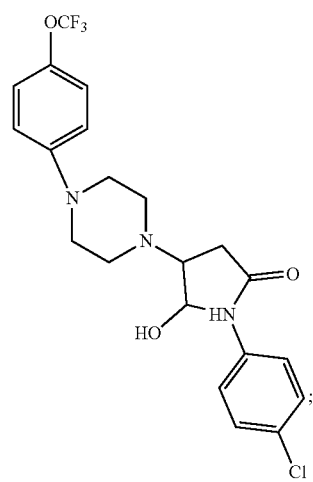

;

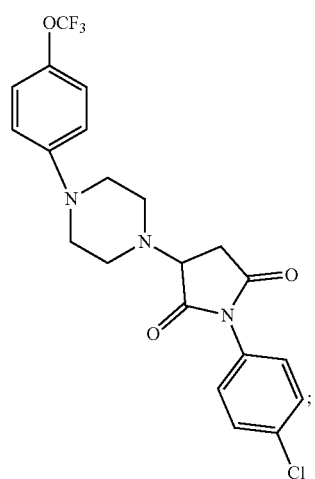
(2)
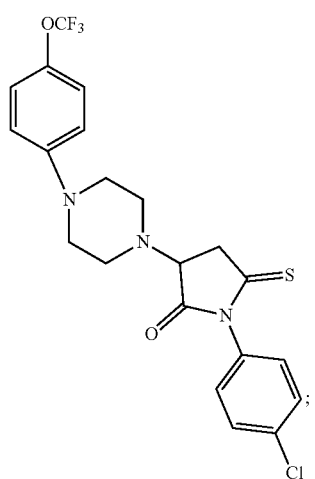
(5)
(3)
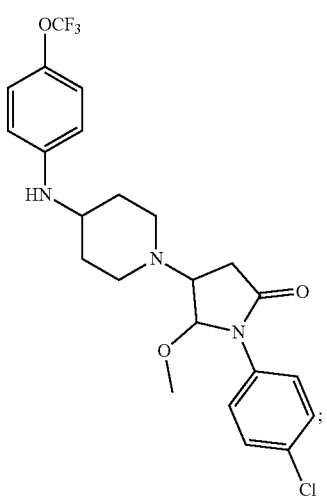
(6)
(4)
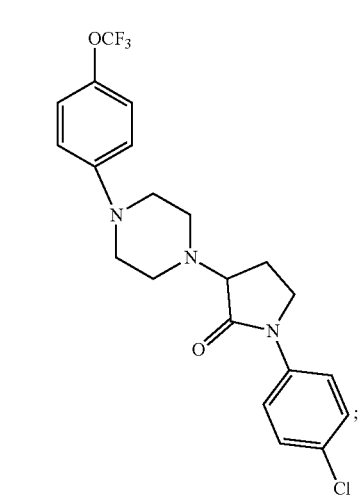
(7)

(9)
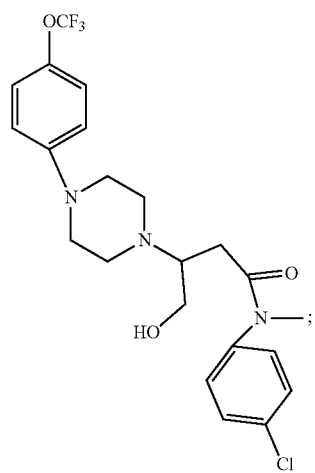
(10)
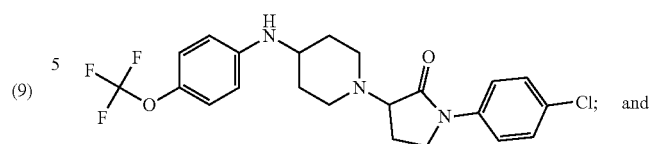
and
(11)
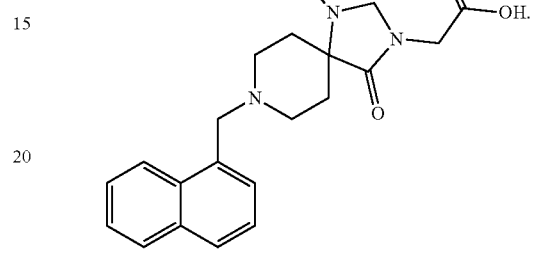
* * * * *